(12) United States Patent
Maines

(10) Patent No.: US 9,598,677 B2
(45) Date of Patent: *Mar. 21, 2017

(54) USE OF HUMAN BILIVERDIN REDUCTASE AND FRAGMENTS THEREOF FOR THE TREATMENT OF PROTEIN KINASE C-DELTA AND ERK RELATED CONDITIONS

(71) Applicant: University of Rochester, Rochester, NY (US)

(72) Inventor: Mahin D. Maines, Rochester, NY (US)

(73) Assignee: University of Rochester, Rochester, NY (US)

( * ) Notice: Subject to any disclaimer, the term of this patent is extended or adjusted under 35 U.S.C. 154(b) by 25 days.

This patent is subject to a terminal disclaimer.

(21) Appl. No.: 14/741,951

(22) Filed: Jun. 17, 2015

(65) Prior Publication Data

US 2015/0353902 A1 Dec. 10, 2015

Related U.S. Application Data

(63) Continuation of application No. 12/941,883, filed on Nov. 8, 2010, now Pat. No. 9,078,913.

(60) Provisional application No. 61/258,852, filed on Nov. 6, 2009.

(51) Int. Cl.
| | | |
|---|---|---|
| *A61K 38/00* | (2006.01) |
| *C12N 9/02* | (2006.01) |
| *A61K 38/44* | (2006.01) |
| *A61K 31/713* | (2006.01) |
| *C12N 5/00* | (2006.01) |

(52) U.S. Cl.
CPC ............ *C12N 9/001* (2013.01); *A61K 31/713* (2013.01); *A61K 38/44* (2013.01); *C12N 5/00* (2013.01); *C12Y 103/01024* (2013.01)

(58) Field of Classification Search
None
See application file for complete search history.

(56) References Cited

U.S. PATENT DOCUMENTS

| 6,969,610 | B2 | 11/2005 | Maines | |
|---|---|---|---|---|
| 9,078,913 | B2 * | 7/2015 | Maines | ............ A61K 38/44 |
| 2003/0027124 | A1 | 2/2003 | Maines | |
| 2005/0119205 | A1 | 6/2005 | Maines | |
| 2005/0287132 | A1 | 12/2005 | Maines | |
| 2007/0117769 | A1 | 5/2007 | Maines | |
| 2009/0214627 | A1 | 8/2009 | Maines | |

FOREIGN PATENT DOCUMENTS

| WO | 2005007090 | 1/2005 |
|---|---|---|
| WO | 2006017578 | 2/2006 |
| WO | 2006089270 | 8/2006 |

OTHER PUBLICATIONS

Wegiel et al, Cell Surface Biliverdin Reductase Mediates Biliverdin-induced Anti-inflammatory Effects via Phosphatidylinositol 3-Kinase and Akt (J Biol Chem. Aug. 7, 2009; 284(32): 21369-21378).*
Lerner-Marmarosh et al., "Human Biliverdin Reductase is an ERK Activator: hBVR is an ERK Nuclear Transporter and is Required for MAPK Signaling," PNAS 105(19):6870-6875 (2008).
Tudor et al., "Biliverdin Reductase is a Transporter of Heme into the Nucleus and is Essential to Regulation of HO-1 Gene Expression by Hematin," Biochem. J. 413(3):405-416 (2008).
Lerner-Marmarosh et al., "Regulation of TNF-alpha-Activated PKC-zeta Signaling by the Human Biliverdin Reductase: Identification of Activating and Inhibitory Domains of the Reductase," FASEB J. 21:3949-3962 (2007).
Maines, "Human Biliverdin Reductase, a Previously Unknown Activator of Protein Kinase C βII," Journal of Biological Chemistry, 282(11): 8110-8122, 2007.
Maines, "New Insights into Biliverdin Reductase Functions: Linking Heme Metabolism to Cell Signaling," Physiol. 20:382-389 (2005).
Lerner-Marmarosh et al., "Human Biliverdin Reductase: A Member of the Insulin Receptor Substrate Family with Serine/Threonine/Tyrosine Kinase Activity," PNAS 102(20):7109-7114 (2005).
Miralem et al., "Small Interference RNA-Mediated Gene Silencing of Human Biliverdin Reductase, But Not That of Heme Oxygenase-(1), Attenuates Arsenite-Mediated Induction of the Oxygenase and Increases Apoptosis in 293A Kidney Cells," J. Biol. Chem. 280(17):17084-17092 (2005).
Kravets et al., "Biliverdin Reductase, a Novel Regulator for Induction of Activating Transcription Factor-2 and Heme Oxygenase-1," J. Biol. Chem. 279(19):19916-19923 (2004).
Gibbs et al., "Biliverdin Inhibits Activation of NF-KappaB: Reversal of Inhibition by Human Biliverdin Reductase," Int. J. Cancer 121:2567-2574 (2007).
Kapitulnik et al,. "Pleiotropic Functions of Biliverdin Reductase: Cellular Signaling and Generation of Bilirubin—A Cytoprotective/Cytotoxic Tetrapyrrole," Trends Pharmacol. Sci. 30(3):129-37 (2009).
Miralem et al., "Human Biliverdin Reductase Suppresses Goodpasture Antigen Binding Protein (GPBP) Kinase Activity: The Reductase Regulates TNF-Alpha- NF-KappaB-Dependent GPBP Expression," J. Biol. Chem. 285 (17):12557-8 (2010).
Gibbs et al., "Characterization of the Human Biliverdin Reductase Gene Structure and Regulatory Elements: Promoter Activity is Enhanced by Hypoxia and Suppressed by TNF-Alpha-Activated NF-KappaB," FASEB J. Epub Apr. 21, 2010 (doi:1 0.1096/fj.09-144592).
Gibbs et al., "Formation of ternary complex of human biliverdin reductase-protein kinase Cδ-ERK2 protein is essential for ERK2-mediated activation of Elk1 protein, nuclear factor-κβ, and inducible nitric-oxidase synthase (iNOS)," J Biol. Chem. Jan. 6, 2012;287(2):1066-79.

(Continued)

*Primary Examiner* — James H Alstrum Acevedo
*Assistant Examiner* — Sergio Coffa
(74) *Attorney, Agent, or Firm* — Riverside Law LLP

(57) ABSTRACT

The present invention is directed to methods of modulating PKC-δ activity and PKC-δ/ERK complex activity in cells via biliverdin reductase. Methods and compositions for diagnosing and treating a PKC-δ and PKC-δ/ERK complex related condition are also disclosed.

11 Claims, 24 Drawing Sheets

(56) References Cited

OTHER PUBLICATIONS

Maines, "Biliverdin Reductase: PKC Interaction as the Cross-talk of MAPK and PI3K Signaling Pathways," Antioxid. Redox Signal. 9(12):2187-95 (2007).
Kaidanovich-Beilin et al., "Peptides Targeting Protein Kinases: Strategies and Implications," Physiology 21:411-418, 2006.
Paddock, "Is Type 2 Diabetes An Autoimmune Disease?," Medical News Today. MediLexicon, Intl., Apr. 19, 2011.
Chen et al., The effect of PKC-delta inhibitor Rottlerin on human colon cancer cell line SW1116 and its mechanism, Zhonghua Zhong Liu Za Zhi. Aug. 2006;28(8):564-7.
Ueda, "Protein Kinase C δ Activates the MEK-ERK Pathway in a Manner Independent of Ras and Dependent on Raf," Journal of Biological Chemistry, 271 (38): 23512-23519, 1996.
Waterston, Accession No. AC004939.1, BLAST screen capture.
Maines et al., "Human biliverdin Ixα reductase is a zinc-metalloprotein; Characterization of pur8ified and *Escherichi coli* expressed enzymes," Eur. J. Biochem. 235:372-381 (1996).

\* cited by examiner

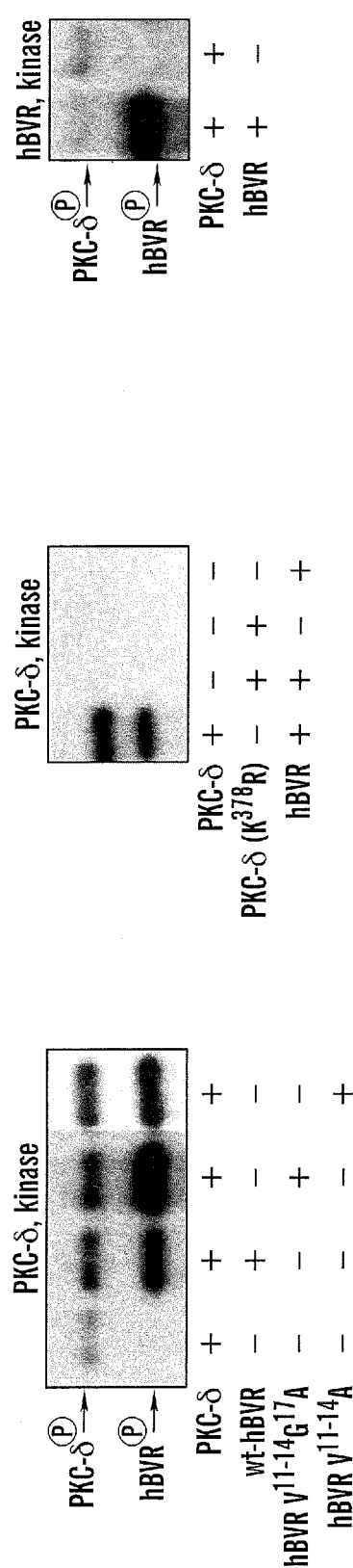

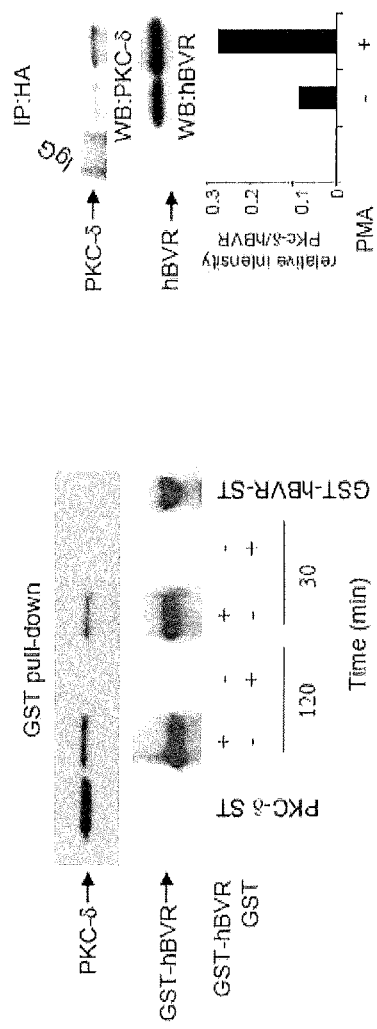
*FIG. 2A*
*FIG. 2B*
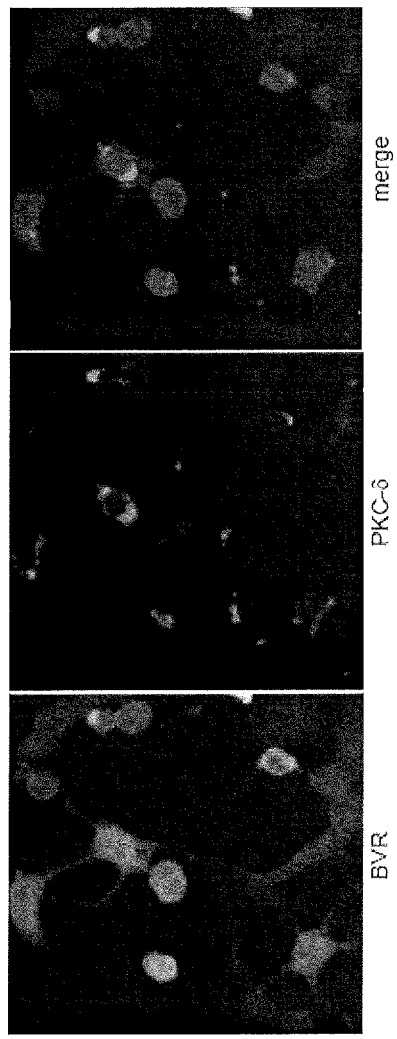
*FIG. 2C*

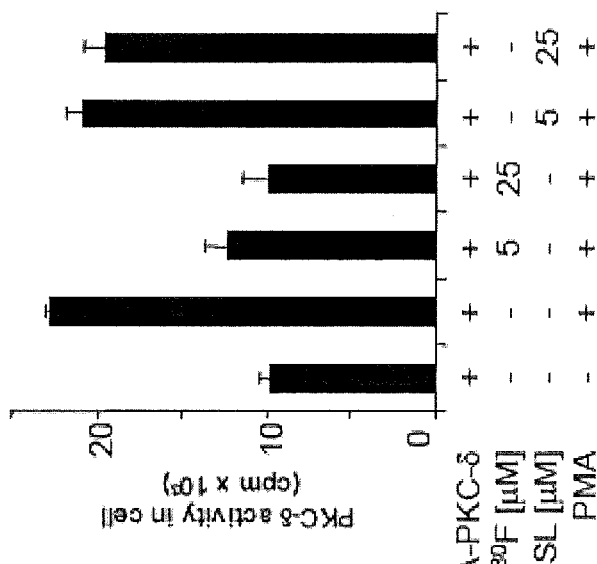
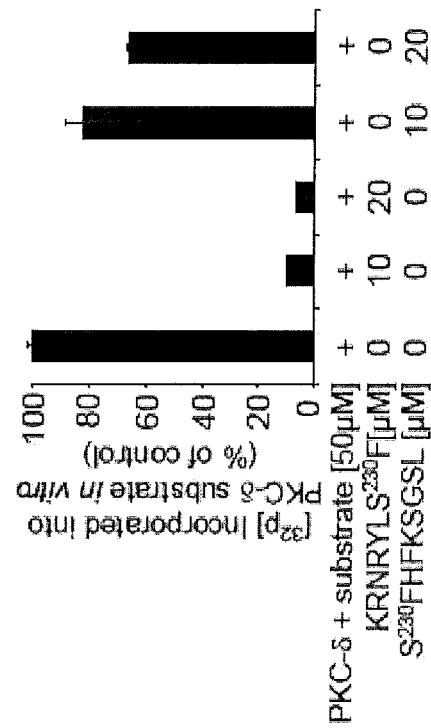
FIG. 5A
FIG. 5B

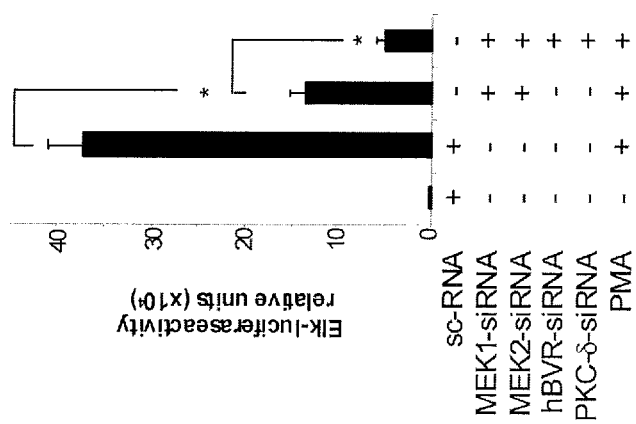
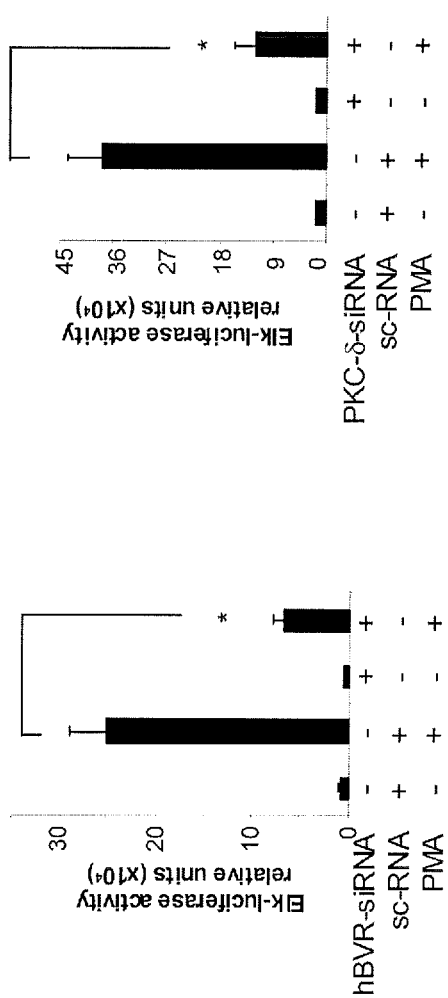
FIG. 11C
FIG. 11B
FIG. 11A

USE OF HUMAN BILIVERDIN REDUCTASE AND FRAGMENTS THEREOF FOR THE TREATMENT OF PROTEIN KINASE C-DELTA AND ERK RELATED CONDITIONS

CROSS-REFERENCE TO RELATED APPLICATIONS

The present application is a continuation application of, and claims priority to, U.S. application Ser. No. 12/941,883, filed Nov. 8, 2010, now allowed, which claims priority to U.S. Provisional App. Ser. No. 61/258,852, filed Nov. 6, 2009, which applications are incorporated by reference herein in their entireties.

STATEMENT REGARDING FEDERALLY SPONSORED RESEARCH OR DEVELOPMENT

This invention was made with government support under grant numbers R01ES004066 and R0ES012187 awarded by National Institutes of Health/National Institute of Environmental Health Sciences. The government has certain rights in this invention.

FIELD OF THE INVENTION

The present invention is directed to methods of modulating PKC-δ activity via biliverdin reductase or peptide fragments derived therefrom. Methods and compositions for treating PKC-δ related conditions are also disclosed.

BACKGROUND OF THE INVENTION

Human biliverdin reductase ("hBVR") is a small (296 residue) soluble protein with two distinct types of activities, the commonly known reductase activity and the more recently characterized kinase activity (reviewed in Kapitulnik et al., "Pleiotropic Functions of Biliverdin Reductase: Cellular Signaling and Generation of Cytoprotective and Cytotoxic Bilirubin," *Trends Pharmacol. Sci.* 30:129-137 (2009)). As a reductase, hBVR is unique among all enzymes described to date in being a dual pH/cofactor-dependent catalyst for conversion of biliverdin-IXα to bilirubin-IXα (Maines et al., "Purification and Characterization of Human Biliverdin Reductase," *Arch. Biochem. Biophys.* 300: 320-326 (1993), Hayes et al., "The Effect of pH on the Initial Rate Kinetics of the Dimeric Biliverdin-IXalpha Reductase From the *Cyanobacterium Synechocystis* PCC6803," *FEBS J.* 276: 4414-4425 (2009)). Biliverdin, the substrate for hBVR, is a product of heme (Fe-protoporphyrin IX) oxidation by the HO enzymes, the stress-inducible HO-1 and the constitutive HO-2 (Mancuso et al., "Bilirubin: An Endogenous Scavenger of Nitric Oxide and Reactive Nitrogen Species," *Redox Rep.* 11:207-213 (2006), Ryter et al., "Carbon Monoxide and Bilirubin: Potential Therapies for Pulmonary/Vascular Injury and Disease," *Am. J. Respir. Cell. Mol. Biol.* 36:175-182 (2007)). Activation of hBVR is a key component of cellular defense mechanisms. In its capacity as a kinase, hBVR transfers phosphates to target substrate serine, threonine, and tyrosine residues and, hence, is a member of the rare family of dual-specificity kinases that have been described by Hunter T., "Signaling-2000 and Beyond," *Cell* 100:113-127 (2000).

The primary structure of hBVR features, arguably, an unprecedented number of consensus signaling motifs (Kapitulnik et al., "Pleiotropic Functions of Biliverdin Reductase: Cellular Signaling and Generation of Cytoprotective and Cytotoxic Bilirubin," *Trends Pharmacol. Sci.* 30:129-137 (2009)). The motifs, with demonstrated functionality include nuclear localization and nuclear export signals, high and low affinity MAPK docking sites, a C-Box ($F^{162}GFP$) that is contained in the bulky ring motif (FXFXXF), and a D(δ)-Box ($K^{275}KRILXXLXL$), respectively (Jacobs et al., "Multiple Docking Sites on Substrate Proteins Form a Modular System that Mediates Recognition by ERK MAP Kinase," *Genes Dev.* 13:163-175 (1999), Karin M., "Inflammation-Activated Protein Kinases As Targets for Drug Development," *Proc. Am. Thorac. Soc.* 2:386-390 (2005)). Those docking sites, as well as the $H^{280}CX_{10}CC$ motif (CC-Box), are present in the C-terminal half of hBVR. The cysteine-rich motif is also present in C1 and C2/C2-like domains (Newton et al., "Protein Kinase C: A Paradigm for Regulation of Protein Function by Two Membrane-Targeting Modules," *Biochim. Biophys. Acta* 1376:155-172 (1998)).

At multiple levels hBVR exerts input in transduction of insulin/stress-response signals; this includes activation of both conventional and atypical Protein Kinase-C(PKC) family members such as PKC-βII and PKC-ζ, respectively (Lerner-Marmarosh et al., "Regulation of TNF-alpha-Activated PKC-zeta Signaling By the Human Biliverdin Reductase: Identification of Activating and Inhibitory Domains of the Reductase," *FASEB J.* 21:3949-3962 (2007), Maines M. D., "Biliverdin Reductase: PKC Interaction At the Cross-Talk of MAPK and PI3K Signaling Pathways," *Antioxid. Redox Signal.* 9:2187-2195 (2007), Lerner-Marmarosh et al., "Human Biliverdin Reductase is an ERK Activator; hBVR is an ERK Nuclear Transporter and is Required for MAPK Signaling," *Proc. Natl. Acad. Sci. U.S.A.* 105:6870-6875 (2008), Wegiel et al., "Cell Surface Biliverdin Reductase Mediates Biliverdin-Induced Anti-Inflammatory Effects Via PI3K and AKT," *J. Biol. Chem.* 284:21369-21378 (2009)). PKC-δ is a member of the novel PKC family of serine/threonine kinases (Benes et al., "Modulation of PKC-delta Tyrosine Phosphorylation and Activity in Salivary and PC-12 Cells by Src Kinases," *Am. J. Physiol. Cell Physiol.* 280:C1498-1510 (2001)) that is activated as the result of a conformational change induced by its cofactor, phorbolester/diacylglycerol that results in release of auto inhibition and exposure of the activation loop. $Ca^{2+}$ and phorbolesters are activator cofactors for conventional PKCs, but PKC-δ is unique in that its cysteine-rich C2-like domain does not bind $Ca^{2+}$.

hBVR and PKC-δ are universally expressed in tissues. In the cell, the type of stimuli that activate hBVR and PKC-δ extensively overlap. In addition to insulin, hBVR and PKC-δ have in common a varied list of extracellular stimuli such as TNF-α and reactive oxygen species (ROS) that are linked to cell survival, apoptosis and proliferation (Jackson et al., "The Enigmatic Protein Kinase C delta: Complex Roles in Cell Proliferation and Survival," *FASEB J.* 18:627-636 (2004)). Activation of the two enzymes has been viewed in context of a variety of functions, with the most notable being pro-apoptosis (PKC) and anti-apoptosis (hBVR), respectively (Kapitulnik et al., "Pleiotropic Functions of Biliverdin Reductase: Cellular Signaling and Generation of Cytoprotective and Cytotoxic Bilirubin," *Trends Pharmacol. Sci.* 30:129-137 (2009), Gschwendt, M., "Protein kinase C Delta," *Eur. J. Biochem.* 259:555-564 (1999), Miralem et al., "Small Interference RNA-Mediated Gene Silencing of Human Biliverdin Reductase, But Not That of Heme Oxygenase-1, Attenuates Arsenite-Mediated Induction of the Oxygenase and Increases Apoptosis in 293A Kidney Cells," *J. Biol. Chem.* 280:17084-17092 (2005), Stempka et al., "Requirements of Protein Kinase cdelta for Catalytic Function. Role of Glutamic Acid 500 and Autophosphorylation on Serine 643," *J. Biol. Chem.* 274:8886-8892 (1999)).

PKC-δ phosphorylates S/T residues in specific motifs (Nishikawa et al., "Determination of the Specific Substrate Sequence Motifs of Protein Kinase C Isozymes," *J. Biol. Chem.* 272:952-960 (1997), Hanks et al., "The Protein Kinase Family: Conserved Features and Deduced Phylogeny of the Catalytic Domains," *Science* 241:42-52 (1988)), that are found in hBVR, for example, RXXS/T in KRNRYLS$^{230}$FHFKSGSL, SXR/KS$^{21}$ that flanks the ATP-binding domain of hBVR, and S$^{294}$ that flanks the CC-Box (Maines et al., "Human Biliverdin IXalpha Reductase is a Zinc-Metalloprotein. Characterization of Purified and *Escherichia Coli* Expressed Enzymes," *Eur. J. Biochem.* 235:372-381 (1996)). Y$^{228}$LSF is in one of the consensus SH-2 domain binding sites of hBVR, with the tyrosine residue being a substrate for IRK (Lerner-Marmarosh et al., "Human Biliverdin Reductase: A Member of the Insulin Receptor Substrate Family With Serine/Threonine/Tyrosine Kinase Activity," *Proc. Natl. Acad. Sci. U.S.A.* 102:7109-7114 (2005)). Based on the noted similarities in hBVR and PKC-δ in phosphorylation motifs, upstream activators and downstream effector kinases, while also considering the opposing outcome of their activation to cell death and survival, it is possible these proteins have integrated and closely linked activities. It would be desirable, therefore, to identify whether BVR or, more particularly, peptide fragments of BVR are capable of modulating the activity of PKC-δ.

The present invention is directed to overcoming these and other deficiencies in the art.

SUMMARY OF THE INVENTION

A first aspect of the present invention relates to a method of modulating PKC-δ activity and/or PKC-δ/ERK complex activity in a population of cells. This method involves administering to the population of cells an agent selected from the group consisting of a mammalian biliverdin reductase ("BVR") protein, a mammalian BVR peptide fragment, and an agent that modulates BVR expression or activity under conditions effective to modulate PKC-δ activity and/or PKC-δ/ERK complex activity in the population of cells.

A second aspect of the present invention relates to a method of treating a PKC-δ and/or a PKC-δ/ERK complex related condition in a subject. This method involves administering to the subject having the PKC-δ and/or PKC-δ/ERK complex related condition an agent that modulates PKC-δ activity and/or PKC-δ/ERK complex activity, where the agent is selected from the group consisting of a mammalian BVR protein, a mammalian BVR peptide fragment, and an agent that modulates BVR expression or activity. The agent is administered to the subject under conditions effective to treat the PKC-δ and/or PKC-δ/ERK complex related condition.

A third aspect of the present invention relates to a method of treating a PKC-δ and/or PKC-δ/ERK complex related condition in a subject. This method involves administering to the subject having the PKC-δ and/or PKC-δ/ERK complex related condition an agent that inhibits PKC-δ activity, where the agent is a mammalian BVR peptide fragment selected from the group consisting of [K/R][K/R]N[K/R]Y[L/I]S[F/W] (SEQ ID NO:18), [K/R][K/R][K/R][I/L]LX$_2$LX$_1$LA (SEQ ID NO:24), and FXFPXF[S/T]G (SEQ ID NO:33), wherein X is any amino acid. The agent that inhibits PKC-δ activity is administered under conditions effective to treat the PKC-δ related condition.

A fourth aspect of the present invention relates to a method of treating a PKC-δ related autoimmune condition in a subject. This method involves administering to the subject having the PKC-δ related autoimmune condition an agent that enhances PKC-δ activity, where the agent is selected from the group consisting of a mammalian BVR protein, a mammalian BVR peptide fragment, and an agent that modulates BVR expression or activity. The agent that enhances PKC-δ activity is administered to the subject under conditions effective to treat the PKC-δ related autoimmune condition.

A fifth aspect of the present invention is directed to a method of diagnosing a PKC-δ related condition in a subject. This method involves obtaining a sample from the subject, contacting the sample from the subject with a BVR peptide under conditions effective for PKC-δ mediated BVR peptide phosphorylation and detecting the level of BVR peptide phosphorylation. The detected level of BVR peptide phosphorylation is compared with a reference level of BVR peptide phosphorylation and the PKC-δ related condition is diagnosed in a subject based on the comparison.

Other aspects of the present invention are directed to isolated BVR peptides and pharmaceutical compositions containing such isolated peptides. One isolated BVR peptide of the present invention has an amino acid sequence comprising GL[K/R][K/R]N[K/R][F/Y/W]L[S/T][F/Y/W][K/R/H][F/Y/W][K/R][S/T] (SEQ ID NO: 44). Another isolated peptide of the present invention comprises an amino acid sequence of [K/R][K/R]N[K/R]Y[L/I]S[F/W] (SEQ ID NO:18). Peptides consisting of SEQ ID NO: 44 or SEQ ID NO: 18 are also contemplated.

The present invention relates to the use of BVR, BVR peptides, and other agents that modulate BVR to regulate the activity of PKC-δ and PKC-δ/ERK complex activity. The examples presented herein demonstrate that BVR activates PKC-δ through a direct protein-protein interaction and that BVR is a substrate for PKC-δ phosphorylation. Therefore, enhancing the expression and/or activity of BVR can enhance the level of active PKC-δ and/or level of PKC-δ/ERK complex formation and activity in cells, thereby providing therapeutic utility for disease conditions characterized by a reduction in PKC-δ and/or PKC-δ/ERK activity. The examples presented herein also describe the identification of BVR peptides that potently inhibit the activity of PKC-δ and PKC-δ/ERK activity. These BVR peptides and other inhibitors of BVR expression and activity can be used to inhibit the level of active PKC-δ and the level of PKC-δ/ERK complex formation and activity in cells, thereby providing therapeutic utility for disease conditions characterized by excessive PKC-δ and/or PKC-δ/ERK activity.

BRIEF DESCRIPTION OF THE DRAWINGS

FIGS. 1A-1G demonstrate hBVR stimulation of PKC-δ activity in vitro. hBVR activates PKC-δ autophosphorylation, and hBVR is a substrate for PKC-δ as shown in FIG. 1A. Increasing concentrations of hBVR were pre-incubated with 5 ng active recombinant human PKC-δ for 5 min at room temperature prior to the kinase assay. The PKC-δ kinase assay was carried out in kinase buffer as described infra in the presence of [$^{32}$P]ATP (20 μM) for 40 min at 30° C. The reaction products were separated by SDS-PAGE and transferred to a PVDF membrane before autoradiography. PKC-δ activity is increased in presence of hBVR as shown in the graph of FIG. 1B. GST-hBVR (2 μg) was pre-incubated with active PKC-δ for 5 min at room temperature prior the addition of 12.5 μM MBP substrate. Control PKC assays lacked either hBVR or MBP. The reaction was started by the addition of [$^{32}$P]γATP (50 μM) and stopped after 15 min by the addition of $H_3PO_4$; and bound $^{32}$P was measured using a p81 filter assay. FIG. 1C shows that the kinase-dead hBVR activates PKC-δ. Kinase reactions performed as described for FIG. 1A included 2 μg of hBVR, or the hBVR-$V^{11-14}$→A and kinase inactive $V^{11-14}$, $G^{17}$→A mutants. FIG. 1D shows that the kinase-efficiency of PKC-δ is required for its activation by hBVR. Phosphorylation of hBVR by wt- or the kinase-deficient mutant of PKC-δ ($K^{378}$→R) was tested in a PKC-δ kinase assay system. FIG. 1E shows that PKC-δ is not phosphorylated by hBVR. Phosphorylation of PKC-δ was tested in reaction conditions optimal for hBVR kinase activity. Experimental details are provided infra. The graph of FIG. 1F shows that hBVR augments PMA-induced PKC-δ activation. Active PKC-δ (10 ng) was incubated in the presence or absence of 1 μg hBVR with increasing concentrations of PMA in 50 μL kinase buffer for 30 minutes at 30° C. The reaction was stopped with $H_3PO_4$ prior to measuring bound $^{32}$P using the p81 filter assay. hBVR increases PMA induced PKC-δ activity towards its substrate as depicted in FIG. 1G. PKC-δ (10 ng), pre-incubated with or without 1 μg hBVR, was incubated in kinase buffer with increasing concentrations of PMA and the PKC-δ specific substrate ARRKRK-GSFFGG (20 μM) (SEQ ID NO: 52). The reaction was started with addition of ATP and stopped after 20 min, and then incorporated radioactivity was measured as described above.

FIGS. 2A-2C show that hBVR and PKC-δ bind and co-localize in the cell. GST-hBVR stably binds to PKC-δ as shown in the GST pull-down assay of FIG. 2A. Lysate (1 mg protein) prepared from 293A cells overexpressing PKC-δ was subjected to the GST-pull-down assay using GST-hBVR (10 μg/ml) or GST alone. At the indicated times, the GSH-agarose bound fraction was collected, washed, and separated on SDS-PAGE together with PKC-δ and GST-hBVR standards (ST). Proteins in the cell were transferred to a nitrocellulose membrane, which was probed sequentially with anti-PKC-δ, and anti-hBVR antibodies. hBVR and PKC-δ co-immunoprecipitate as shown in the immunoblot of FIG. 2B. HEK-293A cells were transfected with PKC-δ and HA-tagged hBVR, and starved and treated with PMA for 15 minutes. Cell lysates were immunoprecipitated with anti-HA antibodies and blotted onto nitrocellulose. The graph shows the ratio between intensities of PKC-δ and hBVR protein bands. The membrane was sequentially probed with anti-PKC-δ and anti-hBVR antibodies. The immunofluorescence cell images of FIG. 2C depict hBVR and PKC-δ co-localization. Cells co-expressing pEGFP-hBVR and pDs2-red-PKC-δ were grown in chamber slides. Co-localization of proteins was suggested by the yellow-orange fluorescence in merged images of the green fluorescence of hBVR and red fluorescence of PKC-δ. Nuclei were stained with DAPI.

As shown in FIG. 4A, hBVR-derived peptide compares favorably with a commercial PKC-δ peptide substrate. Cells transfected with PKC-δ plasmid were starved and treated with PMA (as in FIG. 3A). To measure PKC-δ activity, the hBVR-derived peptide $G^{222}$LKRNRYLSFHFK (SEQ ID NO: 70) and the commercial PKC-δ specific substrate ARRKRKGSFFGG (SEQ ID NO: 52) were used separately as substrates in an in situ kinase assay. hBVR-based peptide is a high affinity substrate for PKC-δ as shown in FIG. 4B. Kinase assay was performed in vitro using increasing concentrations of the SH2 containing hBVR-derived peptide (aa222-234) as the substrate. Incorporation of phosphate into the peptide was measured using the p81 method as described infra and was fitted to the Michaelis-Menton equation using GraphPad Prism 3.0 software. Similar assays were carried out for PKC-ζ and PKC-βII using conditions optimal for each (Lerner-Marmarosh et al., "Regulation of TNF-alpha-Activated PKC-zeta Signaling By the Human Biliverdin Reductase: Identification of Activating and Inhibitory Domains of the Reductase," *FASEB J.* 21:3949-3962 (2007), Maines M. D., "Biliverdin Reductase: PKC Interaction At the Cross-Talk of MAPK and PI3K Signaling Pathways," *Antioxid. Redox Signal.* 9:2187-2195 (2007), which are hereby incorporated by reference in their entirety). Raw data were expressed as a percentage of the V-max for each enzyme to allow visual comparison of the Km for each PKC. The Km values for PKC-ζ, PKC-βII, and PKC-δ were 14.03, 6.89 and 1.59 μM, respectively. As shown in the graph of FIG. 4C, the serine residue in hBVR aa222-234 peptide is a specific target of PKC-δ, and the upstream positively charged residues are essential for its phosphorylation. Peptides with the indicated substitutions in the hBVR-based peptide were tested as substrates for PKC-δ kinase activity. Each peptide is identified by its sequence ($G^{222}$LKRNRYLSFHFK, SEQ ID NO: 70; $G^{222}$LKRNRYLAFHFKSGSL, SEQ ID NO:58, $G^{222}$LKRNRYLAFHFK, SEQ ID NO:59; GLAANAYLSFHFK, SEQ ID NO:60) with residues in bold being the amino acid replacement sites.

FIGS. 5A-5E show that the hBVR-derived peptide KRNRYLSF (SEQ ID NO:19) inhibits PMA-induced activation and membrane translocation of PKC-δ in cells. A fragment of the hBVR-derived substrate peptide is a potent inhibitor of PKC-δ kinase activity as shown in FIG. 5A. In vitro phosphorylation of the commercial PKC-δ substrate peptide was measured in the presence of the two fragments derived from the hBVR-based PKC-δ substrate peptide. FIG. 5B shows that the KRNRYSLF (SEQ ID NO:19) peptide suppresses PKC-δ activity in cells. Cells were seeded into a 48-well plate, transfected with pcDNA3-PKC-δ plasmid and treated with hBVR-based peptides, myr-KRNRYLSF (SEQ ID NO:19) or myr-SFHFKSGSL (SEQ ID NO: 53), during the last 2 hours of the 24 hour starvation period. Thereafter cells were treated with PMA for 15 minutes and analyzed by the in situ kinase assay as described infra. The constitutively active PKC-δ is also suppressed by the inhibitory hBVR peptide as shown in FIG. 5C. Cells seeded into a 48-well plate were transfected with constitutively active pcDNA-PKC-δ, treated with myr-KRNRYLSF (SEQ ID NO:19), and analyzed as described above for FIG. 5B. The inhibitory hBVR peptide is active against both PKC-δ and PKC-ζ as depicted in FIG. 5D. The in vitro assays for PKC-βII and PKC-ζ were performed essentially as described for PKC-δ, under reaction conditions specific to each PKC as described infra. The hBVR peptide KRNRYLSF was added at the concentrations indicated. The inhibitory hBVR peptide also inhibits translocation of PKC-δ to the plasma membrane in response to PMA as depicted in the FIG. 5E. Cells were seeded into a slide chamber, starved, pretreated with 10 μM hBVR-derived peptides (myr-KRNRYLS$^{230}$F, or myr-S$^{230}$FHFKSGSL), as described infra, and treated with PMA for 15 min. Cells were fixed, permeabilized and treated with anti-PKC-δ polyclonal antibodies followed with Red-x— conjugated secondary antibody then subjected to confocal microscopy. Red-fluorescence of PKC-δ was visualized on an Olympus confocal microscope.

FIG. 7C shows that hBVR increases PKC-δ autophosphorylation. Increasing concentrations (0, 0.06, 0.3 μM) of hBVR were pre-incubated with active recombinant human PKC-δ for 5 min at room temperature prior to the kinase assay. The PKC-δ assay was carried out as described infra in the presence of $^{32}$P-ATP (20 μM) for 40 min at 30° C. The reaction products were separated by SDS-PAGE and transferred to a PVDF membrane before autoradiography. Kinase-inactive hBVR is a substrate for PKC-δ as depicted in FIG. 7D. Kinase reactions performed as described above (FIG. 7C) included 2 μg of wt hBVR, or the kinase-inactive V$^{11-14}$, G$^{17}$→A mutant. The activity of PKC-δ is increased by hBVR in cells as shown in FIG. 7E. Wildtype(wt)-PKC-δ or its kinase-inactive mutant were either overexpressed alone or co-expressed with hBVR in HEK293A cells. After starvation, cells were treated with PMA for 15 min and cell lysates were immunoprecipitated with anti-PKC-δ antibody. Immunoprecipitates were then subjected to in vitro p81 kinase assay with a PKC-δ peptide substrate as described in the text. *p<0.001. FIG. 7F shows that hBVR increases kinase activity of constitutively active PKC-δ in cells. Cells were transfected with constitutively active pcDNA-PKC-δ-CA and, where indicated, co-transfected with a plasmid expressing hBVR. Cells were starved prior to the treatment with PMA. PKC-δ activity was determined as in (e). *p<0.001.

FIGS. 8A-8F depict the ternary complex formed between PKC-δ, ERK-1/2, and hBVR. hBVR, PKC-δ, and ERK-1/2 form a ternary complex as shown in FIG. 8A. Cells were co-transfected with PKC-δ and HA-tagged hBVR, starved, and either left untreated or treated with either PMA or IGF-1 for 15 min. Immunoprecipitates with anti-HA antibodies were examined by immunoblotting by sequentially probing the membrane with anti-PKC-δ, anti-ERK-1/2 or anti-hBVR antibodies. Depletion of hBVR inhibits binding between PKC-δ and ERK-1/2 as shown in FIG. 8B. Cells were transfected with PKC-δ and, where indicated, infected with viral constructs to express either siRNA for hBVR or sc-RNA as a control. After starvation cells were treated with IGF-1 and cell lysates were immunoprecipitated with anti-ERK-1/2 antibody and analyzed by western blot, which was probed with anti-PKC-δ followed by anti-ERK-1/2 antibodies. FIG. 8C shows that hBVR, PKC-δ, ERK-1/2, and MEK1 form a quaternary complex endogenously. hBVR and PKC-δ form a complex in cells stimulated with IGF-1 or PMA. Cells were starved overnight and treated with IGF-1 or PMA; PKC-δ in the cells lysates was collected by immunoprecipitation. Proteins in the immunoprecipitate were detected on a western blot by sequentially probing with anti-hBVR, anti-ERK1/2, MEK1, or PKC-δ antibodies. PKC-δ kinase activity is not required for ERK binding as depicted in FIG. 8D. Cells were transfected with pcDNA-PKC-δ or with plasmid containing kinase-inactive PKC-δ (KD), starved, and either left untreated or treated with IGF-1 for 15 min. Cell lysates were precipitated with an anti-ERK-1/2 mouse monoclonal antibody and immunoprecipitates were tested by immunoblotting first with anti PKC-δ followed by anti-ERK-1/2 antibodies. FIG. 8E shows that siRNA for ERK-1 and ERK-2 suppresses binding between hBVR and PKC-δ. Cells were co-transfected with HA-hBVR, PKC-δ, and synthetic siRNA for ERK-1, ERK-2, or the scRNA control, and then treated with PMA and processed as in FIG. 8A. After immunoprecipitation with anti-HA antibody transferred proteins on the membrane were detected by sequentially probing antibodies to PKC-δ, ERK-1/2, or hBVR. FIG. 8F shows that si-PKC-δ blocks binding between hBVR and ERK. Cells transfected with HA-hBVR plasmid were also co-transfected with synthetic siRNA for PKC-δ or with control scRNA, treated with IGF-1 or PMA and processed as described above for FIG. 8A. Immunoprecipitates with anti-HA antibody were transferred to the membrane and sequentially probed with anti-ERK-1/2 and anti-hBVR antibodies.

FIG. 9B shows that hBVR-derived peptide FGFPAFSG (SEQ ID NO: 34) suppresses binding between hBVR and PKC-δ. Cells co-transfected with HA-hBVR and PKC-δ were starved and loaded with hBVR-derived C-(aa162-169) or D-box (aa275-285) peptides in myristoylated form. After treatment with IGF-1, cell lysates were immunoprecipitated with anti-HA antibody followed by Western blotting. The blot was sequentially probed with anti-PKC-δ and anti-hBVR antibodies. FGF-PAFSG (SEQ ID NO: 34) but not KKRILHCLGLA (SEQ ID NO: 25) hBVR-derived peptides suppress binding between ERK1/2 and PKC-δ (FIG. 9D). Cells transfected with PKC-δ were processed as described above for FIG. 9B, except that immunoprecipitation was with anti-ERK1/2.

As shown in FIG. 10A, the 3'-truncated PKC-δ does not autophosphorylate. PKC-δ or the PKC-δ-3'-truncated mutant (Δ656-676) were tested for autophosphorylation as described in FIG. 7A; lower panel shows western blot of total PKC-δ. PKC-δ-3'-truncated mutant is inactive as a kinase (FIG. 10B). Wildtype (wt) PKC-δ or the C-terminally truncated mutant were examined for kinase activity in the presence and absence of hBVR. The C-terminal peptide of PKC-δ suppresses Elk1 activation (FIG. 10C). Cells were transfected with Elk1 reporters and co-transfected with pcDNA-PKC-δ. The cells were starved and treated with a myristoylated PKC-δ bulky Ring motif (C-terminal peptide: S$^{658}$AFAGFSFVNPKFEHLLED; SEQ ID NO: 57) for 2 h prior to treatment with PMA. Cell lysates were assayed for luciferase and the activity normalized against β-galactosidase as an internal standard. As indicated by the data of FIG. 10D, the C-terminus of PKC-δ is required for its activation of Elk1. Cells were transfected with Elk1 reporters and co-transfected with either wt PKC-δ or with PKC-δ 3'-truncated mutant (3'-PKC-δ). Lysates were assayed for luciferase activity after treatment with PMA as described above. The PKC-δ C-terminus is not required for binding to hBVR (FIG. 10E). Cells co-expressing pcDNA-HA-hBVR with pcDNA-PKC-δ wt or 3'-trunctated plasmids were starved and treated with IGF-1 or PMA. Proteins precipitated from cell lysates with anti-HA antibody were examined on western blots sequentially probed with anti-PKC-δ and anti-hBVR antibodies. ERK2 binds to C-terminally truncated PKC-δ as shown in FIG. 10F. Cells were transfected with either wt or C-terminally truncated PKC-δ, starved and treated with either IGF-1 or PMA. ERK2 was immunoprecipitated from cell lysates and examined by sequential immunoblotting with anti-PKC-δ and anti-ERK12 antibodies.

FIGS. 11A-11C show that hBVR is a determining factor in transcriptional activity of MEK/ERK1/2/Elk1 signaling. Depletion of hBVR from cells suppresses PMA-dependent Elk1 induction (FIG. 11A). Cells transfected with Elk1 reporters were infected with a virus expressing si-hBVR or with control sc-hBVR. The cells were then starved and treated with PMA as described in the Examples. Cell lysates were assayed for luciferase and the activity normalized against β-galactosidase as an internal standard. The effect of siRNA for PKC-δ on Elk1 activity is shown in FIG. 11B. Cells transfected with Elk-1 reporters were also transfected with siRNA for PKC-δ or with control sc-RNA, as indicated. Depletion of MEK1/2 suppresses PMA-induced Elk1 activation (FIG. 11C). HEK293A cells were transfected with Elk1 luciferase reporters and, where indicated, co-transfected with siRNA for MEK-1 and -2, PKC-δ, and/or hBVR. Cells were processed as in describe above for FIG. 11A.

DETAILED DESCRIPTION OF THE INVENTION

Figure 1B:
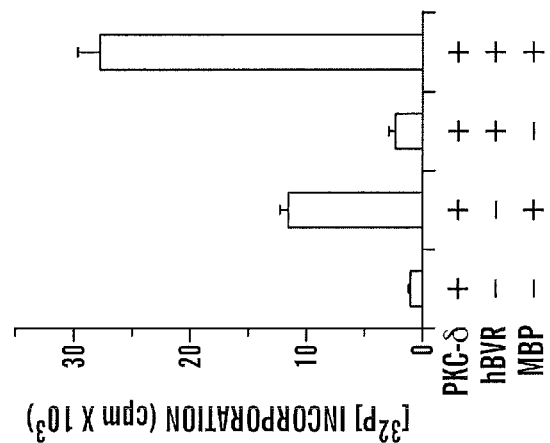

The present invention is generally directed to methods and compositions for modulating PKC-δ activity and PKC-δ/ERK complex formation and activity in vitro and in vivo. Accordingly, one aspect of the present invention relates to a method of modulating PKC-δ activity and PKC-δ/ERK complex activity in a population of cells. This method involves administering to the population of cells an agent selected from the group consisting of a mammalian biliverdin reductase ("BVR") protein, a mammalian BVR peptide fragment, and an agent that modulates BVR expression or activity, where the administering is carried out under conditions effective to modulate PKC-δ activity and PKC-δ/ERK complex activity in the population of cells.

A second aspect of the present invention relates to a method of treating a PKC-δ and/or a PKC-δ/ERK complex related condition in a subject. This method involves administering to the subject having the PKC-δ and/or PKC-δ/ERK complex related condition an agent that modulates PKC-δ activity and/or PKC-δ/ERK complex activity, where the agent is selected from the group consisting of a mammalian BVR protein, a mammalian BVR peptide fragment, and an agent that modulates BVR expression or activity. The agent is administered to the subject under conditions effective to treat the condition.

In one embodiment of the present invention, the agent administered to the population of cells or to a subject having a PKC-δ or PKC-δ/ERK complex related condition is an agent that increases or enhances PKC-δ activity and PKC-δ/ERK complex formation and activity. This is achieved by administering an agent that upregulates or increases the concentration and/or activity of BVR or mimics BVR activity in the target cells. Suitable agents include, for example, BVR or BVR-derived peptides which can be administered to the cells of interest either directly or by recombinant expression of a nucleic acid molecule encoding BVR or a BVR-derived peptide (i.e., via gene therapy). The concentration of activated cellular BVR can also be increased by introducing an agent, e.g., a small molecule or upstream signaling molecule, that increases BVR transcription and expression or activity in a cell.

Consistent with this aspect of the invention, increasing PKC-δ activity and/or PKC-δ/ERK complex formation can be targeted to specific cell populations, for example, cancer cells, neuronal cells, cardiomyocytes, leukocytes (e.g., T-cells), fibroblasts, or any other cell population where increasing PKC-δ activity and/or PKC-δ/ERK complex formation is desirable. Methods of achieving cell-specific targeting are known in the art and are described infra. PKC-δ activity and/or PKC-δ/ERK complex formation can be modulated in a population of cells by introducing BVR, BVR-derived peptides, or recombinant BVR nucleic acid molecules into the cells of interest in vitro or in vivo.

As used herein, the terms "biliverdin reductase" and "BVR" refer to any mammalian BVR, but preferably human BVR ("hBVR"). One form of hBVR has an amino acid sequence corresponding to SEQ ID NO: 1 as follows:

```
Met Asn Ala Glu Pro Glu Arg Lys Phe Gly Val Val
 1               5                  10

Val Val Gly Val Gly Arg Ala Gly Ser Val Arg Met
            15                  20

Arg Asp Leu Arg Asn Pro His Pro Ser Ser Ala Phe
25                  30                  35

Leu Asn Leu Ile Gly Phe Val Ser Arg Arg Glu Leu
                40                  45

Gly Ser Ile Asp Gly Val Gln Gln Ile Ser Leu Glu
    50                  55                  60

Asp Ala Leu Ser Ser Gln Glu Val Glu Val Ala Tyr
                65                  70

Ile Cys Ser Glu Ser Ser Ser His Glu Asp Tyr Ile
            75                  80

Arg Gln Phe Leu Asn Ala Gly Lys His Val Leu Val
85                  90                  95

Glu Tyr Pro Met Thr Leu Ser Leu Ala Ala Ala Gln
            100                 105

Glu Leu Trp Glu Leu Ala Glu Gln Lys Gly Lys Val
            110                 115                 120

Leu His Glu Glu His Val Glu Leu Leu Met Glu Glu
                125                 130

Phe Ala Phe Leu Lys Lys Glu Val Val Gly Lys Asp
            135                 140

Leu Leu Lys Gly Ser Leu Leu Phe Thr Ser Asp Pro
145                 150                 155

Leu Glu Glu Asp Arg Phe Gly Phe Pro Ala Phe Ser
                160                 165

Gly Ile Ser Arg Leu Thr Trp Leu Val Ser Leu Phe
        170                 175                 180

Gly Glu Leu Ser Leu Val Ser Ala Thr Leu Glu Glu
                185                 190

Arg Lys Glu Asp Gln Tyr Met Lys Met Thr Val Cys
        195                 200

Leu Glu Thr Glu Lys Lys Ser Pro Leu Ser Trp Ile
205                 210                 215

Glu Glu Lys Gly Pro Gly Leu Lys Arg Asn Arg Tyr
                220                 225

Leu Ser Phe His Phe Lys Ser Gly Ser Leu Glu Asn
        230                 235                 240

Val Pro Asn Val Gly Val Asn Lys Asn Ile Phe Leu
                    245                 250

Lys Asp Gln Asn Ile Phe Val Gln Lys Leu Leu Gly
        255                 260

Gln Phe Ser Glu Lys Glu Leu Ala Ala Glu Lys Lys
265                 270                 275

Arg Ile Leu His Cys Leu Gly Leu Ala Glu Glu Ile
            280                 285

Gln Lys Tyr Cys Cys Ser Arg Lys
        290                 295
```

Heterologous expression and isolation of hBVR is described in Maines et al., Human Biliverdin IXalpha Reductase is a Zinc-Metalloprotein. Characterization of Purified and *Escherichia coli* Expressed Enzymes," *Eur. J. Biochem.* 235(1-2):372-381 (1996) and Maines et al., "Purification and Characterization of Human Biliverdin Reductase," *Arch. Biochem. Biophys.* 300(1):320-326 (1993), which are hereby incorporated by reference in their entirety. A nucleic acid molecule encoding this form of hBVR has a nucleotide sequence corresponding to SEQ ID NO: 2 as follows:

```
ggggtggcgc ccggagctgc acggagagcg tgcccgtcag tgaccgaaga agagaccaag    60
atgaatgcag agcccgagag gaagtttggc gtggtggtgg ttggtgttgg ccgagccggc   120
tccgtgcgga tgagggactt gcggaatcca caccttcct cagcgttcct gaacctgatt   180
ggcttcgtgt cgagaaggga gctcgggagc attgatggag tccagcagat ttctttggag   240
gatgctcttt ccagccaaga ggtggaggtc gcctatatct gcagtgagag ctccagccat   300
gaggactaca tcaggcagtt ccttaatgct ggcaagcacg tccttgtgga atacccatg    360 acactgtcat tggcggccgc tcaggaactg tgggagctgg ctgagcagaa aggaaaagtc   420
ttgcacgagg agcatgttga actcttgatg gaggaattcg ctttcctgaa aaagaagtg    480 gtggggaaag acctgctgaa agggtcgctc ctcttcacat ctgacccgtt ggaagaagac   540
cggtttggct tccctgcatt cagcggcatc tctcgactga cctggctggt ctccctcttt   600
ggggagcttt ctcttgtgtc tgccactttg gaagagcgaa aggaagatca gtatatgaaa   660
atgacagtgt gtctggagac agagaagaaa agtccactgt catggattga agaaaaagga   720
```

-continued

```
cctggtctaa aacgaaacag atatttaagc ttccatttca agtctgggtc cttggagaat    780
gtgccaaatg taggagtgaa taagaacata tttctgaaag atcaaaatat atttgtccag    840
aaactcttgg gccagttctc tgagaaggaa ctggctgctg aaaagaaacg catcctgcac    900
tgcctggggc ttgcagaaga aatccagaaa tattgctgtt caaggaagta agaggaggag    960
gtgatgtagc acttccaaga tggcaccagc atttggttct tctcaagagt tgaccattat   1020
ctctattctt aaaattaaac atgttgggga aacaaaaaaa aaaaaaaaa               1070
```

The open reading frame which encodes hBVR of SEQ ID NO: 1 extends from nucleotide 1 to nucleotide 888.

Another form of hBVR has been reported by Komuro et al., NCBI Accession No. G02066, direct submission to the EMBL Data Library (1998) ("Komuro"), which is hereby incorporated by reference in its entirety. Differences between the hBVR of SEQ ID NO: 1 and the hBVR of Komuro et al. are at amino acid residues 3, 154, 155, and 160. Specifically, residue 3 can be either alanine or threonine, residue 154 can be either alanine or serine, residue 155 can be either aspartic acid or glycine, and residue 160 can be either aspartic acid or glutamic acid.

In addition, BVR from other mammals, such as rat, mouse, pig, and chimp that have been recombinantly expressed and isolated (see e.g., Fakhrai et al., "Expression and Characterization of a cDNA for Rat Kidney Biliverdin Reductase. Evidence Suggesting the Liver and Kidney Enzymes are the Same Transcript Product," *J. Biol. Chem.* 267(6):4023-4029 (1992), which is hereby incorporated by reference in its entirety) can be employed in the methods of the present invention. The rBVR amino acid sequence (NCBI Reference Sequence NP_446302.1, which is hereby incorporated by reference in its entirety) shares about 82% amino acid identity to the hBVR of SEQ ID NO: 1, with variations in amino acid residues being highly conserved. The mouse BVR sequence (NCBI Reference Sequence NP_080954, which is hereby incorporated by reference in its entirety) is about 81 percent identical to the human BVR sequence of SEQ ID NO: 1, with variations in amino acid residues being highly conserved. The pig, chimp (NCBI Reference Sequence XP_001136150, which is hereby incorporated by reference in its entirety), and rhesus monkey (NCBI Reference Sequence XP_001095668, which is hereby incorporated by reference in its entirety) BVR sequences are each about 98 percent identical to the human BVR sequence of SEQ ID NO: 1, with variations in amino acid residues being highly conserved. The cattle BVR sequence (NCBI Reference Sequence NP_001091040, which is hereby incorporated by reference in its entirety) is about 95 percent identical to the human BVR sequence of SEQ ID NO: 1, with variations in amino acid residues being highly conserved. The relatedness of several of the mammalian BVR proteins is illustrated in the ClustalW (1.81) alignment presented below:

```
Human    MNAEPERKFGVVVVGVGRAGSVRMRDLRNPHPSSAFLNLIGFVSRRELGSIDGVQQISLE
Pig      MNAEPERKFGVVVVGVGRAGSVRMRDLRNPHPSSAFLNLIGFVSRRELGSIDGVQQISLE
Chimp    MNTEPERKFGVVVVGVGRAGSVRMRDLRNPHPSSAFLNLIGFVSRRELGSVDGVQQISLE
Rhesus   MNTEPERKFGVVVVGVGRAGSVRMRDLRNPHPSSAFLNLIGFVSRRELGSIDGVQQISLE
Cattle   MNTEPERKFGVVVVGVGRAGSVRMRDLRNPHASSAFLNLIGFVSRRELGSIDEVPQISLE
         **:************************** *******************:*  *****

Human    DALSSQEVEVAYICSESSSHEDYIRQFLNAGKHVLVEYPMTLSLAAAQELWELAEQKGKV
Pig      DALSSQEVEVAYICSESSSHEDYIRQFLNAGKHVLVEYPMTLSLAAAQELWELAEQKGKV
Chimp    DALSSQEVEVAYICSESSSHEDYIRQFLNAGKHVLVEYPMTLSLAAAQELWELAEQKGKV
Rhesus   DALSSQEVEVAYICSESSSHEDYIRQFLNAGKHVLVEYPMTLSLAAAQELWELAEQKGKV
Cattle   DALSSQEVEVAFICSESSSHEDYIRQFLNAGKHVLVEYPMTLSWVAAKDLWELAEQKGKV
         ***********:******************************  **::**********

Human    LHEEHVELLMEEFAFLKKEVVGKDLLKGSLLFTSDPLEEDRFGFPAFSGISRLTWLVSLF
Pig      LHEEHVELLMEEFAFLKKEVVGKDLLKGSLLFTAGPLEEERFGSPAFSGISRLTWLVSLF
Chimp    LHEEHVELLMEEFAFLKKEVVGKDLLKGSLLFTAGPLEEERFGPPAFSGISRLTWLVSLF
Rhesus   LHEEHVELLMEEFAFLKKEVVGKDLLKGSLLFTAGPLEEERFGFPAFSGISRLTWLVSLF
Cattle   LHEEHVELLMEEFAFLKKEVVGKDLLKGSLLFTAAPLEEERFGFPAFSGISRLTWLVSLF
         ********************************: ****:*** ****************

Human    GELSLVSATLEERKEDQYMKMTVCLETEKKSPLSWIEEKGPGLKRNRYLSFHFKSGSLEN
Pig      GELSLVSATLEERKEDQYMKMTVCLETEKKSPLSWIEEKGPGLKRNRYLSFHFKSGSLEN
Chimp    GELSLVSATLEERKEDQYMKMTVCLETEKKSPLSWIEEKGPGLKRNRYLSFHFKSGSLEN
Rhesus   GELSLVSATLEERKEDQYMKMTVCLETEKKSPLSWIEEKGPGLKRNRYLSFHFKSGSLEN
Cattle   GELSLVSATLEERKEDQYMKMTVCLETENKSPLTWIEEKAPGLKRNRRLSFHFRSGSLEN
         ***************************:****:***** ******* *****:******

Human    VPNVGVNKNIFLKDQNIFVQKLLGQFSEKELAAEKKRILHCLGLAEEIQKYCCSRK  (SEQ ID NO: 1)
Pig      VPNVGVNKNIFLKDQNIFVQKLLGQFSEKELAAEKKRILHCLGLAEEIQKYCCSRK  (SEQ ID NO: 3)
Chimp    VPNVGVNKNIFLKDQNIFVQKLLGQFSEKELAAEKKRILHCLGLAEEIQKYCCSRK  (SEQ ID NO: 4)
Rhesus   VPNVGVNKNIFLKDQNIFVQKLLGQFSEKELAAEKKRILHCLGLAEEIQKYCCSRK  (SEQ ID NO: 5)
Cattle   MPNVGINKNIFLKDQNIFVQKLLGQFSEEELAAEKKRILHCLWLAGEIQKHCCSKQ  (SEQ ID NO: 6)
         :****:*********************:************* ** **:*:**::
```

It is to be understood that the present invention contemplates the use of any mammalian or non-mammalian BVR sequence in the formation of the recombinant genes, expression systems, and peptides of the present invention. Homologous BVR peptides from mammals and non-mammals other than those described above are preferably characterized by an amino acid identity of at least about 60 percent, more preferably at least about 70 percent or 80 percent, most preferably at least about 85 percent or 90 percent or 95 percent as compared to human BVR of SEQ ID NO: 1. Other mammalian and non-mammalian cDNA molecules can be identified based upon their alignment with the BVR cDNA of SEQ ID NO: 2, where such alignment preferably is at least about 60 percent identical more preferably at least about 70 percent, 75 percent, 80 percent, 85 percent, 90 percent, or 95 percent identical. Alternatively, other mammalian BVR encoding cDNA molecules can be identified by the ability of mammalian cDNA sequences to hybridize to the complement of SEQ ID NO: 2 under stringent hybridization and wash conditions. Exemplary stringent hybridization and wash conditions include, without limitation, hybridization at 50° C. or higher (i.e., 55° C., 60° C., or 65° C.) in a hybridization medium that includes 0.9× (or higher, such as 2× or 5×) sodium citrate ("SSC") buffer, followed by one or more washes at increasing stringency using 0.2×SSC buffer at temperatures from 42° C. up to the temperature of the hybridization step. Higher stringency can readily be attained by increasing the temperature for either hybridization or washing conditions or decreasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency.

Various BVR peptide fragments can also be employed in practicing this aspect of the present invention to increase PKC-δ activity and/or PKC-δ/ERK complex formation and activity. Suitable BVR peptides are encompassed by the amino acid consensus sequence of KXCCSXX (SEQ ID NO:7), where X at position 2 is an aromatic amino acid (preferably H or Y), and X at positions 6 and 7 are polar amino acids (preferably Q, R, or K). Peptides comprising this consensus sequence and well as peptides consisting of this consensus sequence are contemplated. The peptide is preferably myristoylated.

Exemplary peptides include, without limitation, both acetylated and unacetylated forms of KYCCSRK (SEQ ID NO:8), KHCCSRK (SEQ ID NO:9), KYCCSKK (SEQ ID NO:10), KHCCSKK (SEQ ID NO:11), KYCCSKQ (SEQ ID NO:12), KHCCSKQ (SEQ ID NO:13), KYCCSRQ (SEQ ID NO:14), KHCCSRK (SEQ ID NO:15), KYCCSKR (SEQ ID NO:16), and KHCCSKR (SEQ ID NO:17). Such peptides can be produced by several means as described infra.

As noted above, cellular uptake of the BVR polypeptide or peptide fragments results in enhanced BVR activity, which in turn activates PKC-δ activity and enhances PKC-δ/ERK complex formation and activity. Increasing PKC-δ activity and/or PKC-δ/ERK complex formation and activity has therapeutic benefits in a variety of disease conditions characterized by a reduction in PKC-δ activity and/or PKC-δ/ERK activity. Specifically, increasing PKC-δ activity and/or PKC-δ/ERK complex formation and activity is desirable for the treatment of autoimmune disorders (e.g., lupus, arthritis, and Good Pasture syndrome), inflammatory disease, (e.g., chronic inflammatory conditions), and cytostasis. Accordingly, the present invention is directed to a methods of treating a PKC-δ autoimmune condition and other PKC-δ or PKC-δ/ERK complex related conditions in a subject that involve administering to the subject an agent that increases PKC-δ or PKC-δ/ERK complex activity under conditions effective to treat the condition. Suitable agents for enhancing PKC-δ activity and PKC-δ/ERK complex formation and activity include those described supra.

As used herein, a "subject" having a PKC-δ or PKC-δ/ERK complex related condition encompasses any animal, but preferably a mammal. More preferably, the patient is a human.

In another embodiment of the present invention it is desirable to inhibit PKC-δ activity, and/or inhibit or decrease PKC-δ/ERK complex formation and activity within a specific tissue or cell population. This can be achieved by administering to a population of cells or a subject, an agent that inhibits BVR expression or activity. Alternatively, as described herein, certain BVR peptides that have been identified as potent inhibitors of PKC-δ activity and PKC-δ/ERK complex formation and activity are suitable for use. Inhibition of PKC-δ activity and/or PKC-δ/ERK complex formation can be targeted to specific cell populations, for example, cancer cells, neuronal cells, cardiomyocytes, leukocytes, fibroblasts, or any other cell population where it is desirable to inhibit PKC-δ activity and/or PKC-δ/ERK complex formation or activity. Methods of achieving cell-specific targeting are known in the art and are described infra. PKC-δ activity and/or PKC-δ/ERK complex formation can be inhibited in a population of cells by introducing agents that inhibit BVR or BVR-derived peptides into the cell of interest in vitro or in vivo.

Agents that inhibit BVR expression and/or activity include any known protein, peptide, nucleic acid, and small molecule BVR inhibitors. Inhibitory BVR nucleic acid molecules include, without limitation, antisense molecules, siRNA molecules, shRNA molecules, and miRNA molecules.

Antisense nucleic acid molecules capable of hybridizing with an RNA transcript coding for BVR are expressed from a transgene which is prepared by ligation of a DNA molecule, coding for BVR, or a fragment or variant thereof, into an expression vector in reverse orientation with respect to its promoter and 3' regulatory sequences. Upon transcription of the DNA molecule, the resulting RNA molecule will be complementary to the mRNA transcript coding for the actual protein or polypeptide product. Ligation of DNA molecules in reverse orientation can be performed according to known techniques which are standard in the art. As discussed infra, recombinant molecules including an antisense sequence or oligonucleotide fragment thereof, may be directly introduced into cells of tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes.

As an alternative to full-length antisense BVR mRNA, siRNA can be used to decrease the cellular or nuclear concentration of BVR and its activity. siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the BVR nucleotide sequence. siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. As demonstrated infra in the Examples, BVR siRNA is an effective means for inhibiting BVR and subsequently inhibiting PKC-δ activity. siRNA molecules that effectively interfere with BVR expression that are suitable for use in the present invention include, without limitation:

```
                                    (SEQ ID NO: 48)
5'-UCCUCAGCGUUCCUGAACCUG;
and
                                    (SEQ ID NO: 49)
3'-AGGAGUCGCAAGGACUUGGAC.
```

Additional human BVR siRNA or sc-hBVR (containing a randomized variant of the sihBVR sequence) that are suitable for inhibiting PKC-δ activity and PKC-δ/ERK complex formation are known in the art (see Miralem et al., "Small Interference RNA-mediated Gene Silencing of Human Biliverdin Reductase, But not that of Heme Oxygenase-1, Attenuates Arsenite-Mediated Induction of the Oxygenase and Increases Apoptosis in 293A Kidney Cells," *J. Biol. Chem.* 280:17084-92 (2005), which is hereby incorporated by reference in its entirety).

Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway. shRNA molecules that effectively interfere with human BVR expression have been developed and are suitable for use in the methods of the present invention (see e.g., OriGene Technologies (Rockville, Md.) Catalogue No. TR314466).

In accordance with this embodiment of the present invention, BVR peptides that inhibit PKC-δ activity and PKC-δ/ERK complex formation and activity can also be administered. One BVR peptide that inhibits PKC-δ activity in accordance with this aspect of the invention has a consensus amino acid sequence of [K/R][K/R]N[K/R]Y[L/I]S[F/W] (SEQ ID NO:18). Peptides comprising this consensus sequence and well as peptides consisting of this consensus sequence are contemplated. Exemplary peptides encompassed by this consensus sequence include, without limitation, KRNRYLSF (SEQ ID NO:19), KKNRYLSF (SEQ ID NO:20), RRNRYLSF (SEQ ID NO:21), KRNRYISF (SEQ ID NO:22), KRNRYLSW (SEQ ID NO:23). Other peptides encompassed by the consensus amino acid sequence are also within the scope of the present invention.

A second BVR peptide that inhibits PKC-δ activity and PKC-δ/ERK complex formation and activity has a consensus amino acid sequence of [K/R][K/R][K/R][I/L]LXX-LXLA (SEQ ID NO:24), where X at amino acid positions 6, 7, and 9 is any amino acid. Peptides comprising this consensus sequence and well as peptides consisting of this consensus sequence are contemplated. Exemplary peptides encompassed by this consensus sequence suitable for inhibiting PKC-δ activity include, without limitation, KKRILHCLGLA (SEQ ID NO:25), RKRILHCLGLA (SEQ ID NO:26), KRRILHCLGLA (SEQ ID NO:27), KKRLLHCLGLA (SEQ ID NO:28), RRRILHCLGLA (SEQ ID NO:29), KRKILHCLGLA (SEQ ID NO:30), RRRLLHCLGLA (SEQ ID NO:31), KKKLLHCLGLA (SEQ ID NO:32). Other peptides encompassed by the above consensus amino acid sequence are also within the scope of the present invention.

A third BVR peptide that inhibits PKC-δ activity and PKC-δ/ERK complex formation and activity has a consensus amino acid sequence of FXFPXF[S/T]G (SEQ ID NO:33), wherein X at amino acid positions 2 and 5 is any amino acid. Peptides comprising this consensus sequence and well as peptides consisting of this consensus sequence are contemplated. Exemplary peptides encompassed by this consensus sequence suitable for inhibiting PKC-δ activity include, without limitation, FGFPAFSG (SEQ ID NO:34), FGFPAFTG (SEQ ID NO:35), FAFPGFSG (SEQ ID NO:36), FAFPGFTG (SEQ ID NO:37), FAFPAFTG (SEQ ID NO:38), FGFPGFSG (SEQ ID NO:39), and FGFPGFTG (SEQ ID NO:40). Other peptides encompassed by the above consensus amino acid sequence are also within the scope of the present invention.

Other BVR peptides that inhibit PKC-δ activity and PKC-δ/ERK complex formation and activity that are suitable for use in the present invention include peptides having a consensus amino acid sequence of LXXLXL (SEQ ID NO:41), LXXLXXXLXL (SEQ ID NO:42), and IXXLXX-LXXLXXXLXL (SEQ ID NO:43), wherein X is any amino acid. Peptides comprising this consensus sequence and well as peptides consisting of this consensus sequence are contemplated.

Inhibition of PKC-δ activity and/or PKC-δ/ERK complex formation and activity has therapeutic benefits for a variety of disease conditions. Specifically, inhibition of PKC-δ and/or PKC-δ/ERK complex formation and activity is desirable for the treatment of neurodegeneration (e.g. Parkinson's disease), ischemia, stroke, inflammation, diabetes, atherogenesis, myocardial infarction and certain autoimmune disorders Inhibiting PKC-δ and/or PKC-δ/ERK complex formation is also a suitable therapeutic target for a number of cancer related conditions including, without limitation, prostate cancer, colon cancer, and head and neck carcinoma. Accordingly, the present invention is directed to a method of treating a PKC-δ or a PKC-δ/ERK complex related condition in a subject that involves administering to the subject having the condition an agent that decreases or inhibits PKC-δ activity or PKC-δ/ERK complex activity under conditions effective to treat the condition. Suitable agents for decreasing or inhibiting PKC-δ and PKC-δ/ERK complex formation and activity include those described supra.

The mode of affecting delivery and cellular uptake of the agents of the present invention to modulate (i.e., increase or decrease) PKC-δ activity or PKC-δ/ERK complex formation and activity, and thereby achieve therapeutic utility, vary depending on the type of therapeutic agent (e.g., a BVR peptide, a nucleic acid encoding a BVR peptide, or an inhibitory BVR nucleic acid molecule) being delivered. For example, nucleic acid molecules encoding a BVR peptide or inhibitory BVR nucleic acid molecules may be incorporated into a gene therapy vector to facilitate delivery. Suitable gene therapy vectors include viral expression vectors such as, adenovirus, adeno-associated virus, retrovirus, lentivirus, or herpes virus.

Adenovirus gene delivery vehicles can be readily prepared and utilized given the disclosure provided in Berkner, "Development of Adenovirus Vectors for the Expression of Heterologous Genes," *Biotechniques* 6:616-29 (1988); Rosenfeld et al., "Adenovirus-mediated Transfer of a Recombinant α1-Antitrypsin Gene to the Lung Epithelium In Vivo," *Science* 252:431-434 (1991), WO 1993/007283 to Curiel et al., WO 1993/006223 to Perricaudet et al., and WO1993/007282 to Curiel et al., which are hereby incorporated by reference in their entirety. Additional types of adenovirus vectors are described in U.S. Pat. No. 6,057,155 to Wickham et al., U.S. Pat. No. 6,033,908 to Bout & Hoeben, U.S. Pat. No. 6,001,557 to Wilson et al., U.S. Pat. No. 5,994,132 to Chamberlain & Kumar-Singh, U.S. Pat. No. 5,981,225 to Kochanek & Schniedner, U.S. Pat. No. 5,885,808 to Spooner & Epenetos, and U.S. Pat. No. 5,871,727 to Curiel, which are hereby incorporated by reference in their entirety.

Adeno-associated viral gene delivery vehicles can be constructed and used to deliver into cells a recombinant gene encoding a desired nucleic acid. The use of adeno-associated viral gene delivery vehicles in vitro is described in Chatterjee et al., "Dual-Target Inhibition of HIV-1 in vitro by Means of an Adeno-associated Virus Antisense Vector," *Science* 258:1485-8 (1992), Walsh et al., "Regulated High Level Expression of a Human γ-Globin Gene Introduced into Erythroid Cells by an Adeno-Associated Virus Vector," *Proc Nat'l Acad Sci USA* 89:7257-61 (1992), Walsh et al., "Phenotypic Correction of Fanconi Anemia in Human Hematopoietic Cells with a Recombinant Adeno-Associated Virus Vector," *J Clin Invest* 94:1440-8 (1994), Flotte et al., "Expression of the Cystic Fibrosis Transmembrane Conductance Regulator from a Novel Adeno-Associated Virus Promoter," *J Biol Chem* 268:3781-90 (1993), Ponnazhagan et al., "Suppression of Human α-Globin Gene Expression Mediated by the Recombinant Adeno-Associated Virus 2-based Antisense Vectors," *J Exp Med* 179:733-8 (1994), Miller et al., "Recombinant Adeno-Associated Virus (rAAV)-Mediated Expression of a Human γ-Globin Gene in Human Progenitor-Derived Erythroid Cells," *Proc Nat'l Acad Sci USA* 91:10183-7 (1994), Einerhand et al., "Regulated High-Level Human β-Globin Gene Expression in Erythroid Cells Following Recombinant Adeno-Associated Virus-Mediated Gene Transfer," *Gene Ther* 2:336-43 (1995), Luo et al., "Adeno-Associated Virus 2-Mediated Gene Transfer and Functional Expression of the Human Granulocyte-Macrophage Colony-Stimulating Factor," *Exp Hematol* 23:1261-7 (1995), and Zhou et al., "Adeno-Associated Virus 2-Mediated Transduction and Erythroid Cell-Specific Expression of a Human β-Globin Gene," *Gene Ther* 3:223-9 (1996), which are hereby incorporated by reference in their entirety. In vivo use of these vehicles is described in Flotte et al., "Stable In Vivo Expression of the Cystic Fibrosis Transmembrane Conductance Regulator with an Adeno-Associated Virus Vector," *Proc Nat'l Acad Sci USA* 90:10613-7 (1993), and Kaplitt et al., "Long-Term Gene Expression and Phenotypic Correction Using Adeno-Associated Virus Vectors in the Mammalian Brain," *Nat Genet* 8:148-54 (1994), which are hereby incorporated by reference in their entirety.

Retroviral vectors which have been modified to form infective transformation systems can also be used to deliver a recombinant gene encoding a BVR peptide product into a target cell. One such type of retroviral vector is disclosed in U.S. Pat. No. 5,849,586 to Kriegler & Perez, which is hereby incorporated by reference in its entirety. Lentivirus vectors can also be utilized, including those described in U.S. Pat. No. 6,790,657 to Arya, U.S. Patent Application Publication No. 2004/0170962 to Kafri et al., and U.S. Patent Application Publication No. 2004/0147026 to Arya, which are hereby incorporated by reference in their entirety.

Regardless of the type of infective transformation system employed, it should be targeted for delivery of the nucleic acid to a specific cell type. For example, for delivery of the nucleic acid into a cluster of cells (e.g., cardiac cells or cancer cells) a high titer of the infective transformation system can be injected directly within the site of those cells so as to enhance the likelihood of cell infection. The infected cells will then express the desired product, in this case BVR, BVR peptide, or an inhibitory BVR nucleic acid molecule to modify PKC-δ or PKC-δ/ERK complex activity present in those cells. The expression system can further contain a promoter to control or regulate the strength and specificity of expression of the therapeutic peptide or nucleic acid molecule in the target tissue or cell.

One of skill in the art can readily select appropriate constitutive mammalian promoters based on their strength as a promoter. As an alternative to constitutive promoters, a mammalian tissue-specific promoter can be utilized. Any of a variety of tissue specific promoters are known in the art and can be selected based upon the tissue or cell type to be treated. For example, in one aspect of the invention it is desirable to increase the level of PKC-δ activity in T-cells for the treatment of lupus. Cell specific targeting to T-cells can be achieved using a T-cell specific promoter such as the CD3δ promoter (Ji et al., "T Cell-Specific Expression of the Murine CD3δ Promoter," *J. Biol. Chem.* 277:47898-47906 (2002), which is hereby incorporated by reference in its entirety). Other tissue and cell specific promoters suitable for use in the present invention include, without limitation, a cardiomyocyte-specific promoter such as the alpha-myosin heavy chain promoter (Akaiwa et al., "Cardiomyocyte-specific Gene Expression Following Recombinant Adeno-associated Viral Vector Transduction," *J. Biol. Chem.* 277 (21):18979-18985 (2002), which is hereby incorporated by reference in its entirety) or a VSMC-specific promoter such as a synthetic promoter containing the aortic preferentially expressed gene-1 (APEG-1) E box motif (Hsieh et al., "Genomic Cloning and Promoter Analysis of Aortic Preferentially Expressed Gene-1: Identification of a Vascular Smooth Muscle-Specific Promoter Mediated by an E Box Motif," *J Biol Chem* 274(20):14344-14351 (1999), which is hereby incorporated by reference in its entirety) can be utilized. Also, a promoter specific for microvascular endothelial cells can be used, such as the promoter of calcitonin receptor-like receptor (CRLR) (Nikitenko et al., "Transcriptional Regulation of the CRLR Gene in Human Microvascular Endothelial Cells by Hypoxia," *FASEB J.* 17(11):1499-501 (2003), which is hereby incorporated by reference in its entirety).

When the desired target cell is a cancer cell, a cancer cell-specific targeting approach is desirable. Suitable cancer cell-specific targeting approaches include the lentivirus-mediated Tet-On inducible system under the control of the matrix metalloproteinase-2 promoter as described by Seo et al., "Induction of Cancer Cell-Specific Death via MMP2 Promoter-Dependent Bax Expression," *BMB Reports* 42(4): 217-222 (2009), which is hereby incorporated by reference in it entirety. Also suitable for targeting cancer-specific cells is the dual promoter system described by Fukazawa et al., "Development of a Cancer-Targeted Tissue-Specific Promoter System," *Can. Res.* 64:363-369 (2004), which is hereby incorporated by reference in its entirety, that combines the human telomerase reverse transcriptase promoter (hTERT) and a tissue specific promoter (e.g., prostate-specific antigen (PSA) or promoter for directing prostate cancer cell specific expression or the PRL-3 protein tyrosine phosphatase promoter for colon cancer cell specific expression) to target expression to cancer cells. Other cancer cell-specific targeting approaches utilizing the hTERT tumor-specific promoter are also suitable for use in the present invention (see, e.g., Fang et al., "Development of Chimeric Gene Regulators for Cancer-Specific Gene Therapy with Both Transcriptional and Translational Targeting," *Mol. Biotechnol.* 45:71-81 (2010), Gu et al., "Tumor-Specific Transgene Expression from the Human Telomerase Reverse Transcriptase Promoter Enables Targeting of the Therapeutic Effects of the Bax Gene to Cancers," *Can. Res.* 60:5359-64 (2000), and Gu et al., "A Novel Single Tetracycline-Regulative Adenoviral Vector for Tumor-Specific Bax Gene Expression and Cell Killing In Vitro and In Vivo," *Oncogene* 21:4757-62 (2002), which are hereby incorporated by reference in their entirety.

Gene expression can be regulated to achieve optimal expression levels and reduce side effects associated with constitutive gene expression. Whether the promoter is tissue-specific or not, the promoter can also be made inducible for purposes of controlling when expression or suppression of the BVR protein or peptide fragment is desired. One of skill in the art can readily select appropriate inducible mammalian promoters from those known in the art. One exemplary inducible promoter includes a Tet-O response element (Farson et al., "A New-Generation Stable Inducible Packaging Cell Line for Lentiviral Vectors," *Hum. Gene Ther* 12(8):981-97 (2001), which is hereby incorporated by reference in its entirety). When used in combination with a tissue-specific promoter, the Tet-O response elements can render a tissue-specific promoter inducible to tetracycline and its derivatives (see e.g., Michalon et al., "Inducible and Neuron-Specific Gene Expression in the Adult Mouse Brain with the rtTA2S-M2 System," *Genesis* 43(4):205-12 (2005), which is hereby incorporated by reference in its entirety).

Another approach that is appropriate for cardiac cell protection against ischemia/reperfusion injury may involve turning on gene expression with the onset of ischemia (hypoxia), so that the gene product is already present during reperfusion. Many transcription factors are modified by hypoxic and oxidative stress. Studies of molecular responses to hypoxia have identified HIF-1α as the master regulator of hypoxia-inducible gene expression. Under hypoxic conditions, HIF-la binds to the hypoxia-responsive element (HRE) in the enhancer region of its target genes and turns on gene transcription. Additionally, reperfusion or reoxygenation after ischemia increases the transactivating ability of NFκB. Genes regulated by NFκB include cytokines and adhesion molecules, which contribute to cell death by promoting inflammatory responses. Several studies indicate that the hypoxic and hyperoxic environment can be used to activate heterologous gene expression driven by HRE and cis-acting consensus sequences of activated NFκB respectively. Accordingly, in one aspect of the invention, at least one HRE is utilized as an enhancer to drive transgene expression in the expression system encoding the desired BVR protein or peptide sequence. Suitable HRE nucleic acid constructs and expression systems are described in U.S. Pat. No. 5,942,434 to Ratcliffe et al., which is hereby incorporated by reference in its entirety. To assure sufficient duration of the transgene expression to achieve myocardial protection during the reperfusion period, a second regulatory element that is activated by oxidative stress such as NFκB responsive element is employed.

Recombinant cell therapy, which is a form of gene therapy, can also be utilized for the delivery of nucleic acid molecule encoding the desired BVR peptides to cardiac tissue for the treatment of coronary disorders. In this approach, a target cell is transfected (i.e., transformed or transduced) with a nucleic acid encoding the BVR protein or peptide and, in turn, the target cell produces the gene product that exerts a therapeutic effect. Target cell transfection can be transient or stable (i.e., the nucleic acid becomes integrated into the genome of the target cell), and the target cell can be heterologous, or preferably autologous to the patient. Once the target cell or cells are producing the BVR protein or modulating peptide, they are administered to the patient.

Therapeutic BVR peptides or nucleic acid molecule encoding the peptides can also be delivered to the target cell (e.g., cardiac cells or cancer cells) using liposomes. Basically, this involves providing a liposome which encapsulates the BVR peptide or nucleic acid to be delivered, and then contacting the target cell with the liposome under conditions effective for delivery of the peptide or nucleic acid into the cell.

Liposomes are vesicles comprised of one or more concentrically ordered lipid bilayers which encapsulate an aqueous phase. They are normally not leaky, but becomes leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug, in this case the BVR peptide or nucleic acid at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be regulated.

In contrast to passive drug release, active drug release involves using an agent to induce a permeability change in the liposome vesicle. Liposome membranes can be constructed so that they become destabilized when the environment becomes acidic near the liposome membrane (see e.g., Wang et al., "pH-Sensitive Immunoliposomes Mediate Target-Cell-Specific Delivery and Controlled Expression of a Foreign Gene in Mouse," *Proc Natl Acad Sci USA* 84:7851 (1987), which is hereby incorporated by reference in its entirety). When liposomes are endocytosed by a target cell, for example, they can be routed to acidic endosomes which will destabilize the liposome and result in drug release. Alternatively, the liposome membrane can be chemically modified such that an enzyme is placed as a coating on the membrane which slowly destabilizes the liposome. The liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., "Diffusion of Univalent Ions Across the Lamellae of Swollen Phospholipids," *J Mol Biol* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat.

No. 5,059,421 to Loughrey et al., which are hereby incorporated by reference in their entirety.

In a preferred embodiment of the present invention, the liposome is conjugated to an antibody targeting the liposome to a desired target cell, e.g., a cardiac cell or cancer cell. For example, to target the lipsome to a cancer cell the liposome may be conjugated to an anti-C3B(I) antibody as disclosed by U.S. Pat. No. 6,572,856 to Taylor et al., an alphafe to protein receptor as disclosed by U.S. Pat. No. 6,514,685 to Moro, or the monoclonal GAH antibody as disclosed by U.S. Pat. No. 5,837,845 to Hosokawa, which are hereby incorporated by reference in their entirety. For targeting the liposome to cardiac cells, the lipsome may be conjugated to an antibody recognizing elastin microfibril interfacer (EMILIN2) (Van Hoof et al., "Identification of Cell Surface for Antibody-Based Selection of Human Embryonic Stem Cell-Derived Cardiomyocytes," *J Proteom Res* 9:1610-18 (2010), which is hereby incorporated by reference in its entirety, cardiac troponin I, connexin-43, or any cardiac cell-surface membrane receptor that is known in the art.

Like liposomes, micelles have also been used in the art for drug delivery. A number of different micelle formulations have been described in the literature for use in delivery proteins or polypeptides, and others have been described which are suitable for delivery of nucleic acids. Any suitable micelle formulations can be adapted for delivery of the therapeutic protein, peptide, or nucleic acid of the present invention. Exemplary micelles include without limitation those described, e.g., in U.S. Pat. No. 6,210,717 to Choi et al.; and U.S. Pat. No. 6,835,718 to Kosak, each of which is hereby incorporated by reference in its entirety.

An alternative approach for delivery of peptides or nucleic acids involves the conjugation of the desired therapeutic agent to a polymer that is stabilized to avoid enzymatic degradation of the conjugated protein or polypeptide. Conjugated proteins or peptides of this type are described in U.S. Pat. No. 5,681,811 to Ekwuribe, which is hereby incorporated by reference in its entirety. Nucleic acid conjugates are described in U.S. Pat. No. 6,528,631 to Cook et al., U.S. Pat. No. 6,335,434 to Guzaev et al., U.S. Pat. No. 6,235,886 to Manoharan et al., U.S. Pat. No. 6,153,737 to Manoharan et al., U.S. Pat. No. 5,214,136 to Lin et al., or U.S. Pat. No. 5,138,045 to Cook et al., each of which is hereby incorporated by reference in its entirety.

Yet another approach for delivery of proteins or polypeptides involves preparation of chimeric proteins according to U.S. Pat. No. 5,817,789 to Heartlein et al., which is hereby incorporated by reference in its entirety. The chimeric protein can include a targeting domain and a BVR peptide. The targeting domain can direct cellular uptake of the peptide of the present invention, direct the peptide to a specific cell-type, or direct intracellular localization once internalized. Thus, when the chimeric protein is delivered intravenously or otherwise introduced into blood or lymph, the chimeric protein will adsorb to the targeted cell, and the targeted cell will internalize the chimeric protein.

Chimeric proteins of the present invention may contain a cell penetrating peptide (CPP) to promote cellular uptake of the peptides of the present invention. CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, and M918, are suitable targeting moieties for use in the present invention and are well known in the art (see Stewart et al., "Cell-Penetrating Peptides as Delivery Vehicles for Biology and Medicine," *Organic Biomolecular Chem* 6:2242-2255 (2008), which is hereby incorporated by reference in its entirety). Additionally, methods of making CPP are described in U.S. Patent Application Publication No. 20080234183 to Hallbrink et al., which is hereby incorporated by reference in its entirety.

Alternatively, the cellular uptake of the peptides may be facilitated by generating a chimeric protein which includes an "importation competent" signal peptide as disclosed by U.S. Pat. No. 6,043,339 to Lin et al., which is hereby incorporated by reference in its entirety. An importation competent signal peptides is generally about 10 to about 50 amino acid residues in length, typically hydrophobic residues, that render a peptide capable of penetrating through the cell membrane from outside the cell to the interior of the cell. An exemplary importation competent signal peptide includes the signal peptide from Kaposi fibroblast growth factor (see U.S. Pat. No. 6,043,339 to Lin et al., which is hereby incorporated by reference in its entirety). Other suitable peptide sequences can be selected from the SIGPEP database (see von Heijne G., "SIGPEP: A Sequence Database for Secretory Signal Peptides," *Protein Seq. Data Anal.* 1(1):41-42 (1987), which is hereby incorporated by reference in its entirety).

In yet another embodiment, the chimeric protein of the present invention contains a signal peptide sequence capable of targeting the peptide to a particular tissue or cell type. The signaling peptide can include at least a portion of a ligand binding protein. The ligand domain is specific for receptors located on a cellular target, e.g., cancer cells (e.g., prostate or colon cancer cells), neuronal cells, cardiocytes, leukocytes (e.g., T-cells), and fibroblasts. Suitable ligand binding proteins include high-affinity antibody fragments (e.g., Fab, Fab' and F(ab')$_2$), single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the modified peptide is delivered intravenously or otherwise introduced into blood or lymph, the peptide will adsorb to the targeted cell, and the targeted cell will internalize the peptide. For example, if the target cell is a cancer cell, the peptide may be conjugated to an anti-C3B(I) antibody as disclosed by U.S. Pat. No. 6,572,856 to Taylor et al., which is hereby incorporated by reference in its entirety. Alternatively, the peptide may be conjugated to an alphafe to protein receptor as disclosed by U.S. Pat. No. 6,514,685 to Moro, or to a monoclonal GAH antibody as disclosed by U.S. Pat. No. 5,837,845 to Hosokawa, which are hereby incorporated by reference in their entirety. For targeting an peptide to a cardiac cell, the peptide may be conjugated to an antibody recognizing elastin microfibril interfacer (EMILIN2) (Van Hoof et al., "Identification of Cell Surface for Antibody-Based Selection of Human Embryonic Stem Cell-Derived Cardiomyocytes," *J Proteom Res* 9:1610-18 (2010), which is hereby incorporated by reference in its entirety), cardiac troponin I, connexin-43, or any cardiac cell-surface membrane receptor that is known in the art. For targeting a peptide to a hepatic cell, the signaling peptide may include a ligand domain specific to the hepatocyte-specific asialoglycoprotein receptor. Methods of preparing such chimeric proteins and peptides are described in U.S. Pat. No. 5,817,789 to Heartlein et al., which is hereby incorporated by reference in its entirety.

Other suitable chimeric proteins contain a transport peptide that directs intracellular compartmentalization of the target peptide once it is internalized by a target cell or tissue. For example, if the protein activity or protein-protein interaction that is sought to be inhibited occurs in the endoplasmic reticulum (ER), the peptide of the present invention can be conjugated to an ER transport peptide sequence. A number of such signal peptides are known in the art, including the signal peptide MMSFVSLLLVGILFYATE-AEQLTKCEVFQ (SEQ ID NO: 64). Other suitable ER signal peptides include the N-terminus endoplasmic reticulum targeting sequence of the enzyme 17β-hydroxysteroid dehydrogenase type 11 (Horiguchi et al., "Identification and Characterization of the ER/Lipid Droplet-Targeting Sequence in 17β-hydroxysteroid Dehydrogenase Type 11," *Arch. Biochem. Biophys.* 479(2):121-30 (2008), which is hereby incorporated by reference in its entirety), or any of the ER signaling peptides (including the nucleic acid sequences encoding the ER signal peptides) disclosed in U.S. Patent Publication No. 20080250515 to Reed et al., which is hereby incorporated by reference in its entirety. Additionally, the peptide of the present invention can contain an ER retention signal, such as the retention signal KEDL (SEQ ID NO: 65). Methods of modifying the peptides of the present invention to incorporate transport peptides for localization of the peptides to the ER can be carried out as described in U.S. Patent Publication No. 20080250515 to Reed et al., which is hereby incorporated by reference in its entirety.

The peptides of the present invention can also be targeted to the nucleus by generating a chimeric protein that includes a nuclear localization transport signal. Suitable nuclear transport peptide sequences are known in the art, including the nuclear transport peptide PPKKKRKV (SEQ ID NO:66). Other nuclear localization transport signals include, for example, the nuclear localization sequence of acidic fibroblast growth factor and the nuclear localization sequence of the transcription factor NF-KB p50 as disclosed by U.S. Pat. No. 6,043,339 to Lin et al., which is hereby incorporated by reference in its entirety. Other nuclear localization peptide sequences known in the art are also suitable for use in the accordance with this aspect of the invention.

Suitable transport peptide sequences for targeting the peptides of the present invention to the mitochondria include MLSLRQSIRFFKPATRTLCSSRYLL (SEQ ID NO: 67). Other suitable transport peptide sequences suitable for selectively targeting the peptides of the present invention to the mitochondria are disclosed in U.S. Published Patent Application No. 20070161544 to Wipf, which is hereby incorporated by reference in its entirety.

Another aspect of the present invention relates to isolated BVR peptides, including any of the peptides described above, and pharmaceutical compositions containing an isolated peptide of the invention and a pharmaceutical carrier.

The isolated peptides of the present invention may be prepared using standard methods of synthesis known in the art, including solid phase peptide synthesis (Fmoc or Boc strategies) or solution phase peptide synthesis. Alternatively, peptides of the present invention may be prepared using recombinant expression systems.

For recombinant protein or peptide synthesis, subclones of a gene encoding a known BVR can be produced using conventional molecular genetic manipulation for subcloning gene fragments, such as described by Joseph Sambrook et al., MOLECULAR CLONING: A LABORATORY MANUAL (Cold Springs Harbor 1989) and Ausubel et al., CURRENT PROTOCOLS IN MOLECULAR BIOLOGY (John Wiley & Sons 1999), each of which is hereby incorporated by reference in its entirety. The subclones then are expressed in vitro or in vivo in bacterial cells to yield a smaller protein or polypeptide that can be tested for a particular activity, e.g., binding and inhibiting PKC-δ as discussed in the Examples.

In another approach, based on knowledge of the primary structure of the protein, fragments of a BVR gene may be synthesized using PCR with specific sets of primers chosen to represent particular portions of the protein (Erlich et al., "Recent Advances in the Polymerase Chain Reaction," *Science* 252:1643-51 (1991), which is hereby incorporated by reference in its entirety). These can then be cloned into an appropriate vector for expression of a truncated protein or polypeptide from bacterial cells. For example, oligomers of at least about 15 to 20 nucleotides in length can be selected from the nucleic acid molecule of SEQ ID NO: 2 for use as primers.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989), which is hereby incorporated by reference in its entirety. U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize peptide production. For the purposes of expressing a cloned nucleic acid sequence encoding a desired peptide, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize peptide production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated peptide of the present invention, a promoter molecule of choice, including, without limitation, enhancers, and leader sequences, a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999), and U.S. Pat. No. 4,237,224 to Cohen and Boyer, which are hereby incorporated by reference in their entirety.

Once the nucleic acid molecule encoding the peptide has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purification of peptide produced via recombinant methods may be achieved by several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Pharmaceutical compositions containing the isolated BVR peptides of the present invention also contain pharmaceutically or physiologically acceptable carriers, excipients, or stabilizers. The pharmaceutical compositions can be in solid or liquid form such as, tablets, capsules, powders, solutions, suspensions, or emulsions, and can be administered orally, parenterally, subcutaneously, intravenously, intramuscularly, intraperitoneally, by intranasal instillation, by intracavitary or intravesical instillation, intraocularly, intraarterially, intralesionally, by application to mucous membranes, such as, that of the nose, throat, and bronchial tubes, or by transdermal delivery. For most therapeutic purposes, peptides or nucleic acids can be administered intravenously or parenterally.

For injectable dosages, solutions or suspensions of the BVR peptides or nucleic acids can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the peptides or nucleic acids in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Other delivery systems that are known in the art can be modified for delivery of the therapeutic proteins, peptides, or nucleic acid molecules described supra.

Another aspect of the present invention relates to a method of diagnosing a PKC-δ related condition in a subject. This method includes obtaining a sample from the subject, contacting the sample from the subject with a BVR peptide under conditions effective for PKC-δ mediated BVR peptide phosphorylation, and detecting the level of BVR peptide phosphorylation. The detected level of BVR peptide phosphorylation is compared with a reference level of BVR peptide phosphorylation and the PKC-δ related condition is diagnosed in a subject based on said comparing.

A suitable reference level of BVR peptide phosphorylation is the level of PKC-δ mediated BVR peptide phosphorylation in a sample obtained from a non-disease tissue, preferably, but not necessarily, derived from the same subject that is being diagnosed. In a preferred embodiment, the reference level of BVR peptide phosphorylation is obtained from a sample representing the same tissue or cell type as the sample being used for the diagnosis. The reference level of BVR peptide phosphorylation is the level of PKC-δ mediated BVR peptide phosphorylation in a normal, non-disease, sample from the subject. As an alternative, a reference level can be obtained from a non-disease tissue from a population of individuals.

In accordance with this aspect of the present invention detecting a level of BVR peptide phosphorylation in a test sample that is lower than a reference level of BVR peptide phosphorylation indicates that the subject has a condition caused by or modulated by insufficient PKC-δ activity or insufficient PKC-δ/ERK complex formation. Such conditions include, but are not limited, to certain autoimmune disorders (e.g., lupus, arthritis, and Good pasture syndrome), inflammatory disease, (e.g., chronic inflammatory conditions), and cytostasis.

Alternatively, when the detected level of BVR peptide phosphorylation in a sample from a subject is higher than a reference level of BVR peptide phosphorylation, a condition caused by or modulated excessive PKC-δ activity is diagnosed. Conditions involving excessive PKC-δ activity include neurodegeneration, cancer (e.g., colon cancer, prostate cancer, head and neck carcinoma), ischemia, inflammation, diabetes, atherogenesis, myocardial infarction and certain autoimmune disorders.

A BVR peptide fragment that is a substrate for PKC-δ phosphorylation and is suitable for use in diagnosing a PKC-δ mediated condition has a consensus amino acid sequence of GL[K/R][K/R]N[K/R][F/Y/W]L[S/T][F/Y/W][K/R/H][F/Y/W][K/R][S/T] (SEQ ID NO: 44). An exemplary BVR peptide encompassed by this BVR consensus sequence comprises an amino acid sequence of GLKRNRYLSFHFKS (SEQ ID NO: 45). Another BVR peptide fragment that is a suitable substrate for PKC-δ phosphorylation comprises an amino acid sequence of SX[R/K] (SEQ ID NO: 46) or STX[R/K] (SEQ ID NO: 47), wherein X is any amino acid residue.

In addition to diagnosing a PKC-δ related condition in a subject, the above described method can also be used to monitor the progression of a PKC-δ related condition or monitor the treatment of a PKC-δ related condition. In either such method the level of PKC-δ mediated BVR peptide phosphorylation that is detected is compared to the level of PKC-δ mediated BVR peptide phosphorylation that is detected from a similar sample from the same subject that is obtained at either an earlier of later timepoint. When monitoring the treatment of a PKC-δ related condition, the level of PKC-δ mediated BVR peptide phosphorylation is determined prior to and after administering a therapeutic treatment. A change in the level of PKC-δ mediated BVR peptide phosphorylation following treatment indicates the treatment is having a beneficial effect on the PKC-δ related condition in the subject.

EXAMPLES

The following examples illustrate various methods for compositions in the treatment method of the invention. The examples are intended to illustrate, but in no way limit, the scope of the invention.

Materials and Methods for Examples 1-6

Materials: Recombinant PKC-δ, Rottlerin, and PMA were obtained from Calbiochem (San Diego, Calif.). The specific PKC-δ peptide substrate was purchased from Biomol (Plymouth Meeting, Pa.). DTT and adenosine 5'-triphosphate (ATP) were obtained from Sigma-Aldrich (St. Louis, Mo.). MBP, phosphatidylserine and diacylglycerol mix were from Millipore (Temecula, Calif.). hBVR-derived peptides (in both unmodified and N-myristoylated forms) were synthesized by EZBiolab (Westfield, Ind.). [γ-$^{32}$P]-ATP and [$^{32}$P]-H$_3$PO$_4$ (carrier and HCl free) were from Perkin-Elmer (Wellesley, Mass.). Polyclonal anti-PKC-δ antibodies were from Cell Signaling. Anti-human hBVR polyclonal antibodies were obtained as described before (Maines et al., "Purification and Characterization of Human Biliverdin Reductase," Arch. Biochem. Biophys. 300: 320-326 (1993), which is hereby incorporated by reference in its entirety).

Plasmids and mutants: Plasmids encoding the hBVR mutants: V$^{11-14}$+G$^{17}$→A (kinase-dead) and V$^{11-14}$→A, were made by site directed mutagenesis of wild-type hBVR cDNA clones (Maines et al., "Human Biliverdin IXalpha Reductase is a Zinc-Metalloprotein. Characterization of Purified and Escherichia Coli Expressed Enzymes," Eur. J. Biochem. 235:372-381 (1996), which is hereby incorporated by reference in its entirety). Mutants were made both in pGEX-4T2 (for expression in E. coli) and in pcDNA3 for mammalian expression. The plasmids were verified by sequencing, to ensure both the integrity of the insert and its being in the correct reading frame. The pEGFP-hBVR plasmid has been described elsewhere (Kravets et al., "Biliverdin Reductase, A Novel Regulator for Induction of Activating Transcription Factor-2 and Heme Oxygenase-1," J. Biol. Chem. 279:19916-19923 (2004), which is hereby incorporated by reference in its entirety). The human PKC-δ open reading frame was also cloned in the same vectors, using PCR-amplification products derived from a human brain cDNA library (Invitrogen, Carlsbad, Calif.). A kinase inactive human PKC-δ sequence (K$^{378}$R, Li et al., "Characterization of A Protein Kinase C-delta (PKC-delta) ATP Binding Mutant. An Inactive Enzyme That Competitively Inhibits Wild Type PKC-delta Enzymatic Activity," J. Biol. Chem. 270:8311-8318 (1995), which is hereby incorporated by reference in its entirety) was constructed by site-directed mutagenesis. Similarly, a constitutively active PKC-δ was constructed by mutagenesis to delete aa 151-160 in the pseudo-substrate loop (Zhao et al., "The Expression of Constitutively Active Isotypes of Protein Kinase C to Investigate Preconditioning," J. Biol. Chem. 273:23072-23079 (1998), which is hereby incorporated by reference in its entirety). A plasmid to express PKC-δ as a red fluorescent fusion protein was constructed by inserting the open reading frame of PKC-δ into the plasmid pDsRed2-C1 (Clontech, Mountain View, Calif.).

Cell Culture, infection, transfection, GST pull-down and co-immunoprecipitation: HEK 293A cells were grown in Dulbecco's Modified Eagle Medium (Invitrogen) containing 10% fetal bovine serum and 1% penicillin-G/streptomycin for 24 h or until the cells reached 70% confluency. Depending on the experiment, cells were subsequently transfected with up to 5 μg of pcDNA3-hBVR or pcDNA3-PKC-δ plasmid using Transfectin Lipid Reagent (Bio-Rad, Hercules, Calif.) in 10 cm plates. Western blotting determined overexpression of hBVR or PKC-δ. To prepare si-hBVR or sc-hBVR (containing a randomized variant of the sihBVR sequence), pSuper-Retro-si-hBVR (Miralem et al., "Small Interference RNA-Mediated Gene Silencing of Human Biliverdin Reductase, But Not That of Heme Oxygenase-1, Attenuates Arsenite-Mediated Induction of the Oxygenase and Increases Apoptosis in 293A Kidney Cells," J. Biol. Chem. 280:17084-17092 (2005), which is hereby incorporated by reference in its entirety) or sc-hBVR, respectively, were introduced into 293A cells for packaging, and the si-hBVR or sc-hBVR retrovirus were titrated using NIH3T3 cells. 293A cells were infected with 4 plaque-forming units/cell to inhibit hBVR synthesis (Miralem et al., "Small Interference RNA-Mediated Gene Silencing of Human Biliverdin Reductase, But Not That of Heme Oxygenase-1, Attenuates Arsenite-Mediated Induction of the Oxygenase and Increases Apoptosis in 293A Kidney Cells," J. Biol. Chem. 280:17084-17092 (2005), which is hereby incorporated by reference in its entirety). For GST pull-down, pcDNA3-PKC-δ was used to express PKC-δ. Prior to treatment with 100 nM PMA, the cells were serum-starved in growth medium containing 0.1% FBS for 24 h. After treatment, they were lysed in RIPA buffer. Cell lysate was incubated with 10 μg GST-hBVR fusion protein or GST immobilized on GSH-agarose beads (Amersham, Piscataway N.J.) at 4° C. for 2 h. The beads were washed three times and boiled in Laemmli buffer to release the bound proteins. Proteins were separated by SDS-page and detected by immunoblotting using anti-PKC-δ antibodies.

Immunoprecipitation was performed on cell lysates prepared as described previously (Lerner-Marmarosh et al., "Regulation of TNF-alpha-Activated PKC-zeta Signaling By the Human Biliverdin Reductase: Identification of Activating and Inhibitory Domains of the Reductase," *FASEB J.* 21:3949-3962 (2007), which is hereby incorporated by reference in its entirety). Immunoprecipitates were separated by SDS PAGE, and the proteins blotted to nitrocellulose membrane. The antibodies used for precipitation and for probing the membranes are as described in the specific figure legends.

Measurement of PKC-δ activity: In vitro kinase activity assays were performed with active recombinant human PKC-δ kinase (as a GST fusion protein). PKC-δ assay in vitro was performed using 5 ng purified enzyme in a 50 μl assay containing 50 mM HEPES pH 7.4, 10 mM $MgCl_2$, 0.2 mM DTT, sonicated lipid activators (0.5 μg phosphatidylserine and 0.05 μg diacylglycerol) or lipid activators plus PMA (as indicated in appropriate experiments) and PKC-δ substrates. The reaction was started by the addition of 50 μM ATP labeled with 5 μCi [$\gamma$-$^{32}$P]-ATP. Incubation was performed for 15 min at 30° C., unless otherwise stated. The reaction was terminated on ice, either by the addition of Laemmli buffer followed by SDS-PAGE, transferred to PVDF membrane, and autoradiography, or by the addition of 1 volume 10% phosphoric acid for p81 transfer as described below. For autophosphorylation of PKC-δ 20 μM ATP was used to start the 40-min reaction.

When hBVR or its mutants were tested for their effect on PKC-δ activity, they were pre-incubated for 5 min at room temperature with the PKC prior to substrate addition. The hBVR-derived peptides were used at concentrations indicated in appropriate figures.

When hBVR or its mutants were assayed as the sole substrates for PKC, the incubation conditions were as described above and the incubation was for 40 min at 30° C. unless specified otherwise. The reaction was terminated by the addition of Laemmli buffer, and the reaction products were detected by SDS-PAGE, transfer to PVDF membrane, and autoradiography.

The PKC-δ activity assay in situ was performed by a modification of procedures detailed by Williams and Schrier (Williams et al., Glucose-Induced Protein Kinase C Activity Regulates Arachidonic Acid Release and Eicosanoid Production by Cultured Glomerular Mesangial Cells," *J. Clin. Invest.* 92:2889-2896 (1993), which is hereby incorporated by reference in its entirety). Cells were seeded into 48-well plates and transfected with 0.1 μg/well pcDNA3-hBVR. After 24 h, the medium was replaced with a starvation medium (0.1% serum) and incubation continued for another 24 h to synchronize cells. In some wells, PKC inhibitor Rottlerin (20 μM) was added 30 min before addition of PMA (100 nM) for 15 min. In some wells, hBVR-derived peptides were introduced to cells in their myristoylated form. Cells were washed with medium and incubated for 10 min at 30° C. in 50 μl of kinase assay buffer (137 mM NaCl, 5.4 mM KCl, 10 mM $MgCl_2$, 0.3 mM $Na_2HPO_4$, 0.4 mM $KH_2PO_4$, 25 mM β-glycerophosphate, 5.5 mM D-glucose, 5 mM EGTA, 1 mM $CaCl_2$, 20 mM HEPES (pH 7.2), 50 μg/ml digitonin, 120 μg/ml of PKC-δ specific substrate (AR-RKRKGSFFGG; SEQ ID NO: 52) and 100 μM ATP labeled with 10 μCi/ml [$\gamma$-$^{32}$P]-ATP). The reaction was stopped with the addition of 25 μl of ice-cold 30% (wt/vol) TCA. The TCA-soluble fraction samples were transferred to p81 phospho-cellulose filters. After 15 min at room temperature, the filters were washed three times in 75 mM phosphoric acid, once in 2.75 mM sodium phosphate (pH 7.5) and once with acetone before liquid scintillation counting. Kinase activity was normalized to protein content.

Measurement of PKC-β and PKC-ζ activities. Recombinant PKC-βII (Calbiochem) was assayed in vitro in 20 mM HEPES pH 7.2, 15 mM $MgCl_2$, 0.2 mM $CaCl_2$, 1 mM DTT, 25 mM β-glycerophosphate, 50 μg/ml phosphatidylserine and 5 μg/ml diacylglycerol, using 12.5 μM MBP as substrate, using 5 ng of enzyme per 50 μl reaction. 100 μM ATP (containing [$\gamma$$^{32}$P]-ATP (as above) was used to start the reaction, and incorporation was determined using p81 filter binding (Maines et al., "Human Biliverdin Reductase: A Previously Unknown Activator of Protein Kinase C-βII," *J. Biol. Chem.* 282:8110-8122 (2007), which is hereby incorporated by reference in its entirety). Similarly, recombinant PKC-ζ(Millipore) was assayed in 20 mM MOPS pH 7.2, 15 mM $MgCl_2$, 0.2 mM EDTA, with 12.5 μM MBP as substrate, again using 5 ng of enzyme per 50 μl reaction (Lerner-Marmarosh et al., "Regulation of TNF-alpha-Activated PKC-zeta Signaling By the Human Biliverdin Reductase: Identification of Activating and Inhibitory Domains of the Reductase," FASEB J. 21:3949-3962 (2007), which is hereby incorporated by reference in its entirety). Otherwise, reaction conditions were as for PKC-βII.

hBVR kinase assay: Kinase activity of hBVR was assayed as described earlier (Lerner-Marmarosh et al., "Human Biliverdin Reductase: A Member of the Insulin Receptor Substrate Family With Serine/Threonine/Tyrosine Kinase Activity," *Proc. Natl. Acad. Sci. U.S.A.* 102:7109-7114 (2005), which is hereby incorporated by reference in its entirety). hBVR was incubated at 30° C. in 50 μl reaction mixture containing 50 mM HEPES (pH 8.4), 30 mM $MnCl_2$, 0.2 mM DTT, 10 μM ATP labeled with 10 μCi of [$\gamma$-$^{32}$P]ATP, and PKC-δ for 30 min.

Measurement of hBVR reductase activity: hBVR activity was measured at pH 6.7 using NADH as the cofactor as described (Huang et al., "Selective Subcellular Redistributions of Protein Kinase C Isoforms by Chemical Hypoxia," *J. Neurosci. Res.* 56:668-678 (1999), which is hereby incorporated by reference in its entirety). The rate of reduction of biliverdin to bilirubin was determined by the increase in absorbance at 450 nm at 25° C. Specific activity is expressed as nmol of bilirubin/min/mg of protein.

Confocal microscopy: Experimental protocols were based on those described by Edwards et al., "Carboxyl-Terminal Phosphorylation Regulates the Function and Subcellular Localization of Protein Kinase C betall," *J. Biol. Chem.* 274:6461-6468 (1999), which is hereby incorporated by reference in its entirety. 293A cells were grown in a chamber slide system (Nalge-Nunc International Corp., Naperville, Ill.). Cells were transfected with pEGFP-hBVR and/or the plasmid expressing Ds2-Red-PKC-δ fusion protein. After a 24 h starvation period, cells were fixed for 10 min in 4% Para-formaldehyde in PBS and permeabilized with 1% Triton X-100 in PBS. The cells were mounted with Vectashield (Vector Laboratories, Inc. Burlingame, Calif.), containing DAPI to visualize the nuclei. Non-transfected cells were permeabilized as above, treated with 1:150 dilution of polyclonal anti-PKC-δ antibodies, washed, blocked, and then treated with polyclonal anti-hBVR antibodies. The PBS-washed cells were then treated with Rhodamine-red-conjugated donkey anti-rabbit IgG antibodies (Jackson ImmunoResearch, West Grove, Pa.) for 30 min, followed by mounting. A Leica TCS SP (model DMRE) confocal microscope was used (Maines et al., "Human Biliverdin Reductase: A Previously Unknown Activator of Protein Kinase C-βII," *J. Biol. Chem.* 282:8110-8122 (2007), which is hereby incorporated by reference in its entirety).

Statistical Analysis: Data as presented in bar graphs are the means with standard deviations of three experiments, each with triplicate samples. Data were analyzed by one-way ANOVA from which Student's t was calculated for all sample pairs. Differences within experiments were considered significant if p≤0.05. Experiments were repeated three times unless otherwise indicated. Differences between experiments were not significant. Fitting data to the Michaelis-Menten equation used Prism 3.0 software (GraphPad, San Diego, Calif.).

Example 1 hBVR Activates PKC-δ

Since hBVR and PKC-δ have a common list of extracellular stimuli (Kapitulnik et al., "Pleiotropic Functions of Biliverdin Reductase: Cellular Signaling and Generation of Cytoprotective and Cytotoxic Bilirubin," *Trends Pharmacol. Sci.* 30:129-137 (2009), Jackson et al., "The Enigmatic Protein Kinase C delta: Complex Roles in Cell Proliferation and Survival," *FASEB J.* 18:627-636 (2004), Gschwendt, M., "Protein kinase C Delta," *Eur. J. Biochem.* 259:555-564 (1999), Stempka et al., "Requirements of Protein Kinase cdelta for Catalytic Function. Role of Glutamic Acid 500 and Autophosphorylation on Serine 643," *J. Biol. Chem.* 274:8886-8892 (1999), Wang et al., "Differential Localization of Protein Kinase C Delta by Phorbol Esters and Related Compounds Using A Fusion Protein With Green Fluorescent Protein," *J. Biol. Chem.* 274:37233-37239 (1999), which are hereby incorporated by reference in their entirety) it was of interest to examine whether hBVR and this kinase, a member of novel group of PKCs, interact. The kinase: kinase interaction between hBVR and PKC-δ was examined in vitro. When analyzing PKC-δ kinase activity, conditions optimal for kinase assay were pH 7.4 with $Mg^{2+}$, while the hBVR kinase assay was carried out at pH 8.4 with $Mn^{2+}$ (in the absence of $Mg^{2+}$). Two forms of purified hBVR, with or without a GST tag, were used in the initial experiments. Both gave identical results, demonstrating that the GST tag does not affect hBVR phosphorylation by PKC-δ. Because the GST-hBVR fusion protein is more stable, the experiments described below were conducted using this preparation.

Figure 1A:
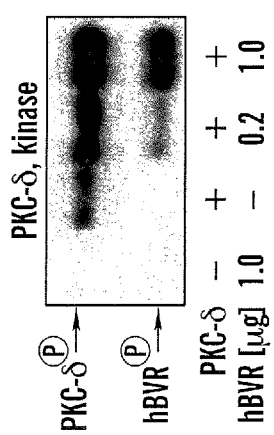
Figure 1G:
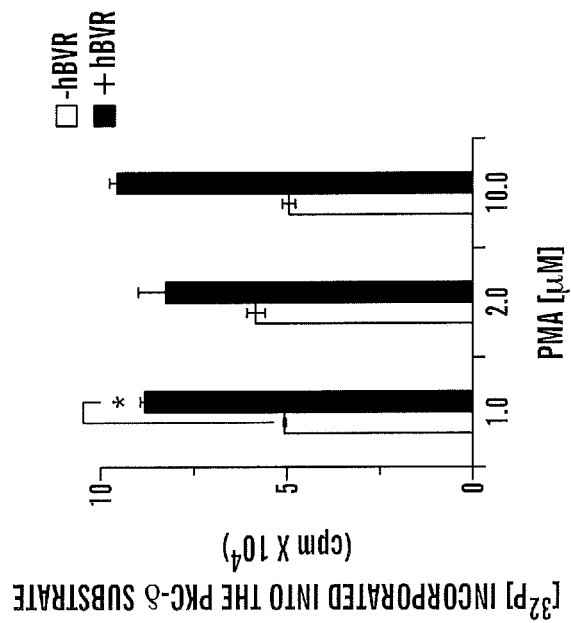
Figure 1F:
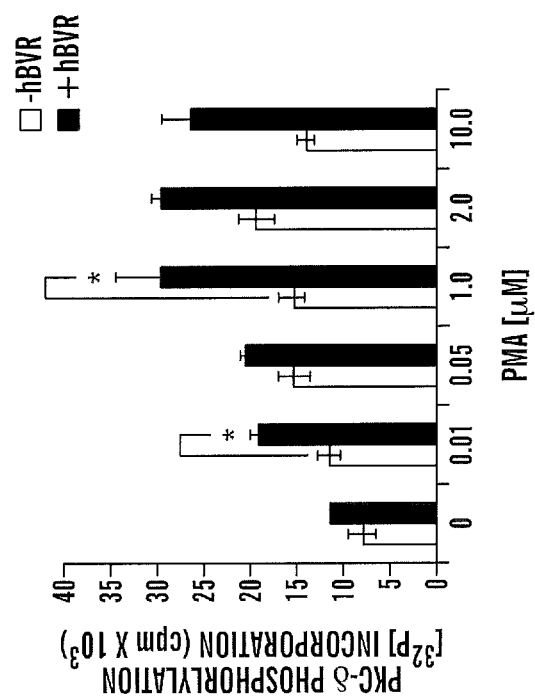

The presence of purified *E. coli* expressed hBVR in a PKC-δ kinase assay system resulted in phosphorylation of hBVR concomitant with an enhanced PKC-δ autophosphorylation (FIG. 1A), and increased kinase activity toward the substrate, MBP (FIG. 1B). To examine whether ATP binding to hBVR is involved in this increase in PKC autophosphorylation, a kinase deficient mutant of hBVR was used; the protein was generated by replacing glycine in the ATP/adenine binding domain (GXGXXG; SEQ ID NO: 50) (Benes et al., "Modulation of PKC-delta Tyrosine Phosphorylation and Activity in Salivary and PC-12 Cells by Src Kinases," *Am. J. Physiol. Cell Physiol.* 280:C1498-1510 (2001), Hoekstra et al., "Budding and Fission Yeast Casein Kinase Isoforms Have Dual-Specificity Protein Kinase Activity," *Mol. Biol. Cell* 5:877-886 (1994), which are hereby incorporated by reference in their entirety), and replacing flanking in the chain flanking the four valines with alanine. This engineered protein is kinase-dead (Lerner-Marmarosh et al., "Regulation of TNF-alpha-Activated PKC-zeta Signaling By the Human Biliverdin Reductase: Identification of Activating and Inhibitory Domains of the Reductase," *FASEB J.* 21:3949-3962 (2007), which is hereby incorporated by reference in its entirety). The wt-hBVR and hBVR-$V^{11-14}$→A mutant were used as controls; $V^{11-14}$ is a site of interaction with PKC-βII (Maines et al., "Human Biliverdin Reductase: A Previously Unknown Activator of Protein Kinase C-βII," *J. Biol. Chem.* 282:8110-8122 (2007), which is hereby incorporated by reference in its entirety). The findings are shown in FIG. 1C. As noted, the three different forms of hBVR activated the PKC and were phosphorylated by the kinase, demonstrating that hBVR kinase competency is not necessary for activation of PKC-δ. The observation with hBVR-$V^{11-14}$→A that its replacement was inconsequential to both activation of the PKC and phosphorylation of hBVR indicates that the interaction between PKC-δ and hBVR must occur at other segments of hBVR. To confirm that phosphorylation of hBVR in the PKC kinase assay system is not a result of autophosphorylation, the kinase-dead, $K^{378}R$, mutant of PKC-δ was used. As shown in FIG. 1D, only active PKC-δ was able to phosphorylate hBVR, and, therefore, data obtained under these conditions are results of PKC kinase activity. The data also confirm that the mutant PKC protein was indeed kinase-deficient. Collectively, these data demonstrate that the ability to autophosphorylate is a prerequisite to PKC-δ activation by hBVR. Since both proteins are kinases, the question whether there is reciprocal phosphorylation of PKC-δ by hBVR was examined. By using different assay conditions, it was demonstrated (FIG. 1E) that there was robust auto-phosphorylation of hBVR under assay conditions optimal for hBVR kinase activity, but PKC-δ was not an effective substrate for wt-hBVR. In the next experiment, it was examined whether PKC-δ activation in the presence of hBVR is merely a reflection of its substituting for PMA. This possibility was dismissed by the findings shown in FIGS. 1F and 1G, analyzing autophosphorylation of PKC-δ and its substrate phosphorylation, respectively. As shown, a several fold increase in the concentration of the phorbol ester did not increase PKC activity to the same level as observed with hBVR. A similar observation has been made in intact cells.

Example 2 hBVR and PKC-δ Protein:Protein Interaction

To test whether BVR and PKC-δ bind to each other, cells lysates overexpressing PKC-δ were subjected to a GST-hBVR pull-down assay. As shown in FIG. 2A, GST-hBVR, but not GST alone, selectively bound PKC-δ from cell lysates at 30 min and 120 min incubation, suggesting protein:protein binding. Confirmation of this interaction was obtained by co-transfection of cells with plasmids expressing PKC-δ and HA-hBVR. The cell lysate of control cells or cells treated with PMA was immunoprecipitated with anti-HA antibodies, and the products separated by SDS-PAGE and blotted to membrane. Subsequent probing of the membrane with antibodies to PKC-δ and hBVR revealed a weak PKC-δ signal in non-treated cells, while upon treatment with PMA the intensity of PKC-δ band in the immunoprecipitate was strongly increased (FIG. 2B), indicating an in vivo association and the requirement of activation of proteins for stronger binding. Neither protein was detected in the immunoprecipitate with control IgG. Furthermore, hBVR and PKC-δ interaction was indicated by co-localization in confocal microscopy, using overexpressed hBVR (green) and PKC-δ (red fluorescence). A strong yellow-orange fluorescence in merged images supports partial co-localization of the polypeptides (FIG. 2C).

Example 3 hBVR Augments PKC-δ Activation by Phorbolester in Cells

Figure 3B:
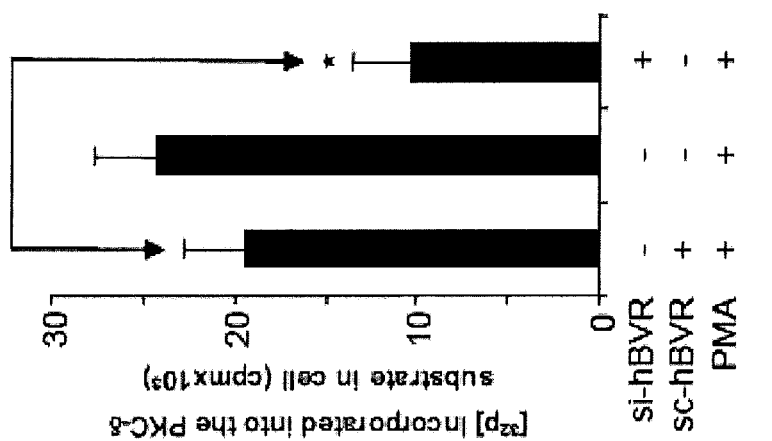
FIGS. 3A-3D demonstrate hBVR augmentation of PKC-δ activation by PMA in 293A cells. Results of a metabolic labeling analysis are shown in FIG. 3A. 293A cells were either transfected with a pcDNA3-hBVR plasmid or infected with a pSuper-si-hBVR construct, to overexpress or deplete hBVR from cells, respectively. Cells were starved for 24 h and metabolically labeled with [$^{32}$P]$H_3PO_4$ for another 4 h prior to treatment with PMA (100 nM, 15 min). Cell lysates were subjected to immunoprecipitation with anti-PKC-δ antibodies. Proteins were first separated by SDS-PAGE and then blotted onto PVDF membrane prior to autoradiography. After radioactive decay, the membrane was probed with the anti-PKC-δ antibodies as a reference for loading. The bar graph represents the ratio of phosphorylated PKC-δ vs. total PKC-δ protein. si-hBVR suppresses PMA activation of PKC-δ kinase activity as shown in FIG. 3B. Cells seeded into 48-well plates were infected with pSuper-si-hBVR or -sc-hBVR as a control. After starvation overnight, cells were treated as above with PMA and subsequently analyzed in situ for PKC-δ activity using the commercial PKC-δ specific substrate, ARRKRKGSFFGG (SEQ ID NO: 52). Rottlerin prevents hBVR-mediated PKC-δ activation (FIG. 3C). Cells were transfected with pcDNA-PKC-δ or co-transfected with pcDNA-hBVR. They were then starved overnight. When used, 20 μM Rottlerin was added 30 min prior to treatment. PKC-δ activity was measured as described above for FIG. 3B. hBVR increases kinase activity of constitutively active (ca) PKC-δ in cells as shown in FIG. 3D. Cells transfected with constitutively active pcDNA-PKC-δ-ca were also co-transfected with a plasmid to express hBVR where indicated and cells were starved prior to treatment with PMA. PKC-δ activity was determined in situ using a specific PKC-δ substrate.
Figure 3A:
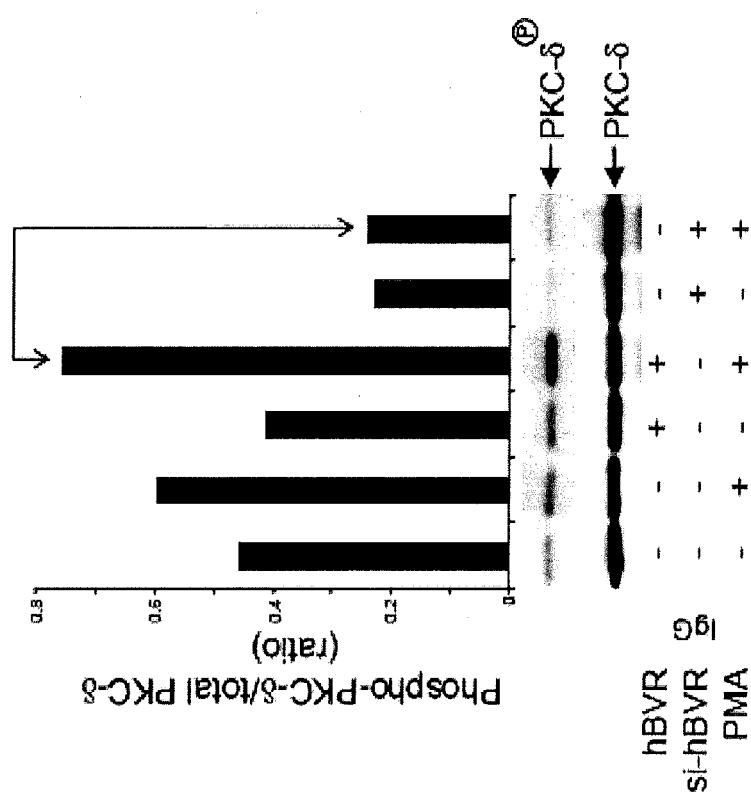

The activation of PKC-δ by hBVR was further examined in 293A cells by manipulating the level of hBVR either by transfection with wt-hBVR, or infection with si-hBVR construct to deplete hBVR from cells, or by treating with a specific inhibitor of the PKC. Starved and $^{32}P$ metabolically labeled cells were treated with PMA for 15 min, PKC-δ was immunoprecipitated, and the proteins recovered were separated by SDS-PAGE and subjected to autoradiography. When compared to the untreated cells, PMA-treatment resulted in a modest increase in PKC-δ phosphorylation (FIG. 3A). The magnitude of phosphorylation was further increased when hBVR was overexpressed and the cells were then treated with PMA. Phosphorylation was substantially decreased in si-hBVR-infected cells in the presence or absence of PMA. Next, the effect of si-hBVR on PKC-δ kinase activity in PMA-treated cells was tested using a specific PKC-δ substrate. As noted in FIG. 3B, activity was reduced by approximately 50% as reflected by incorporation of [$^{32}P$] into the peptide substrate.

Figures 3C, 3D:
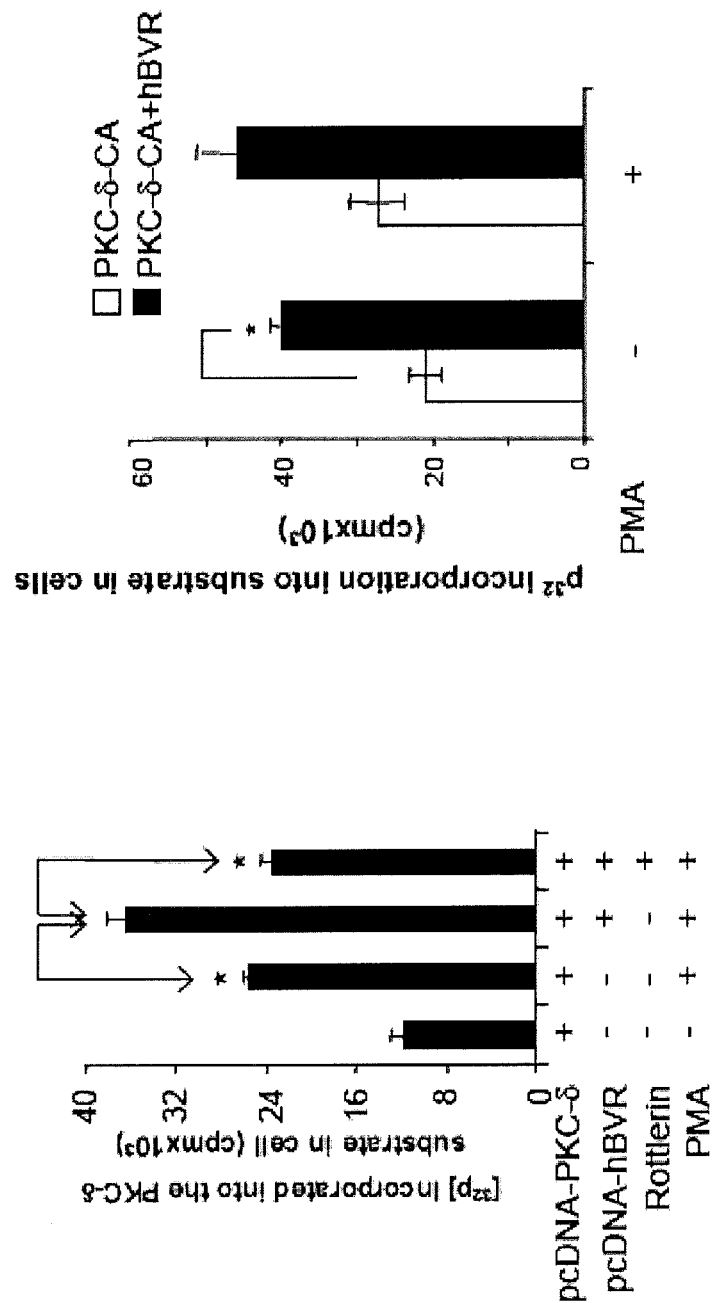

Because PMA also activates other PKCs, the specific inhibitor of PKC-δ, Rottlerin, was used to dissect out the effect of hBVR on PMA-activated PKC-δ from other isoforms of PKCs (FIG. 3C). As noted, in the presence of Rottlerin, there was a significant reduction in the magnitude of PKC-δ activation by PMA and hBVR in cells overexpressing the kinase.

A constitutively active PKC-δ was engineered by deleting 10 residues (aa151-160, QAKIHYIKNE; SEQ ID NO: 51) from the pseudo-substrate domain of the PKC (Zhao et al., "The Expression of Constitutively Active Isotypes of Protein Kinase C to Investigate Preconditioning," *J. Biol. Chem.* 273:23072-23079 (1998), which is hereby incorporated by reference in its entirety). Overexpression of the mutant PKC in vivo resulted in kinase activity that was minimally stimulated by PMA (FIG. 3D), whereas in cells co-transfected with hBVR, there was a significant stimulation of kinase activity. Thus, hBVR stimulation of PKC-δ occurs independently of other mechanisms that activate the kinase.

Example 4

Characterization of an hBVR-Based Peptide PKC-δ Substrate

Figure 4A:
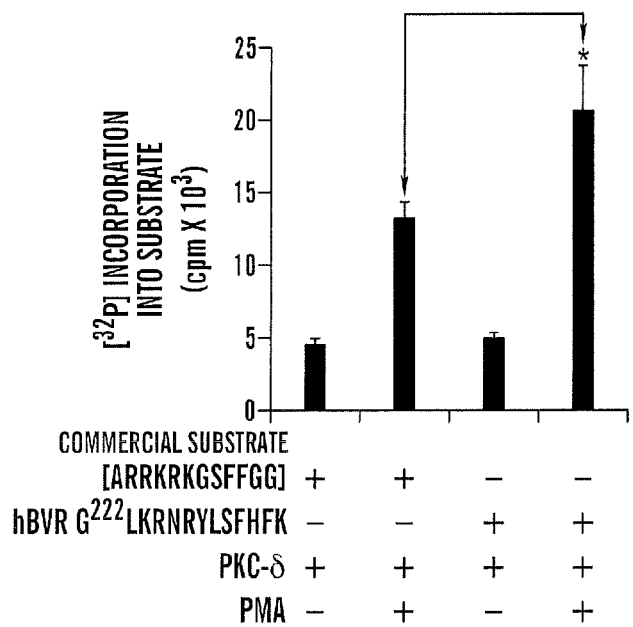
FIGS. 4A-4C show that PKC-δ efficiently phosphorylates an hBVR-based peptide containing SH2 domain docking motif.
Figure 4B:
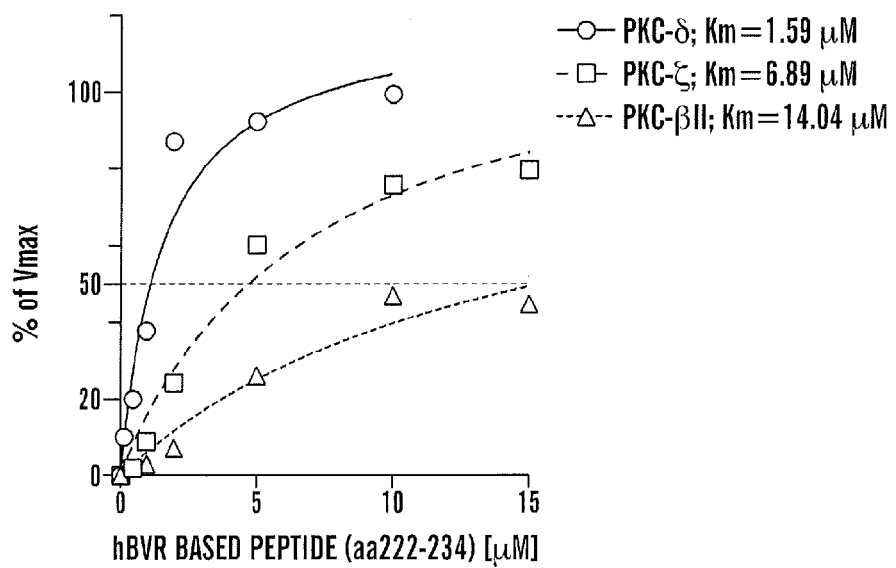
Figure 4C:
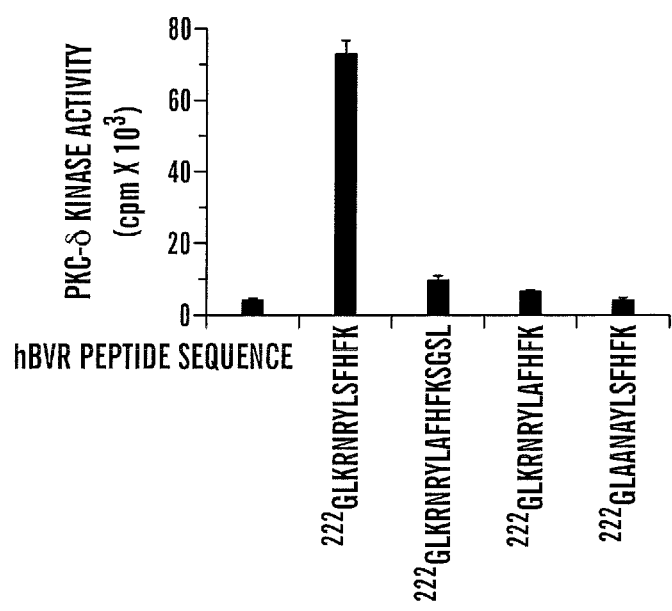

A similarity was noted between the composition of residues in hBVR segment aa222-234 (GLKRNRYLSFHFK; SEQ ID NO: 70) and the composition of residues in a commercial peptide (ARRKRKGSFFGG; SEQ ID NO: 52) identified by Nishikawa as the optimal substrate for PKC-δ (Nishikawa et al., "Determination of the Specific Substrate Sequence Motifs of Protein Kinase C Isozymes," *JBiol. Chem.* 272:952-960 (1997), which is hereby incorporated by reference in its entirety). The YLSF consensus SH2 domain of hBVR is within this segment, and it was therefore examined whether the serine residue in the peptide, which corresponds to $S^{230}$ in hBVR, is a target of phosphorylation by the kinase, and hence whether it is a component of hBVR's protein:protein interaction. The in situ kinase assay and cells overexpressing PKC-δ were used to test this possibility. The commercial peptide served as the positive control; the two peptides were used at an equimolar concentration. As noted in FIG. 4A the hBVR-based peptide was a remarkably good substrate for PKC, in fact, it was a superior substrate for the PMA-activated PKC-δ. This observation was further examined by measuring concentration dependence of the phosphorylation. Data obtained for increasing peptide substrate concentrations were fitted to the Michaelis-Menton equation, yielding a $K_m$ of 1.59±0.58) .μM (FIG. 4B). This value compares favorably with the reported $K_m$ for the commercial substrate (0.98 μM) (Nishikawa et al., "Determination of the Specific Substrate Sequence Motifs of Protein Kinase C Isozymes," *JBiol. Chem.* 272:952-960 (1997), which is hereby incorporated by reference in its entirety). Whether the serine residue in the hBVR-based peptide (aa222-234) was a substrate specific to PKC-δ was tested by comparing to the conventional PKC-βII and the atypical PKC-ζ. Both kinases were able to use the peptide as substrate (FIG. 4B); the highest affinity for the peptide is observed with PKC-δ and PKC-ζ($K_m$6.89 μM) and the lowest with PKC-βII ($K_m$14.03 μM). Target specificity of PKC-δ for the serine in YLSF sequence, as well as the significance of its upstream flanking arginine and lysine residues, to phosphorylation of the peptide by the PKC was examined (FIG. 4C). A variant peptide in which the target serine was replaced by alanine was, as expected, not a substrate for the kinase. To test the specificity of the serine ($S^{230}$) as the acceptor of phosphates, a longer variant of the alanine-mutant peptide (hBVR aa222-238) that includes two additional serines (corresponding to hBVR $S^{235}$ and $S^{237}$) was used as substrate. As with the shorter peptide, the replacement of serine with alanine markedly decreased phosphorylation of the peptide. This finding indicates that hBVR $S^{230}$ is the specific PKC-δ phosphorylation target and that this segment of hBVR is a participant in binding to the PKC. The failure of other serines in the peptide to serve as targets for the kinase highlights the presence of the positively charged residues, upstream of the target serine, as the key to phosphorylation of the serine in YLSF sequence by the PKC. Indeed, a second variant of the aa222-234 peptide in which the upstream lysine and arginine residues were replaced by alanine was also not a substrate for PKC-δ, despite the presence of the target serine. The observed essential role of positively charged residues to render the peptide a suitable substrate is in keeping with composition of the optimal substrate for PKC-δ as identified by Nishikawa (Nishikawa et al., "Determination of the Specific Substrate Sequence Motifs of Protein Kinase C Isozymes," *J Biol. Chem.* 272:952-960 (1997), which is hereby incorporated by reference in its entirety).

Example 5

Identification of a Potent hBVR-Based PKC-δ Inhibitor Peptide

Figures 5C, 5D:
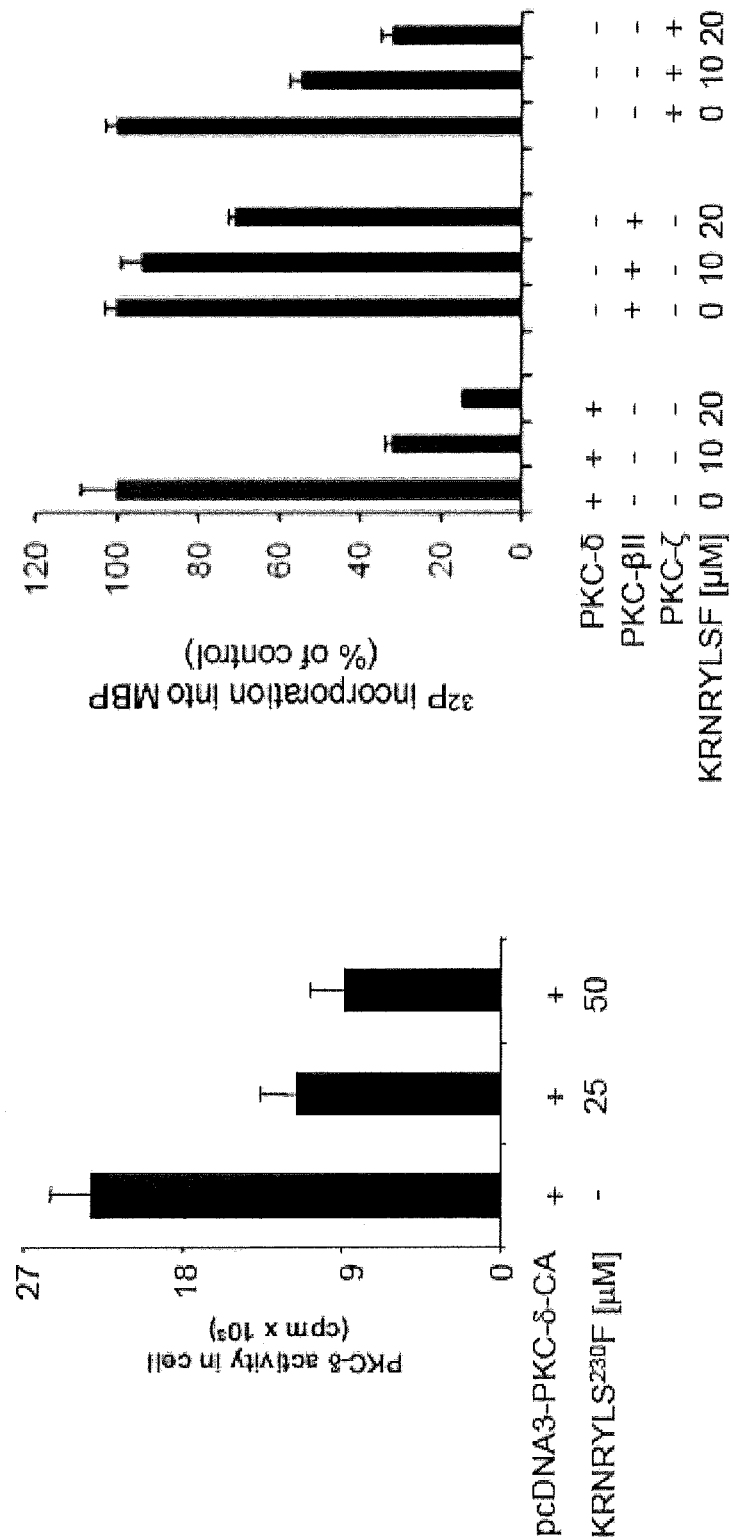

Previous studies have shown that a peptide sequence, contained within the aa222-234 peptide, was an inhibitor of PKC-ζ(Lerner-Marmarosh et al., "Regulation of TNF-alpha-Activated PKC-zeta Signaling By the Human Biliverdin Reductase: Identification of Activating and Inhibitory Domains of the Reductase," *FASEB J.* 21:3949-3962 (2007), which is hereby incorporated by reference in its entirety), whereas the longer form of the peptide is a substrate for PKC-δ (FIG. 4B). Due to the differences between PKC-δ and PKC-ζ, peptides were screened for their inhibitory activity against PKC-δ. The peptide corresponding to the hBVR aa224-231 (KRNRYLS$^{230}$F; SEQ ID NO: 19), which has a preponderance of positively charged residues, was found to be a remarkably effective inhibitor of the PKC in vitro (FIG. 5A). More than 90% inhibition of phosphorylation of the commercial substrate was observed at a substrate-inhibitor molar ratio of 5:1 (50 μM substrate/10 μM inhibitor). This outcome clearly differed from that manifested by the hBVR-based aa230-238 (S$^{230}$FHFKSGSL; SEQ ID NO: 53), which had 2 additional serine residues. This finding is consistent with the conclusion, noted in Example 4, that this segment of hBVR is a protein:protein interaction site. Data shown in FIG. 5B were obtained performing a similar experiment in cells transfected with pcDNA-PKC-δ and stimulated with PMA confirm the inhibitory activity of the peptide. To examine whether the inhibition of kinase activity might be due to a PMA:peptide interaction that blocks PKC:phorbol ester interaction, a similar experiment was carried out using a constitutively active form of PKC-δ (FIG. 5C). Cells were transfected with the constitutively active pcDNA-PKC-δ, and were subsequently treated with the indicated concentration of the peptide. The peptide was an effective inhibitor of the constitutively active kinase. This supports the conclusion that there is direct interaction between the peptide and the kinase.

Figure 5E:
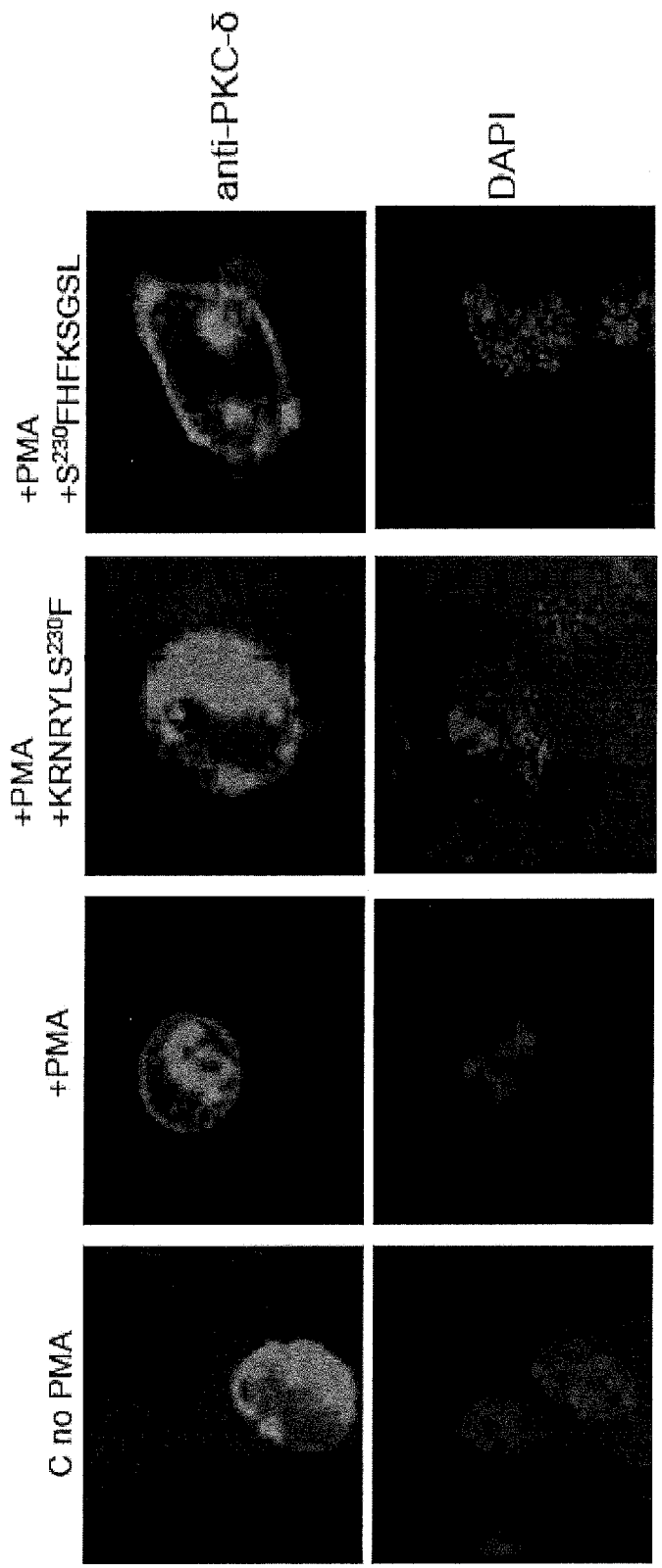

The specificity of the inhibitory peptide toward PKC-δ, PKC-βII and PKC-ζ was compared (FIG. 5D) using increasing concentrations of the peptide and similar concentrations of the PKC enzymes, using MBP as the substrate for PKCs. Assay conditions were optimal for each PKC isoform as described in Materials and Methods. The peptide exerted differential effects on the kinases; the activity of the PKC-δ was most sensitive to the inhibitor, PKC-βII was essentially unaffected at concentrations that markedly inhibited PKC-δ, while PKC-ζ was responsive to the peptide, although higher concentrations of the peptide were required to produce the same degree of inhibition, confirming previous observations (Lerner-Marmarosh et al., "Regulation of TNF-alpha-Activated PKC-zeta Signaling By the Human Biliverdin Reductase: Identification of Activating and Inhibitory Domains of the Reductase," *FASEB J.* 21:3949-3962 (2007), which is hereby incorporated by reference in its entirety). It is noteworthy that the efficiency with which the peptide inhibited each enzyme correlates with the affinity of the kinases for the longer substrate peptide (FIG. 4B). Translocation of PKCs in the cell is a reflection of their activation. Therefore, whether the inhibitory peptide might also disrupt this process was examined in PMA-treated cells transfected with red fluorescence-tagged pcDNA-PKC-δ; the nucleus was visualized from blue fluorescence of DAPI. The effect of the two hBVR-derived peptides on PKC-δ activation by PMA was tested by confocal microscopy. The finding is shown in FIG. 5E. In untreated cells PKC-δ was dispersed throughout the cytoplasm, while upon PMA-treatment the PKC translocated to the cell membrane. This translocation was effectively inhibited when KRNRYLSF (SEQ ID NO:19) peptide was introduced into cells, whereas SFHFKSGSL (SEQ ID NO: 53) peptide did not significantly affect PKC-δ translocation.

Figure 6C:
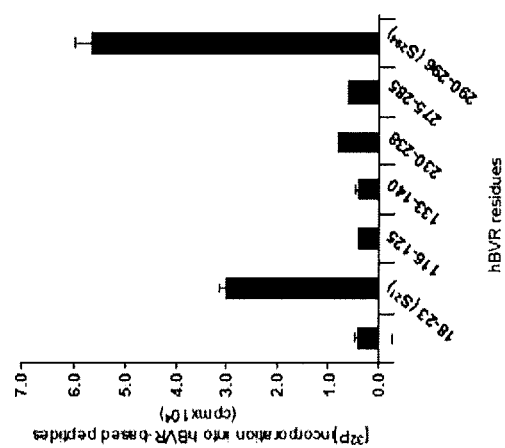
FIGS. 6A-6C show that PKC-δ activates the reductase activity of hBVR, while bilirubin, the activity product, suppresses PKC-δ activity. Phosphorylation by PKC-δ kinase increases hBVR reductase activity as shown in FIG. 6A. PKC-δ was used to phosphorylate hBVR in vitro, under standard assay conditions with cold ATP for 30 min at 37° C. As controls, either hBVR was incubated in the absence of PKC-δ, or PKC-δ was incubated in the absence of hBVR. The reaction products were then assayed for reductase activity as described infra. Bilirubin suppresses PKC-δ activity as shown in FIG. 6B. Cells transfected with PKC-δ were starved overnight and pretreated with bilirubin (40 μM) 1 h before the 15 min treatment with PMA. In situ kinase activity was determined as described in FIG. 3A. hBVR S$^{21}$ and S$^{294}$ are additional potential targets for phosphorylation by PKC-δ as shown in FIG. 6C. The incorporation of [$^{32}$P] into hBVR-derived peptides was examined in a kinase reaction for PKC-δ activity. hBVR-derived peptides (10 μM) were pre-incubated with PKC-δ at room temperature for 5 min prior to the addition of radioactive ATP. After 30 min incubation at 30° C. the incorporated radioactivity was measured by the P81 assay.
Figure 6B:
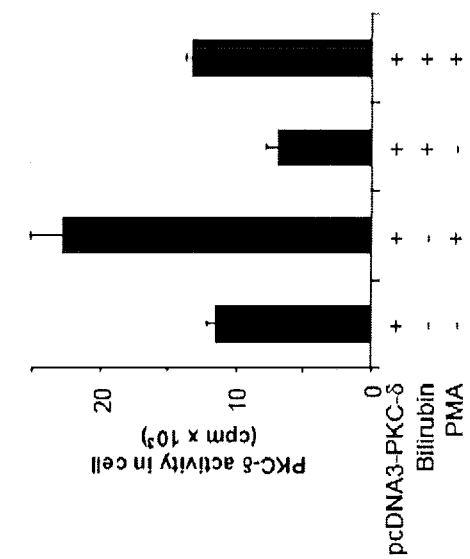
Figure 6A:
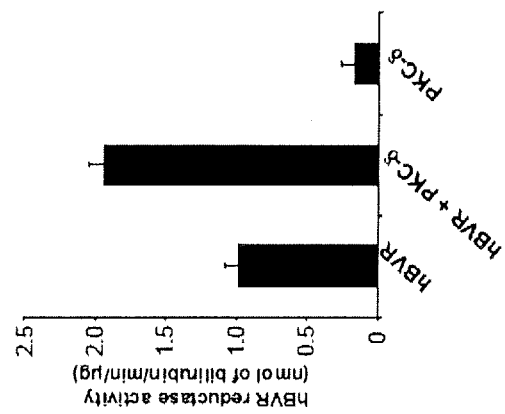

Example 6 hBVR Reductase Activity is Increased in the Presence of PKC-δ and Bilirubin Blocks Activation of PKC-δ by PMA in the Cell Because the reductase activity of hBVR is phosphorylation-dependent (Salim et al., "Human Biliverdin Reductase is Autophosphorylated, and Phosphorylation is Required for Bilirubin Formation," *J. Biol. Chem.* 276: 10929-10934 (2001), which is hereby incorporated by reference in its entirety), it was examined whether hBVR phosphorylation by PKC-δ enhanced its activity. hBVR was first phosphorylated by PKC-δ in vitro, after which the activated hBVR was tested in the reductase assay. The hBVR recovered from the kinase reaction showed a significant increase in reductase activity compared to the control sample where PKC-δ was omitted (FIG. 6A). To examine whether increased hBVR activity has an effect on the PKC, a further experiment was carried out. Bilirubin, the product of hBVR activity was added to cells prior to treatment with PMA and assayed for PKC-δ kinase activity using the commercial substrate (FIG. 6B). Bilirubin was an effective inhibitor of the PKC activity, both in PMA-activated and untreated cells transfected with PKC-δ expression construct. The findings indicate the likelihood of a feedback loop between hBVR and the PKC. While PKC-δ increases the reductase activity, the product of the reductase inhibits the PKC.

While it is apparent that PKC-δ phosphorylates S$^{230}$, it is also plausible that there may be other targets of PKC-δ in hBVR. To this end, several hBVR-derived peptides encompassing the consensus PKC phosphorylation motifs as well as randomly selected S/T containing hBVR-based peptides were used as PKC substrates (FIG. 6C). PKC enzymes, including PKC-δ, phosphorylate S/T residues in defined consensus motifs that include SXR/K (SEQ ID NO: 46) and RXXS/T (SEQ ID NO: 54) sequences. The primary structure of hBVR predicts those consensus sequences encompassing 3 serine residues:S$^{21}$VR, S$^{294}$RK and RYLS$^{230}$F (SEQ ID NO: 55). Possible phosphorylation sites were indicated by a several fold increase in phosphate incorporated in two peptides corresponding to hBVR aa18-23 and aa290-296. The serine residues in the other two hBVR-based peptides that are phosphorylated by the PKC correspond to S$^{21}$ and S$^{294}$ observed in the consensus PKC phosphorylation motifs.

Discussion of Examples 1-6

Biliverdin IXα reductase is an evolutionarily conserved multi-functional protein with primary and secondary features that define its functions, not only in the reductase capacity, but also at several vital junctions in the insulin/IGF-1 signal transduction pathways (reviewed in Kapitulnik et al., "Pleiotropic Functions of Biliverdin Reductase: Cellular Signaling and Generation of Cytoprotective and Cytotoxic Bilirubin," *Trends Pharmacol. Sci.* 30:129-137 (2009), Maines M. D., "Biliverdin Reductase: PKC Interaction At the Cross-Talk of MAPK and PI3K Signaling Pathways," *Antioxid. Redox Signal.* 9:2187-2195 (2007), Maines M., "New Insights Into Biliverdin Reductase Functions: Linking Heme Metabolism To Cell Signaling," *Physiology* 20:382-389 (2005), which are hereby incorporated by reference in their entirety). The kinase and reductase activities of hBVR converge in controlling stress-mediated activation of the downstream effectors of the two major branches of insulin/IGF-1 pathway, signaling the stress-activated MAPK and the PI3K pathways and resulting in stimulation of stress-inducible gene expression (Kapitulnik et al., "Pleiotropic Functions of Biliverdin Reductase: Cellular Signaling and Generation of Cytoprotective and Cytotoxic Bilirubin," *Trends Pharmacol. Sci.* 30:129-137 (2009), Maines M. D., "Biliverdin Reductase: PKC Interaction At the Cross-Talk of MAPK and PI3K Signaling Pathways," *Antioxid. Redox Signal.* 9:2187-2195 (2007), Maines M., "New Insights Into Biliverdin Reductase Functions: Linking Heme Metabolism To Cell Signaling," *Physiology* 20:382-389 (2005), which are hereby incorporated by reference in their entirety). The two signaling branches extensively cross-talk through PKC enzymes and PKB/Akt as they form an integrated network of signaling for regulation of a vast array of cellular functions.

The structure and mechanisms of activation of PKC-δ, a novel (n) PKC isoform, differ from those of conventional and atypical PKCs (Newton et al., "Protein Kinase C: A Paradigm for Regulation of Protein Function by Two Membrane-Targeting Modules," *Biochim. Biophy.s Acta* 1376: 155-172 (1998), Dempsey et al., "Protein Kinase C Isozymes and the Regulation of Diverse Cell Responses," *Am. J. Physiol. Lung Cell. Mol. Physiol.* 279:L429-438 (2000), which are hereby incorporated by reference in their entirety). With respect to structure, the C2-like region in PKC-δ amino terminus acts as the regulatory domain. In this domain, the pseudo-substrate sequence that is between the C1 and the C2-like region keeps the kinases in inactive conformation by interacting with the substrate recognition region in the catalytic domain (Dutil et al., "Dual Role of Pseudosubstrate in the Coordinated Regulation of Protein Kinase C by Phosphorylation and Diacylglycerol," *J. Biol. Chem.* 275:10697-10701 (2000), which is hereby incorporated by reference in its entirety). There are a number of ways that PKC-δ is activated (Jaken et al., "Protein Kinase C Binding Partners," *Bioessays* 22:245-254 (2000), Kikkawa et al., "Protein Kinase C Delta (PKC delta): Activation Mechanisms and Functions," *J. Biochem.* 132:831-839 (2002), which are hereby incorporated by reference in their entirety), including phosphorylation at the hydrophobic motif sites, phorbol ester (as well as DAG) binding to the cysteine rich C1b region, change in conformation and generation of a catalytically active fragment by proteolysis and tyrosine phosphorylation in response to ROS generating stimuli (Kikkawa et al., "Protein Kinase C Delta (PKC delta): Activation Mechanisms and Functions," *J. Biochem.* 132:831-839 (2002), Fukunaga et al., "UV-Induced Tyrosine Phosphorylation of PKC Delta and Promotion of Apoptosis in the HaCaT Cell Line" *Biochem. Biophys. Res. Commun.* 289:573-579 (2001), which are hereby incorporated by reference in their entirety). Several serines ($S^{505}$, $S^{62}$, and $S^{43}$) and a glutamic acid ($E^{500}$) have been identified in catalytic maturation of the PKC (Gschwendt, M., "Protein kinase C Delta," *Eur. J. Biochem.* 259:555-564 (1999), Stempka et al., "Requirements of Protein Kinase cdelta for Catalytic Function. Role of Glutamic Acid 500 and Autophosphorylation on Serine 643," *J. Biol. Chem.* 274:8886-8892 (1999), which are hereby incorporated by reference in their entirety).

A number of observations made in the preceding Examples indicate that the mechanism of hBVR activation of PKC-δ involves a conformational change that is brought about by protein: protein interaction. The observations include: a) in vitro activation of PKC-δ by hBVR in absence of other proteins; b) the kinase-dead hBVR was as effective as its competent form in promoting PKC-δ activation; c) kinase/dead PKC-δ was not activated by hBVR; and d) in the cell, the two proteins interacted as indicated by co-immunoprecipitation of the two proteins and binding observed in GST-pull-down assay. Less direct evidence for the interaction between PKC-δ and hBVR is offered by the observation that a peptide designed based on the primary structure of hBVR (aa222-234), containing a PKC phosphorylation motif (RXXS/T; SEQ ID NO: 54) and prevalence of charged and hydrophobic residues, was an excellent substrate for the PKC. A truncated portion of the substrate peptide, containing the phosphorylation motif, without the down stream hydrophobic segment, was a potent inhibitor of PKC-δ activity in vitro and in the cell. The ability of the hBVR-based peptide to inhibit PKC-δ activity is not unique as inhibitor peptides targeting other regions of PKC-δ have been characterized (Qi et al., "Sustained Pharmacological Inhibition of deltaPKC Protects Against Hypertensive Encephalopathy Through Prevention of Blood-Brain Barrier Breakdown in Rats," *J. Clin. Invest.* 118:173-182 (2008), Kheifets et al., "Protein Kinase C Delta (deltaPKC)-Annexin V Interaction: A Required Step in deltaPKC Translocation and Function," *J. Biol. Chem.* 281:23218-23226 (2006), which are hereby incorporated by reference in their entirety).

The sequence of the substrate peptide bears a striking similarity to that of the PKC-δ target sequence in the naturally occurring substrate, MARCKS (KKKRFSFKKS-FKLSG; SEQ ID NO: 56) (Liu et al., "Independence of Protein Kinase C-delta Activity From Activation Loop Phosphorylation: Structural Basis and Altered Functions in Cells," *J. Biol. Chem.* 281:12102-12111 (2006), which is hereby incorporated by reference in its entirety), indicating that the inhibitory portion of the peptide (KRNRYLSF; SEQ ID NO: 19) may disrupt substrate:PKC-δ interaction. Furthermore, as with other PKCs, activation of PKC-δ is linked to its translocation within the cellular compartments, and when activated by phorbolesters, it translocates from the cytosol to the plasma membrane (Wang et al., "Differential Localization of Protein Kinase C Delta by Phorbol Esters and Related Compounds Using A Fusion Protein With Green Fluorescent Protein," *J. Biol. Chem.* 274:37233-37239 (1999), Brandt et al., "Helicobacter Pylori Activates Protein Kinase C Delta To Control Raf in MAP Kinase Signalling: Role in AGS Epithelial Cell Scattering and Elongation," *Cell Motil. Cytoskeleton* 66(10):874-92 (2009), which are hereby incorporated by reference in their entirety). The observed failure of PKC-δ to translocate to the plasma membrane in the PMA-treated cells in the presence of the small inhibitory peptide is in agreement with the interpretation of data as supporting protein:protein interaction as the key mechanism for hBVR activation of the PKC.

The finding that kinase-dead hBVR increases phosphorylation of PKC-δ, in the absence of any other kinase or PMA, is supportive of this proposed activation mechanism. In addition, the finding that kinase-dead PKC-δ is not activated by the kinase competent hBVR is in line with this mechanism, as is the observation that constitutively active PKC-δ in the absence of an activator (PMA) is inhibited in the cell by the inhibitory hBVR-based peptide.

In the cell, however, it is likely that hBVR activation of PKC-δ is not an exclusive process involving only the two proteins; rather, it most likely has additional components, including hBVR's phosphorylation by PKC-ζ, which is trans-activated by hBVR (Lerner-Marmarosh et al., "Regulation of TNF-alpha-Activated PKC-zeta Signaling By the Human Biliverdin Reductase: Identification of Activating and Inhibitory Domains of the Reductase," *FASEB J.* 21:3949-3962 (2007), which is hereby incorporated by reference in its entirety), as well as hBVR-mediated activation of the MEK/ERK/Elk signaling (Lerner-Marmarosh et al., "Human Biliverdin Reductase is an ERK Activator;

hBVR is an ERK Nuclear Transporter and is Required for MAPK Signaling," *Proc. Natl. Acad. Sci. U.S.A.* 105:6870-6875 (2008), Liu et al., "Protein Kinase C-delta Regulates Migration and Proliferation of Vascular Smooth Muscle Cells Through the Extracellular Signal-Regulated Kinase 1/2," *J. Vasc. Surg.* 45:160-168 (2007), which are hereby incorporated by reference in their entirety). Indeed, upstream kinases in the cell, including PKC-ζ, have been shown to phosphorylate PKC-δ activation loop S/T targets (Le Good et al., "Protein Kinase C Isotypes Controlled by Phosphoinositide 3-kinase Through the Protein Kinase PDK1," *Science* 281:2042-2045 (1998), which is hereby incorporated by reference in its entirety). Although the possibility that hBVR directly phosphorylates the PKC cannot be dismissed, the finding that under hBVR assay conditions the PKC was not appreciably phosphorylated, argues against this possibility. This distinguishes activation of PKC-δ from PKC-βII, which is both phosphorylated, apparently in its activation loop, and activated as a consequence of protein: protein binding and presumed conformational change (Maines M. D., "Biliverdin Reductase: PKC Interaction At the Cross-Talk of MAPK and PI3K Signaling Pathways," *Antioxid. Redox Signal.* 9:2187-2195 (2007), which is hereby incorporated by reference in its entirety). The activation of PKC-δ activity is not invariably dependent on phosphorylation of the activation loop (Liu et al., "Independence of Protein Kinase C-delta Activity From Activation Loop Phosphorylation: Structural Basis and Altered Functions in Cells," *J. Biol. Chem.* 281:12102-12111 (2006), which is hereby incorporated by reference in its entirety).

The outcome of stimulation of PKC-δ and hBVR reductase activity can pose diametrically opposite effects with respect to cell survival/death (Jackson et al., "The Enigmatic Protein Kinase C delta: Complex Roles in Cell Proliferation and Survival," *FASEB J.* 18:627-636 (2004), which is hereby incorporated by reference in its entirety). The significance of trans-activation of hBVR and PKC-δ should be interpreted in the context of cellular functions that are associated with, or are suspected to involve, activity of PKC-δ and oxidative stress. Because the kinase and reductase activities of hBVR are linked (Miralem et al., "Small Interference RNA-Mediated Gene Silencing of Human Biliverdin Reductase, But Not That of Heme Oxygenase-1, Attenuates Arsenite-Mediated Induction of the Oxygenase and Increases Apoptosis in 293A Kidney Cells," *J. Biol. Chem.* 280:17084-17092 (2005), Salim et al., "Human Biliverdin Reductase is Autophosphorylated, and Phosphorylation is Required for Bilirubin Formation," *J. Biol. Chem.* 276:10929-10934 (2001), which are hereby incorporated by reference in their entirety), the increased reductase activity and the resulting enhancement of bilirubin formation potentiates the antioxidant potential of the cell (Ryter et al., "Carbon Monoxide and Bilirubin: Potential Therapies for Pulmonary/Vascular Injury and Disease," *Am. J. Respir. Cell. Mol. Biol.* 36:175-182 (2007), Stocker et al., "Bilirubin is an Antioxidant of Possible Physiological Importance," *Science* 235:1043-1046 (1987), Halliwell B., "Biochemistry of Oxidative Stress," *Biochem. Soc. Trans.* 35:1147-1150 (2007), Sedlak et al., "Bilirubin and Glutathione Have Complementary Antioxidant and Cytoprotective Roles," *Proc. Natl. Acad. Sci. U.S.A.* 106:5171-5176 (2009), which are hereby incorporated by reference in their entirety). This could negate the pro-apoptotic activity of the PKC-δ (Jackson et al., "The Enigmatic Protein Kinase C delta: Complex Roles in Cell Proliferation and Survival," *FASEB J.* 18:627-636 (2004), which is hereby incorporated by reference in its entirety).

Accordingly, it is not unreasonable to propose the occurrence of a regulatory loop between hBVR/PKC-δ, wherein PKC-δ activation initiates a mechanism for self-limitation and hence curtailment of those functions in which it is implicated, including cell differentiation, cell death and expression of NO synthase (Hug et al., "Protein Kinase C Isoenzymes: Divergence in Signal Transduction?" *Biochem. J.* 291(2):329-343 (1993), which is hereby incorporated by reference in its entirety). Moreover, because of the commonality of stimuli that activate hBVR and PKC-δ, their downstream effector kinases and transcription factors, together with the presently found trans-activation, would be expected to transcend their individual signaling activities. It is reasonable to suspect that in PKC-δ related disorders, such as in the case of the autoimmune disease lupus (Gorelik et al., "PKC-delta Nitrosilation Impairs ERK Pathway Signaling in Lupus T Cells," *J. Immunol.* 178 (2007), which is hereby incorporated by reference in its entirety), there may be an associated defect in hBVR expression and activity.

On the other hand, although PKC-δ is commonly associated with pro-apoptotic functions, there are those instances, such as certain types of tumor cells in which overexpression of PKC-δ sustains cell survival (Clark et al., "Altered Protein Kinase C (PKC) Isoforms in Non-Small Cell Lung Cancer Cells: PKCdelta Promotes Cellular Survival and Chemotherapeutic Resistance," *Cancer Res.* 63:780-786 (2003), McCracken et al., "Protein Kinase C Delta is a Prosurvival Factor in Human Breast Tumor Cell Lines," *Mol. Cancer Ther.* 2:273-281 (2003), which are hereby incorporated by reference in their entirety). In non-small cell lung cancer cells PKC-δ promotes chemotherapeutic resistance, and in human breast tumor cells it functions as a survival factor (Clark et al., "Altered Protein Kinase C (PKC) Isoforms in Non-Small Cell Lung Cancer Cells: PKCdelta Promotes Cellular Survival and Chemotherapeutic Resistance," *Cancer Res.* 63:780-786 (2003), McCracken et al., "Protein Kinase C Delta is a Prosurvival Factor in Human Breast Tumor Cell Lines," *Mol. Cancer Ther.* 2:273-281 (2003), which are hereby incorporated by reference in their entirety). The peptide may also be useful in those conditions that are linked to oxidative damage and cytokine-mediated inflammation, such as pancreatitis. TNF-α initiates NF-κB activation by mechanisms that involve convergence of novel PKCs including PKC-δ (Liu et al., "NF-kappaB Is Required for UV-induced JNK Activation Via Induction of PKCdelta," *Mol. Cell* 21:467-480 (2006), which is hereby incorporated by reference in its entirety), while hBVR (which is also activated by TNF-α) and its tetrapyrrole substrate, biliverdin, activate and inhibit NF-κB activity, respectively (Liu et al., "NF-kappaB Is Required for UV-induced JNK Activation Via Induction of PKCdelta," *Mol. Cell* 21:467-480 (2006), which is hereby incorporated by reference in its entirety). TNF-α initiated NF-κB activation involving PKC-δ has been identified as playing a key role in pancreatitis (Liu et al., "NF-kappaB Is Required for UV-induced JNK Activation Via Induction of PKCdelta," *Mol. Cell* 21:467-480 (2006), which is hereby incorporated by reference in its entirety).

Materials and Methods for Examples 7-11

Materials: Recombinant PKC-δ, the specific PKC-δ peptide substrate and PMA were obtained from Calbiochem (San Diego, Calif.). The hBVR-derived peptides: F$^{162}$GFPAFSG (SEQ ID NO: 34) and K$^{275}$KRILHCLGLA (SEQ ID NO: 25), and the PKC-δ C-terminal peptide S$^{658}$AFAGFSFVNPKFEHLLED (SEQ ID NO: 57), in both unmodified and N-myristoylated forms, were synthesized by EZBiolab (Westfield, Ind.). Polyclonal anti-PKC-δ antibodies were from Cell Signaling. Anti-ERK-2 and anti-HA mouse monoclonal antibodies, as well as si-RNA and control RNA for human PKC-δ, ERK1, ERK2, and MEK1, were from Santa Cruz Biotechnology (Santa Cruz, Calif.). Anti-human hBVR polyclonal antibodies were obtained as described before (Maines et al., "Purification and Characterization of Human Biliverdin Reductase," *Arch Biochem Biophys* 300(1):320-326 (1993), which is hereby incorporated by reference in its entirety). MEK1, MBP, and lipid activators were purchased from Millipore (Billerica, Mass.).

Plasmids and mutant constructs: The plasmid pcDNA-HA-hBVR contains the open reading frame of hBVR fused downstream of the HA epitope. Plasmids encoding the hBVR mutants $V^{11-14}$, $G^{17}$ to A (kinase-inactive), $F^{162}$ to V, $F^{164}$ to A, $F^{167}$ to V (C-box mutant) and $I^{278}$ to A, $L^{279}$ to A, $L^{282}$ to A, $L^{284}$ to A (D-box mutant) were made by site directed mutagenesis of wild-type hBVR cDNA clones (Maines et al., "Human Biliverdin IXalpha Reductase is a Zinc-Metalloprotein. Characterization of Purified and *Escherichia Coli* Expressed Enzymes," *Eur J Biochem* 235(1-2):372-381 (1996), which is hereby incorporated by reference in its entirety) and were verified by sequencing. The human PKC-δ open reading frame was amplified by PCR from a human brain cDNA library (Invitrogen, Carlsbad, Calif.) and cloned into pcDNA3 (mammalian expression) or pGEX-4T2 (*E. coli* expression). The human PKC-δ constructs: kinase-inactive ($K^{378}$ to R; Li et al., "Characterization of a Protein Kinase C-Delta (PKC-Delta) ATP Binding Mutant. An Inactive Enzyme that Competitively Inhibits Wild Type PKC-Delta Enzymatic Activity," *J. Biol. Chem.* 270(14):8311-8318 (1995), which is hereby incorporated by reference in its entirety) and constitutively active (Δ151-160; Zhao et al., "The Expression of Constitutively Active Isotypes of Protein Kinase C to Investigate Preconditioning," *J. Biol. Chem.* 273(36):23072-23079 (1998), which is hereby incorporated by reference in its entirety) were constructed by site-directed mutagenesis; the C-terminal deletion (Δ656-676) was created from the wt construct by amplification with an appropriate 3' primer.

Cell Culture, infection, transfection, and co-immunoprecipitation: HEK293A cells were grown and transfected with pcDNA3-HA-hBVR or pcDNA3-PKC-δ plasmids using conditions described elsewhere (Kravets et al., "Biliverdin Reductase, a Novel Regulator for Induction of Activating Transcription Factor-2 and Heme Oxygenase-1," *J. Biol. Chem.* 279(19):19916-19923 (2004); Maines et al., "Human Biliverdin Reductase, a Previously Unknown Activator of Protein Kinase C BetaII," *J. Biol. Chem.* 282(11):8110-8122 (2007), which are hereby incorporated by reference in their entirety), and overexpression was confirmed by western blotting. Preparation and use of viruses expressing si-hBVR or sc-hBVR (randomized control for sihBVR) was as previously described (Miralem et al., "Small Interference RNA-Mediated Gene Silencing of Human Biliverdin Reductase, But Not That of Heme Oxygenase-1, Attenuates Arsenite-Mediated Induction of the Oxygenase and Increases Apoptosis in 293A Kidney Cells," *J. Bio. Chem.* 280(17):17084-17092 (2005), which is hereby incorporated by reference in its entirety). Transfection of cells with synthetic si-RNA was performed as recommended by the manufacturer. Immunoprecipitates from cell lysates were prepared as described previously (Kravets et al., "Biliverdin Reductase, a Novel Regulator for Induction of Activating Transcription Factor-2 and Heme Oxygenase-1," *J. Biol. Chem.* 279(19):19916-19923 (2004); Maines et al., "Human Biliverdin Reductase, a Previously Unknown Activator of Protein Kinase C BetaII," *J. Biol. Chem.* 282(11):8110-8122 (2007), which are hereby incorporated by reference in their entirety) and were separated by SDS PAGE, followed by blotting to nitrocellulose. Specific details are given in the appropriate figure legends.

Metabolic labeling: Labeling of serum-starved, synchronized cells with carrier-free $[^{32}P]H_3PO_4$ was essentially as described previously (Lerner-Marmarosh et al., "Regulation of TNF-Alpha-Activated PKC-Zeta Signaling by the Human Biliverdin Reductase: Identification of Activating and Inhibitory Domains of the Reductase," *FASEB J.* 21(14):3949-3962 (2007), which is hereby incorporated by reference in its entirety). After 4 h labeling the cells were treated with 100 nM PMA for 15 min. Cell lysate was immunoprecipitated with anti-PKC-δ antibodies and phosphorylated proteins were visualized by autoradiography after gel electrophoresis.

Measurement of PKC-δ activity: PKC-δ assay in vitro was performed using 0.1 ng/μl purified recombinant human PKC-δ kinase with reaction conditions specified by the manufacturer. Effector molecules such as hBVR or peptides were added 5 min prior to substrate. The reaction was started by the addition of $[\gamma-^{32}P]$-ATP (Lerner-Marmarosh et al., "Human Biliverdin Reductase: A Member of the Insulin Receptor Substrate Family with Serine/Threonine/Tyrosine Kinase Activity," *Proc. Natl. Acad. Sci. U.S.A.* 102(20):7109-7114 (2005), which is hereby incorporated by reference in its entirety). Reaction products were detected either by gel electrophoresis and autoradiography or by the p81 filter assay. PKC-δ activity on agarose beads was also measured. Cell lysates were immunoprecipitated with anti-PKC-δ antibody followed by protein A/G agarose. The immunoprecipitates were used in kinase reactions containing 50 μM PKC-δ specific peptide substrate as above; incorporation of $^{32}P$ was measured by p81 method.

hBVR kinase assay: Kinase activity of hBVR was assayed as described earlier (Lerner-Marmarosh et al., "Human Biliverdin Reductase: A Member of the Insulin Receptor Substrate Family with Serine/Threonine/Tyrosine Kinase Activity," *Proc. Natl. Acad. Sci. U.S.A.* 102(20):7109-7114 (2005), which is hereby incorporated by reference in its entirety) in a reaction at pH8.4 containing $MnCl_2$, 0.2 mM DTT, and 10 μM $[\gamma-^{32}P]$-ATP; PKC-δ was tested as substrate.

Elk1-luciferase reporter assay: Cells were co-transfected with the reporters pFA2-Elk1, pFR-Luc (Stratagene, La Jolla, Calif.) and pCMV-β-galactosidase, and other plasmids, as necessary. Cells were lysed; promoter activity was determined by luciferase assay and normalized on β-galactosidase.

Statistical Analysis: Experiments were repeated three times unless otherwise indicated. Data in bar graphs are the means with standard deviations of three experiments, each with triplicate samples. Prism 3.0 software (GraphPad, San Diego, Calif.) was used for one-way ANOVA, from which Student's t was calculated for all sample pairs. Differences between experiments were not significant.

Example 7

Human BVR Increases the Autophosphorylation and Kinase Activity of PKC-δ

Figures 7A, 7B:
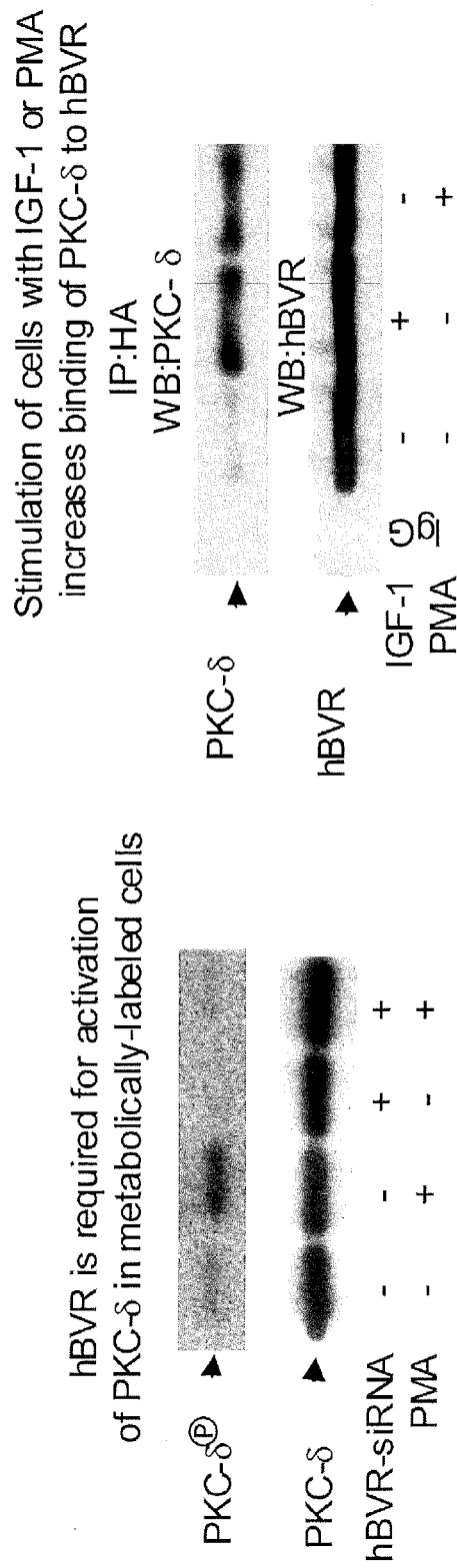
FIGS. 7A-7F show that PKC-δ autophosphorylation and activity are increased by hBVR. hBVR is required for activation of PKC-δ in metabolically-labeled cell as depicted in FIG. 7A. HEK293A cells were transfected with pcDNA-PKC-δ, then infected with virus expressing si-hBVR to deplete hBVR. Cells were starved for 24 h and metabolically labeled with [$^{32}$P]H$_3$PO$_4$ for another 4 h prior to treatment with PMA (100 nM, 15 min). Cell lysates were subjected to immunoprecipitation with anti-PKC-δ antibodies. After radioactive decay, the membrane was probed with the anti-PKC-δ antibodies as a reference for loading. Cell stimulation with IGF-1 or PMA increases binding of PKC-δ to hBVR as shown in FIG. 7B. Cells containing co-expressed pcDNA-HA-hBVR and pcDNA-PKC-δ plasmids were starved and treated with IGF-1 or PMA. Cell lysates were immunoprecipitated with anti-HA antibody followed by sequential immunoblotting with anti-PKC-δ and anti-hBVR antibodies.

To test whether the two kinases are linked, the effect of hBVR depletion on PKC-δ autophosphorylation was examined in cells that had been transfected with a PKC-δ expression plasmid and metabolically labeled with [$^{32}$P]-orthophosphate. As expected, treatment of such cells with 100 nM PMA resulted in a significant increase in incorporation of the label into PKC-δ (FIG. 7A). When, however, hBVR was depleted from the cells by treatment with si-hBVR virus, it was observed that the activation of PKC-δ was reduced, although it is apparent that there was no reduction in the absolute level of the PKC by si-hBVR treatment (FIG. 7A). Thus, activation of PKC-δ in response to PMA requires hBVR. It has previously been shown that hBVR activates PKC-ζ and MEK1/2-ERK1/2 by the formation of physical complexes with the target protein (Lerner-Marmarosh et al., "Human Biliverdin Reductase is an ERK Activator; hBVR is an ERK Nuclear Transporter and is Required for MAPK Signaling," *Proc. Natl. Acad. Sci. U.S.A.* 105(19):6870-6875 (2008), which is hereby incorporated by reference in its entirety). To test whether a complex is formed between PKC-δ and hBVR, cells were transfected with expression plasmids for PKC-δ and HA-tagged hBVR and subsequently treated with IGF-1 or PMA to activate PKC-δ. hBVR was immunoprecipitated from cell lysates with anti-HA antibody. Proteins in the immunoprecipitate were resolved by gel electrophoresis, and the western blot subsequently probed with antibodies to PKC-δ and hBVR. It is apparent that activation of PKC-δ by IGF-1 or PMA results in increased binding of the PKC to hBVR (FIG. 7B). A similar increase has been seen when the cells are stimulated with insulin.

Figures 7C, 7D:
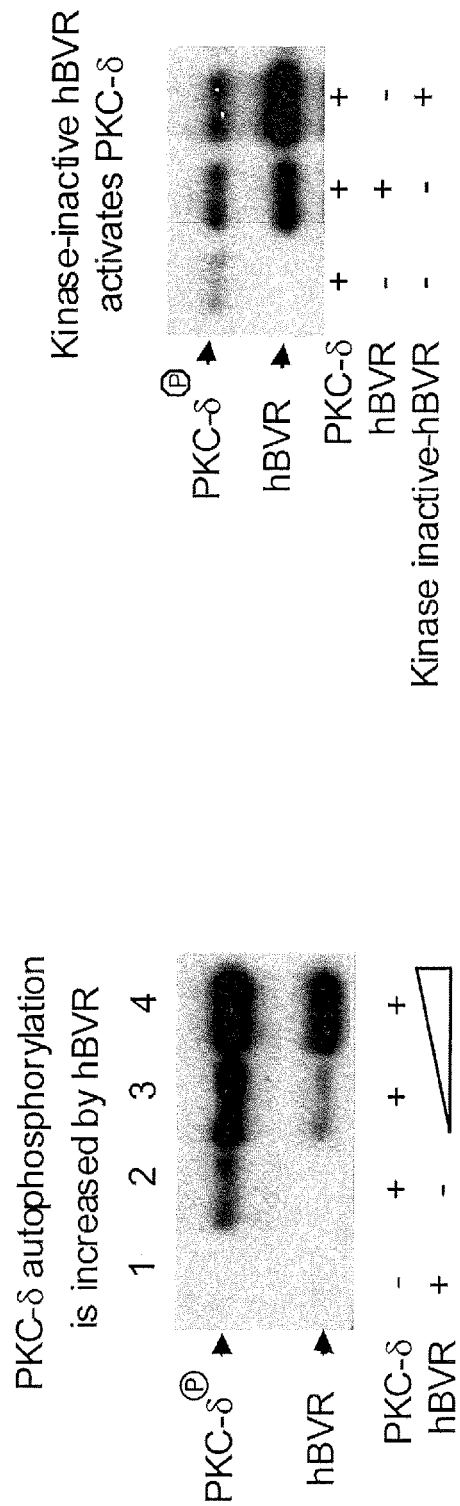
Figure 7F:
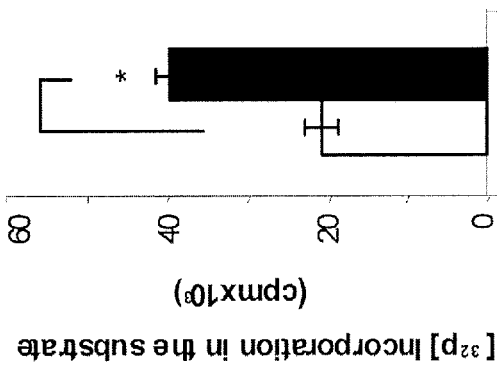
Figure 7E:
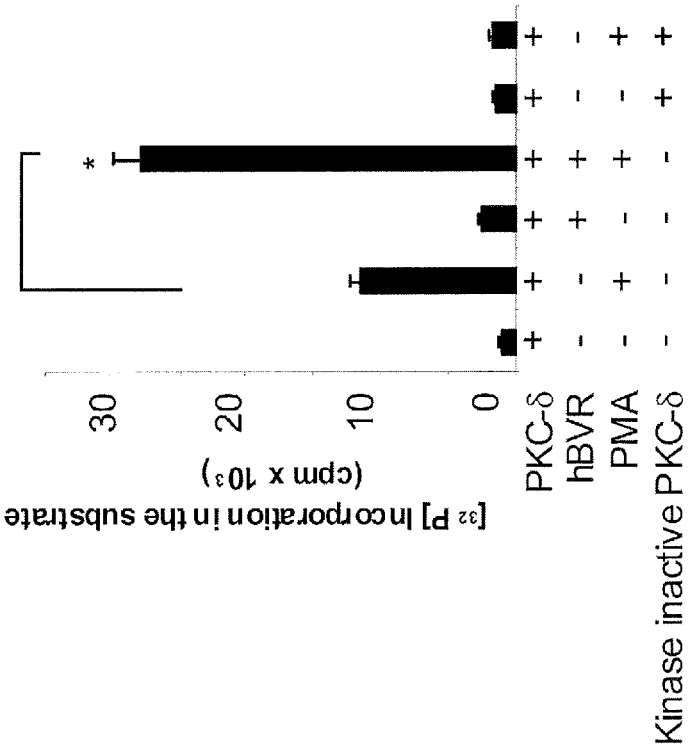

Study of the interaction between the two kinases was extended by an in vitro experiment that examined the effect of an increasing concentrations of hBVR added to PKC-δ and determined the incorporation of [$^{32}$P]-phosphate into PKC-δ by autophosphorylation. It is apparent, from comparison of lanes 3 and 4 in FIG. 7C with lane 2, that autophosphorylation of PKC-δ is increased in the presence of hBVR. Under the conditions employed in this reaction, which lacks Mn$^{2+}$, hBVR does not display kinase activity (lane 1). Moreover, there was significant incorporation of [$^{32}$P]-phosphate into hBVR in this experiment, further indicating that hBVR is itself a substrate for PKC-δ. The activation of PKC-δ by hBVR does not require that the latter be active. The activity of PKC-δ was examined in vitro in the presence of either wt or kinase-inactive (V$^{11-14}$, G$^{17}$-A) hBVR. It was found that both proteins activate the PKC (FIG. 7D) under reaction conditions that favor PKC activity, and moreover that both are good substrates. In a similar experiment, the activity of PKC-δ toward a commercially available PKC-δ substrate was assayed in the presence or absence of hBVR. PKC-δ or, as a control, kinase-inactive PKC-δ (K$^{378}$R) were overexpressed in the cells, together with hBVR as indicated in the FIG. 7E. The cells were then treated with PMA or vehicle (DMSO), lysed and immunoprecipitated with anti-PKC-δ antibody. The immunoprecipitates were then assayed for PKC-δ activity using a commercially available PKC-δ peptide substrate. There was a significant increase in the incorporation of label into substrate in the presence of hBVR (FIG. 7E)—indeed, there was also increased incorporation in the absence of treatment, as would be expected from the result observed in FIGS. 7C and 7D. Overexpression of the inactive mutant, as expected, ablated basal activity and further activation by PMA or hBVR. In a third experiment, any influence of extracellular activation was removed by transfecting cells with a constitutively active PKC-δ (Δ151-160). Co-transfection with hBVR expression plasmid resulted again in higher activity (FIG. 7F). Taken together, these data indicate that hBVR activation of PKC-δ in the cell is independent of both the basal activity of PKC-δ and the level of PKC protein.

Example 8

Figures 8C, 8D:
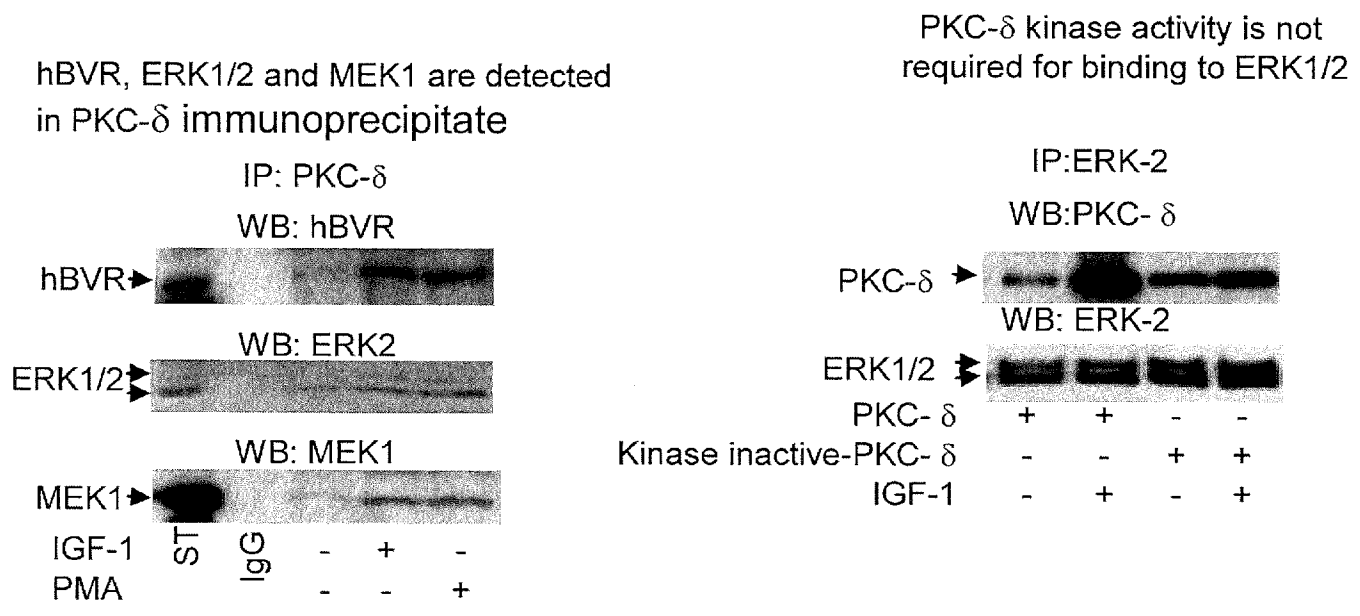
Figures 8E, 8F:
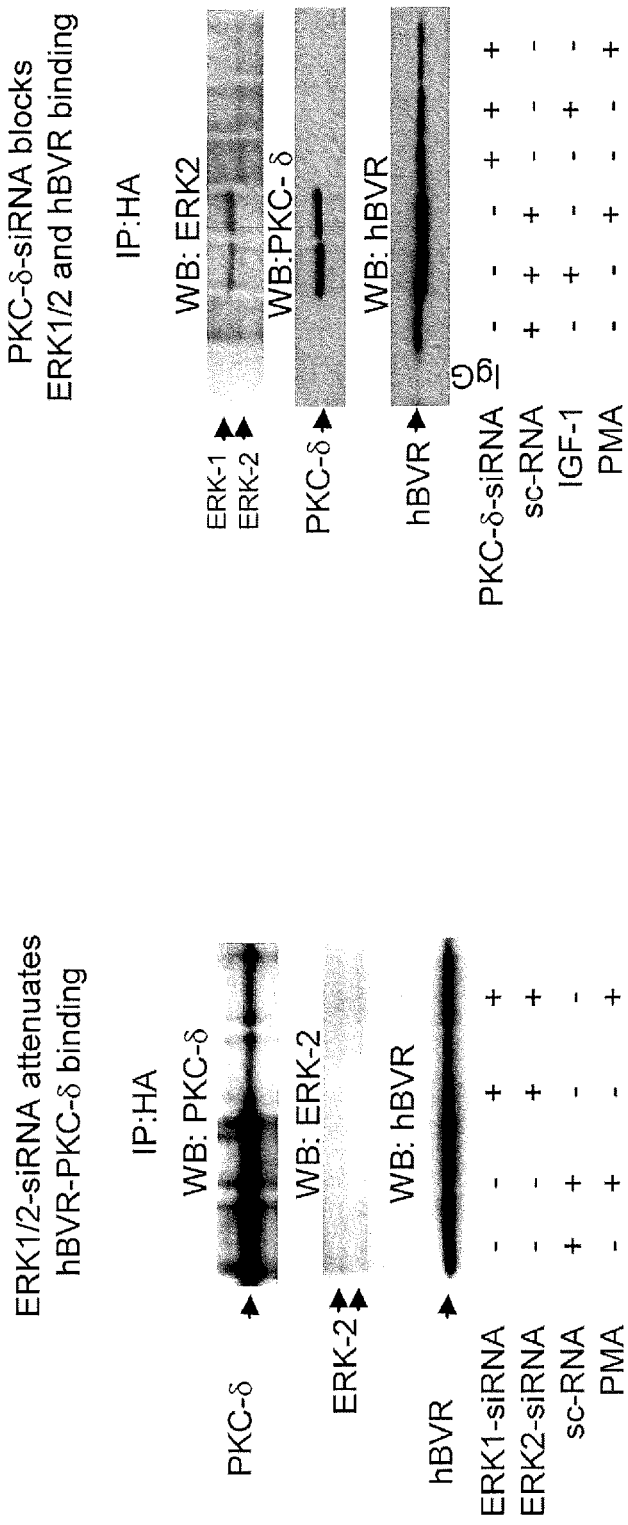

Complex Formation Between ERK1/2, PKC-δ, and hBVR hBVR was shown to regulate activation of ERK1/2 by MEK1 (Lerner-Marmarosh et al., "Human Biliverdin Reductase is an ERK Activator; hBVR is an ERK Nuclear Transporter and is Required for MAPK Signaling," *Proc. Natl. Acad. Sci. U.S.A.* 105(19):6870-6875 (2008), which is hereby incorporated by reference in its entirety) while PKC-δ was implicated in Ras/Raf/MEK/MAPK signaling pathways (Jackson et al., "The Enigmatic Protein Kinase Cdelta: Complex Roles in Cell Proliferation and Survival," *FASEB J.* 18(6):627-636 (2004), which is hereby incorporated by reference in its entirety). To examine interactions between hBVR, PKC-δ, and ERK1/2, cells were co-transfected with PKC-δ and HA-tagged hBVR plasmids, starved and treated either with IGF-1, PMA, or insulin. Cell lysates were immunoprecipitated with anti-HA antibody and subjected to western blotting with anti-ERK-1/2 followed by anti-PKC-δ and anti-hBVR antibodies. FIG. 8A indicates recovery of all three proteins from the immunoprecipitate after activation of PKC-δ, demonstrating that they form a ternary complex in response to the extracellular stimulus; insulin also increased the binding between three proteins. The role of hBVR in complex formation between PKC-δ and ERK1/2 was then explored. Again, cells were transfected with the PKC-δ expression plasmid; some of the cells were then treated with the hBVR si-RNA virus and some with control sc-RNA. After treatment with IGF-1, the cells were lysed, immunoprecipitated with anti-ERK1/2 antibody, and examined by western blot. The increased binding of PKC-δ to ERK1/2 was observed in the presence of sc-RNA (FIG. 8B), whereas the si-hBVR treatment almost completely eliminated binding, indicating a requirement for hBVR. To examine whether the interaction between hBVR, PKC-δ, and ERK1/2 is present endogenously, their association was also tested in cells in which neither protein was overexpressed (FIG. 8C). In this experiment, lysates were prepared from cells that had been treated with either IGF-1 or PMA and also from untreated cells. The lysates were immunoprecipitated with anti-PKC-δ antibodies and the immunoprecipitates were examined by western blotting. Treatment with IGF-1 or PMA led to a detectable increase in the level of hBVR associated with PKC-δ (FIG. 8C). It was also noted that both treatments resulted in increases in both ERK1/2 and MEK1 levels in the precipitates. These proteins have been previously shown to form a complex with hBVR (Lerner-Marmarosh et al., "Human Biliverdin Reductase is an ERK Activator; hBVR is an ERK Nuclear Transporter and is Required for MAPK Signaling," *Proc. Natl. Acad. Sci. U.S.A.* 105(19):6870-6875 (2008), which is hereby incorporated by reference in its entirety) in mitogen-stimulated cells, and it is apparent that PKC-δ is also part of this complex. Since there was no attempt made to overexpress the proteins, the endogenous protein levels are sufficient for complex formation. Interactions between ERK1/2 and PKC-δ were examined in cells transfected with either wt-PKC-δ or kinase-inactive PKC-δ and treated with IGF-1. The western blot of the immunoprecipitates with anti-ERK1/2 antibody (FIG. 8D) indicated that PKC-δ is present in the immune complex. Moreover, the intensity of the PKC-δ signal was increased in the immune complex after treatment with IGF-1. However, this increase in binding was not as pronounced when the inactive mutant (PKC-δ kinase-inactive) was used, indicating that binding is dependent, to a large extent, on activation of PKC-δ. It is also apparent that PKC-δ phosphorylates ERK1/2. In an in vitro reaction using conditions that are optimal for the PKC, phosphate was incorporated into kinase-inactive ERK1/2; this was not due to kinase-inactive-ERK1/2 autophosphorylation since no incorporation of the phosphate was seen in the sample containing kinase-inactive-ERK1/2 alone. These interactions then posed the question of whether ERK1/2 might modulate the interaction between hBVR and PKC-δ previously demonstrated in FIG. 7B. Accordingly, si-RNAs targeting ERK1 and ERK2 were used to deplete these proteins from cells overexpressing both PKC-δ and HA-BVR. Cells transfected with the inactive sc-RNA demonstrated the expected interaction of hBVR and PKC-δ, whereas the cells transfected with the ERK1/2 si-RNAs showed suppressed PKC-δ signal in the anti-HA immunoprecipitate (FIG. 8E). Previous studies have demonstrated that hBVR and ERK1/2 form an intracellular complex that is required for nuclear import of ERK1/2. In light of the observation that hBVR modulated PKC-δ binding to ERK1/2, whether PKC might mediate the hBVR-ERK1/2 interaction was tested. Cells were transfected with the HA-hBVR expression plasmid, and either si-RNA against PKC-δ or the appropriate sc-RNA control and treated with IGF-1 or PMA. Western blotting after immunoprecipitation with anti-HA antibody indicated that while the PKC-δ sc-RNA permitted hBVR-ERK1/2 complex formation, ablation of PKC-δ with si-RNA abolished the interaction (FIG. 8F). The data indicate that the three proteins are participating in a ternary complex such that depletion of hBVR or PKC-δ weakens formation of the complex.

Example 9

Figures 9A, 9B:
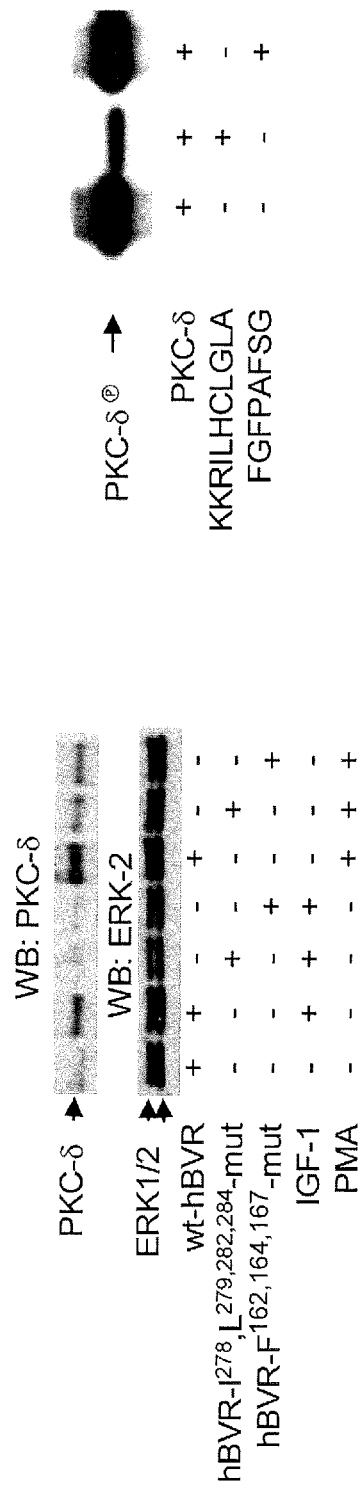
FIGS. 9A-9D show that hBVR hydrophobic motifs and D-box sequences participate in PKC-δ-ERK binding. Both the hydrophobic motif and D-box domains of hBVR are required for binding between PKC-δ and ERK-1/2 (FIG. 9A). Cells co-transfected with PKC-δ and either with wt hBVR or its C- and D-box mutants were starved and treated with either IGF-1 or PMA. Cell lysates were immunoprecipitated with anti-ERK-1/2 antibodies. Western blots of immunoprecipitates were probed by anti-PKC-δ followed by anti-ERK-1/2 antibodies.
Figures 9C, 9D:
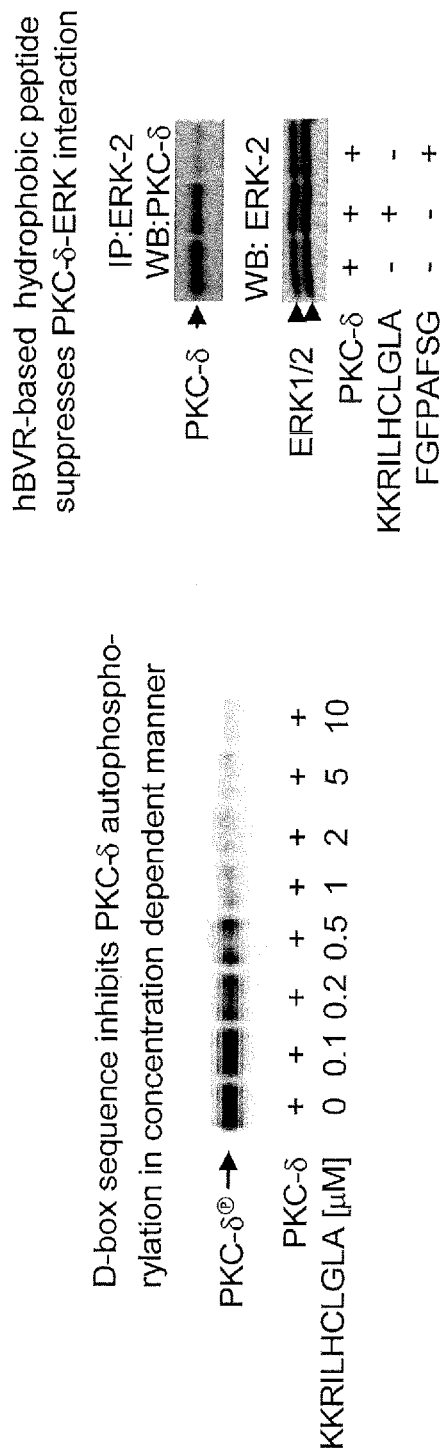

Interactions in the Ternary Complex are Mediated by hBVR Hydrophobic Domain and D-box (Hydrophobic) Sequences It has previously been demonstrated that activation of ERK1/2 by hBVR depends on the hydrophobic and D-box-like sequences found in hBVR (Lerner-Marmarosh et al., "Human Biliverdin Reductase is an ERK Activator; hBVR is an ERK Nuclear Transporter and is Required for MAPK Signaling," *Proc. Natl. Acad. Sci. U.S.A.* 105(19):6870-6875 (2008), which is hereby incorporated by reference in its entirety). To test the role of these motifs in the intact hBVR protein on the ternary complex formation, each sequence was mutated. The mutants, or wt hBVR, were overexpressed together with PKC-δ and the cells were stimulated with either IGF-1 or PMA. Irrespective of the nature of the stimulus, both mutants significantly suppressed complex formation (FIG. 9A), indicating that both motifs are required. The role of these sequence motifs in assembly of the ternary complex was further investigated using synthetic myristoylated peptides based on the hBVR protein. Both HA-hBVR and PKC-δ were overexpressed in cells; the myristoylated peptides were then added, and after 2 h, the cells were treated with IGF-1. The anti-HA immunoprecipitate revealed the expected association between hBVR and PKC-δ in the absence of peptide, and there was a slight decrease in binding when the D-box peptide, K$^{275}$KRILHCLGLA (SEQ ID NO:25), was added to the cells (FIGS. 9B and 9D). In contrast, the hydrophobic peptide, F$^{162}$GFPAFSG (SEQ ID NO:34), completely blocked the association between PKC-δ and hBVR (FIG. 9D). Similarly, in cells that overexpressed PKC-δ and were stimulated with IGF-1, immunoprecipitation with antibody against ERK-1/2 showed association of PKC-δ and ERK1/2. The D-box peptide failed to block this interaction whereas the hydrophobic peptide was inhibitory, indicating that the FGFP motif has a higher affinity than the D-Box sequence (FIG. 9D).

Example 10

Figure 10B:
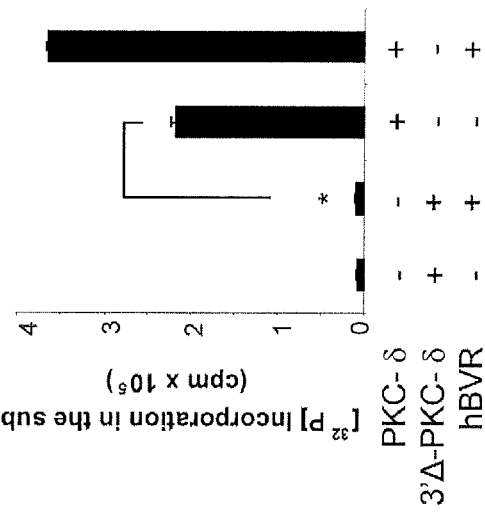
FIGS. 10A-10F demonstrate that PKC-δ Bulky Ring Motif is essential for its kinase activity but not for protein: protein interaction.
Figure 10A:
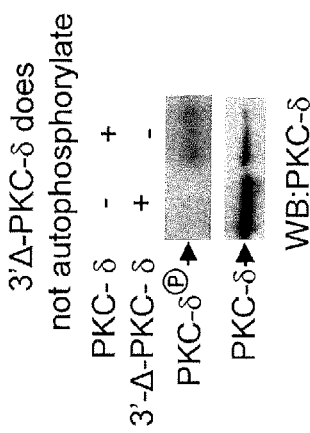
Figure 10D:
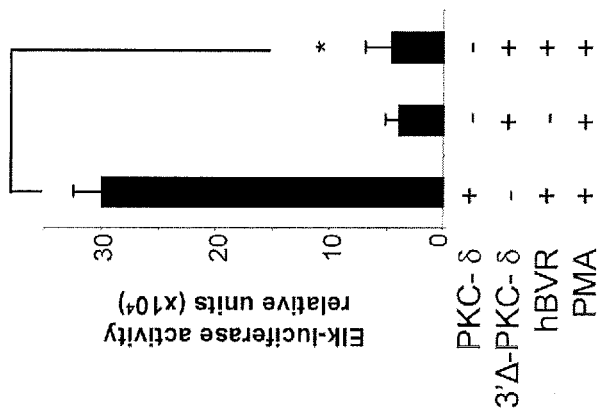
Figure 10C:
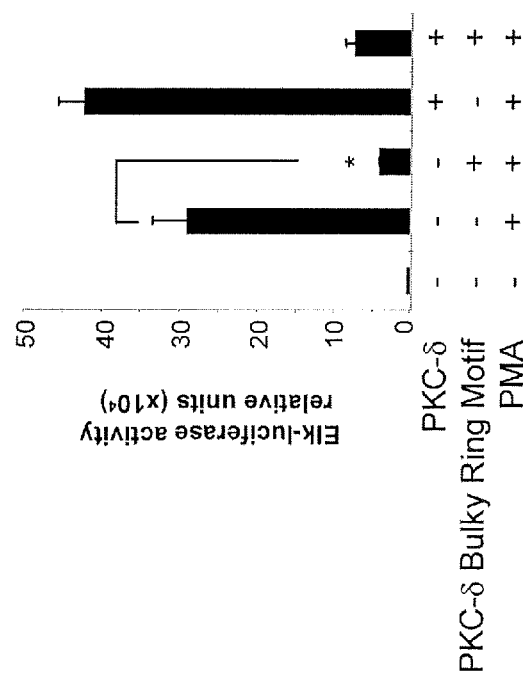
Figures 10E, 10F:
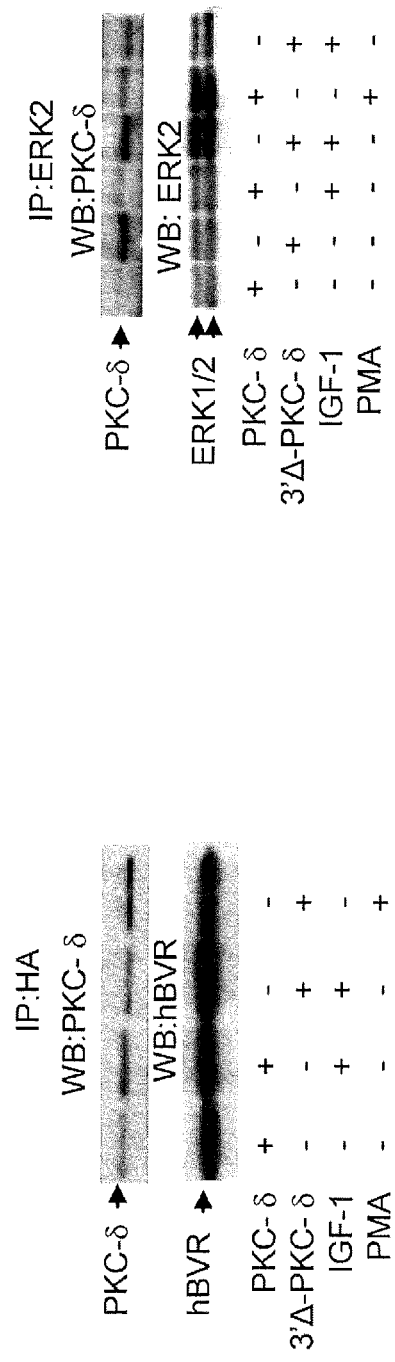

PKC-δ Bulky Ring Motif is Essential for its Kinase Activity but not for Protein:Protein Interaction Because of the possibility that a sequence in the C-terminus of PKC-δ, F$^{660}$AGFSF (SEQ ID NO: 61), might be functioning as a binding site for protein:protein interaction, expression vectors were constructed in which the 21 amino acids of the C-terminus (amino acid residues 656-676) of PKC-δ were deleted. In vitro, the deletion protein caused a lack of autophosphorylation (FIG. 10A) and also lacked kinase activity toward the MBP substrate as compared to wt PKC-δ enzyme (FIG. 10B). Furthermore, a peptide containing the C-terminal 19 amino acids of PKC-δ suppressed PMA-dependent activation of Elk1. In control PMA-treated cells, the peptide inhibited Elk1 dependent luciferase expression by 90% (FIG. 10C); overexpression of PKC-δ in the presence of the peptide did not rescue PMA-dependent activation of transcription. These data demonstrate that the peptide is competing with PKC-δ for a binding site and, thus, that the C-terminus of the protein mediates protein:protein interaction. In a system in which wildtype PKC-δ is overexpressed, the inclusion of hBVR causes a significant increase in the activation of the luciferase reporter (FIG. 10D). By contrast, overexpression of the PKC-δ 3'-deletion mutant results in vastly reduced reporter activity in response to PMA and the presence of hBVR did not increase this low activity level. Although the C-terminus of PKC-δ was necessary for its kinase activity, it was neither required for binding to hBVR (FIG. 10E) nor to ERK1/2 (FIG. 10F).

Example 11 hBVR is an Important Partner in MEK1/2-ERK1/2-Elk1 Transcriptional Activation

In previous studies, two ternary complexes involving hBVR and ERK1/2 were observed in the signaling pathway that results eventually in Elk1 dependent transcription (Lerner-Marmarosh et al., "Human Biliverdin Reductase is an ERK Activator; hBVR is an ERK Nuclear Transporter and is Required for MAPK Signaling," *Proc. Natl. Acad. Sci. U.S.A.* 105(19):6870-6875 (2008), which is hereby incorporated by reference in its entirety). The first complex includes MEK1/2, and it was noted that the formation of the complex stimulated the activities of both MEK and ERK1/2. hBVR mediated transport of ERK 1/2 to the nucleus, where a new complex was formed that also included Elk1, resulting in its phosphorylation and activation. To assess further hBVR and PKC-δ's roles in the activation of this pathway, a series of experiments were carried out using a luciferase reporter assay to measure Elk1-dependent transcription. In these experiments cells were transfected with the luciferase reporters, together with the control sc-RNA or siRNA against MEK1/2, PKC-δ, or hBVR. Cells treated with the si-hBVR virus showed a 70-80% decrease in PMA-induced transcriptional activation compared with cells infected with the inactive scRNA (FIG. 11A). An almost identical observation was made if PKC-δ siRNA was used to transfect the cells (FIG. 11B), indicating a prominent role for PKC-δ in a signal transduction pathway leading to Elk1 activation. Addition of MEK1/2 siRNA significantly suppressed (by 65%) Elk1 activation after PMA treatment (FIG. 11C). If si-hBVR and PKC-δ siRNA were included together with MEK1/2 siRNA, there was a further reduction in activity, resulting in 80% reduction compared to a sample treated with the control sc-RNA. This finding is expected given the previously described role of hBVR in MEK/ERK/Elk1 signaling (Lerner-Marmarosh et al., "Human Biliverdin Reductase is an ERK Activator; hBVR is an ERK Nuclear Transporter and is Required for MAPK Signaling," *Proc. Natl. Acad. Sci. U.S.A.* 105(19):6870-6875 (2008), which is hereby incorporated by reference in its entirety).

Discussion of Examples 7-11

Two distinct pathways lead to the activation of ERK1/2: MAPK/MEK1 and PKC-δ. Previously defined was the essential role of hBVR in the MEK1-dependent activation of ERK1/2 signal transduction (Lerner-Marmarosh et al., "Human Biliverdin Reductase is an ERK Activator; hBVR is an ERK Nuclear Transporter and is Required for MAPK Signaling," *Proc. Natl. Acad. Sci. U.S.A.* 105(19):6870-6875 (2008), which is hereby incorporated by reference in its entirety). The data herein defines a requirement for PKC-δ-mediated ERk1/2 activation and formation of a ternary complex between PKC-δ/ERK1/2/hBVR. The preceding Examples confirm that hBVR plays a crucial role in regulation of ERK 1/2 regulated signal transduction by functioning as the ERK1/2-kinase-anchoring protein and positioning the phosphorecepter residues of ERK 1/2 in proximity of its activator kinases. This conclusion is consistent with the observation that when both MEK1/2 and ERK1/2 expressions are silenced, only a modest activation of ERK1/2 is detected in PMA stimulated cells.

Although PKC-δ is generally considered a lipid-regulated kinase, an additional mechanism for PKC-δ activation in the cell that is independent of membrane lipids and involves tyrosine phosphorylation by Src family kinases in response to oxidative stress has been reported (Steinberg SF, "Distinctive Activation Mechanisms and Functions for Protein Kinase Cdelta," *Biochem. J* 384(Pt 3):449-459 (2004), which is hereby incorporated by reference in its entirety). hBVR is among several downstream targets of IRK and is tyrosine phosphorylated by insulin-/IGF-1-stimulated kinase (Lerner-Marmarosh et al., "Human Biliverdin Reductase is an ERK Activator; hBVR is an ERK Nuclear Transporter and is Required for MAPK Signaling," *Proc. Natl. Acad. Sci. U.S.A.* 105(19):6870-6875 (2008), which is hereby incorporated by reference in its entirety). Tyrosine residues $Y^{198}$ MKM (SEQ ID NO: 68) and $Y^{228}$ LSF (SEQ ID NO: 69) sequences are substrates for insulin/IGF-1-activated IRK. Those sequences correspond to the consensus motif of the docking sites in adapter proteins for the recruitment of Src-homology (SH2) binding proteins upstream of MAPK and the PI3K branches of IRK signaling pathway (Pawson et al., "Signaling Through Scaffold, Anchoring, and Adaptor Proteins," *Science* 278(5346):2075-2080 (1997), which is hereby incorporated by reference in its entirety). Moreover, there is evidence for direct binding between ERK and PKCε, also a novel PKC form, in the mouse heart where cardio-protection afforded by activation of MAPK is dependent upon functional PKC-ε(Baines et al., "Mitochondrial PKCepsilon and MAPK Form Signaling Modules in the Murine Heart: Enhanced Mitochondrial PKCepsilon-MAPK Interactions and Differential MAPK Activation in PKCepsilon-Induced Cardioprotection," *Circ. Res.* 90(4):390-397 (2002), which is hereby incorporated by reference in its entirety). Similarly, there is precedent for ERK1/2 activation by a MEK1/2-independent mechanism (Tapinos et al., "Insights into Regulation of Human Schwann Cell Proliferation by Erk1/2 via a MEK-Independent and p56Lck-Dependent Pathway from Leprosy Bacilli," *Proc. Natl. Acad. Sci. U.S.A.* 102(26):9188-9193 (2005), which is hereby incorporated by reference in its entirety). The characterized role of hBVR in ERK1/2 activation is not intended to suggest that ERK1/2 cannot be activated by kinases and pathways that are independent of hBVR. It is likely that the residual ERK1/2 activation noted, despite silencing MEK1/2, PKC-δ and hBVR, is due to input by additional upstream kinases in the insulin/IGF-1/MAPK/IP-3K signaling network that function independent of hBVR.

Data obtained with kinase-inactive hBVR and the hydrophobic hBVR-based peptide indicate the likelihood that hBVR activation of PKC-δ involves the allosteric mechanism and conformational change in PKC, causing exposure of its catalytic pocket, exposure of new sites, and/or interference with protein:protein interface. This mechanism of activation would be analogues to how membrane lipids activate lipid-regulated PKCs. PKC-δ, like other members of the novel types of PKCs, is activated by interaction with membrane lipids, which induce conformational change, release of the inhibitory pseudo-substrate form the substrate binding site, and catalytic maturation (Newton AC, "Protein Kinase C: Poised to Signal," *Am. J. Physiol. Endocrinol. Metab.* 298(3):E395-402 (2010), which is hereby incorporated by reference in its entirety). In the cell, hBVR-peptide may also function as an allosteric regulator of the PKC. Phosphorylation of T505, Y512, and Y223 in the activation loop of PKC-δ are necessary for catalytic activation of the PKC. Although hBVR is a S/T/Y kinase (Lerner-Marmarosh, et al., "Human Biliverdin Reductase: a Member of the Insulin Receptor Substrate Family with Serine/Threonine/Tyrosine Kinase Activity," *Proc. Natl. Acad. Sci. U.S.A.* 102(20):7109-7114 (2005), which is hereby incorporated by reference in its entirety), finding that the PKC is activated by the kinase-inactive hBVR indicates that the PKC is not a substrate for hBVR.

PKC-δ can also be activated in the cell independent of interaction with membrane lipids, via tyrosine phosphorylation by Src family kinases in response to oxidative stress (Steinberg SF, "Distinctive Activation Mechanisms and Functions for Protein Kinase Cdelta," *Biochem. J.* 384(Pt 3):449-459 (2004), which is hereby incorporated by reference in its entirety). Oxygen free radicals also activate hBVR (Salim et al., "Human Biliverdin Reductase is Autophosphorylated, and Phosphorylation is Required for Bilirubin Formation," *J. Biol. Chem.* 276(14):10929-10934 (2001), which is hereby incorporated by reference in its entirety). In cells exposed to oxidative stress, the tyrosine phosphorylated activated PKC-δ accumulates in the soluble fraction, where hBVR is localized, and phosphorylates target substrates. NF-κB signaling pathway is a cytoplasmic target of both activated PKC-δ and hBVR (Yamaguchi et al., "Protein Kinase C Delta Activates IkappaB-Kinase Alpha to Induce the p53 Tumor Suppressor in Response to Oxidative Stress," *Cell Signal.* 19(10):2088-2097 (2007); Gibbs et al., "Characterization of the Human Biliverdin Reductase Gene Structure and Regulatory Elements: Promoter Activity is Enhanced by Hypoxia and Suppressed by TNF-{Alpha}-Activated NF-{Kappa}B," *FASEB J.* (2010), which are hereby incorporated by reference in their entirety).

The data herein demonstrates that PKC-δ binding occurs with high degree of specificity with respect to hBVR primary structural features and does not involve non-specific protein:protein binding at the C-terminal β sheet of hBVR. This assertion is supported by findings with the hBVR constructs carrying mutations in the hydrophobic sequence corresponding to the core of C-Box and in the sequence corresponding to D-Box motif and leucine-rich D-Box (Jacobs et al., "Multiple Docking Sites on Substrate Proteins Form a Modular System that Mediates Recognition by ERK MAP Kinase," *Genes Dev.* 13(2):163-175 (1999); Minden et al., "Regulation and Function of the JNK Subgroup of MAP Kinases," *Biochim. Biophys. Acta* 1333(2):F85-104 (1997), which are hereby incorporated by reference in their entirety) that have pointed to the participation of those specific sites in the scaffolding function of hBVR. These findings do not support hydrogen bonding at the interface of C-terminal β-sheet of hBVR:PKC-δ or hBVR: ERK1/2 as the sole mode of interactions. It is further proposed that the hydrophobic sequence of hBVR is strictly relegated to interaction with ERK1/2, while the D-Box sequence is the interaction site with MEK1 or PKC-δ. This notion is consistent with the present findings and the previous characterization of interaction of hBVR with MEK1-activated ERK1/2. The present findings do not allow assignment of order and/or affinity of the sequence for the ERK1/2 kinases, MEK1, and PKC-δ. That the kinase-inactive hBVR is as effective in providing a docking site for the interactive partner kinases as the native protein is supportive of this reasoning. This argument is strengthened by inhibitory effect of the hydrophobic C-Box-like peptide on binding of hBVR-ERK1/2 binding and D-Box-like peptide on hBVR-PKC-δ interaction. Conformational distortion of binding pocket and interference at protein:protein interface could account for the inhibitions. It is likely that the anchoring function of hBVR is perhaps as or more relevant to its role in transduction of signals than its kinase activity. Signal transduction by all PKC isotypes is linked to their subcellular locations. hBVR differs from PDZ-type scaffolding proteins, which are nearly always found in the cytoplasm, by not being exclusively cytoplasmic; it is found in other organelles, including the nucleus and mitochondria (Nowell et al., "Identification of Enzymes Responsible for the Metabolism of Heme in Human Platelets," *J. Biol. Chem.* 273(50):33342-33346 (1998); Tudor et al., "Biliverdin Reductase is a Transporter of Haem into the Nucleus and is Essential for Regulation of HO-1 Gene Expression by Haematin," *Biochem. J.* 413(3):405-416 (2008), which are hereby incorporated by reference in their entirety).

Not only is hBVR a key component for ERK1/2 phosphorylation/activation, be it by MEK1 or PKC-δ, but based on the available information, it is the only vehicle for nuclear import and export of ERK1/2. Although there are reports that PKC-δ is found in the nucleus of insulin-treated cells (Horovitz-Fried et al., "Activation of the Nuclear Transcription Factor SP-1 by Insulin Rapidly Increases the Expression of Protein Kinase C Delta in Skeletal Muscle," *Cell Signal.* 19(3):556-562 (2007); Horovitz-Fried et al., "Insulin Increases Nuclear Protein Kinase Cdelta in L6 Skeletal Muscle Cells," *Endocrinology* 149(4):1718-1727 (2008), which are hereby incorporated by reference in their entirety), and its nuclear localization is required for apoptosis, to date there is no evidence to suggest a role for PKC-δ in ERK1/2 nuclear transport. It is suggested herein, that the nuclear localization signal (NLS) and nuclear export signal (NES) motifs of hBVR are essential for transport of ERK1/2 into and out of the nucleus (Lerner-Marmarosh et al., "Human Biliverdin Reductase is an ERK Activator; hBVR is an ERK Nuclear Transporter and is Required for MAPK Signaling," *Proc. Natl. Acad. Sci. U.S.A.* 105:6870-6875 (2008), which is hereby incorporated by reference in its entirety); ERK dimers require a transporter with a functional NLS to translocate to the nucleus. Although hBVR may not be the sole transporter of ERK1/2 into the nucleus, it certainly has that capacity.

There appears to be a considerable degree of sequence specificity to the motif that binds PKC-δ and ERK1/2, because the hydrophobic Bulky Ring motif of PKC-δ (FXXFXF; SEQ ID NO:62), which is similar in its hydrophobicity profile to the phenylalanine-rich motif of hBVR (FXFXXF; SEQ ID NO: 63), is not required for either hBVR or ERK1/2 binding. Indeed, the C-terminal truncated PKC-δ carrying a deletion of the last 21 residues did not affect its binding to hBVR or ERK1/2. The C-terminal-truncated PKC-δ that houses $Ser^{662}$, however, is neither kinase active nor is it activated by hBVR.

The outcome of modulation of ERK1/2 and PKC-δ by hBVR can be considered in the context of the ternary complex formation as well as at an individual level. With respect to ERK1/2, hBVR's input in the cell signaling cascade that leads to activation of ERK1/2, and itself is activated upon stimulation of the MAPK pathways, integrates functions of hBVR in promoting cell growth proliferation via activation of ERK1/2 signaling and cell survival by attenuating apoptosis by producing bilirubin (Boutros et al., "Mitogen-Activated Protein (MAP) Kinase/MAP Kinase Phosphatase Regulation: Roles in Cell Growth, Death, and Cancer," *Pharmacol. Rev.* 60(3):261-310 (2008); Buder-Hoffmann et al., "A Protein Kinase Cdelta-Dependent Protein Kinase D Pathway Modulates ERK1/2 and JNK1/2 Phosphorylation and Bim-Associated Apoptosis by Asbestos," *Am. J. Pathol.* 174(2):449-459 (2009), which are hereby incorporated by reference in their entirety). Because of the outcome of activation of ERK1/2 pathway, finding that a 7-residue hBVR-based peptide inhibits activation of ERK1/2 by PKC-δ should have practical applicability when seeking to attenuate tumor growth.

It has previously been shown that hBVR's kinase and reductase activities are linked. That is when stimulated by stress-inducing factors such as $H_2O_2$, sodium arsenite, or TNF-α, its reductase activity increases along with production of the antioxidant, bilirubin, the quencher of pro-apoptotic oxygen and NO radicals (Stocker et al., "Bilirubin is an Antioxidant of Possible Physiological Importance," *Science* 235(4792):1043-1046 (1987); Kaur et al., "Interaction of Bilirubin and Biliverdin with Reactive Nitrogen Species," *FEBS Lett.* 543(1-3):113-119 (2003); Mancuso et al., "Bilirubin: an Endogenous Scavenger of Nitric Oxide and Reactive Nitrogen Species," *Redox Rep.* 11(5):207-213 (2006); Shiva et al., "Redox Signalling: From Nitric Oxide to Oxidized Lipids," *Biochem. Soc. Symp.* (71):107-120 (2004); Hill et al., "What Part of NO Don't You Understand? Some Answers to the Cardinal Questions in Nitric Oxide Biology," *J. Biol. Chem.* 285(26):19699-19704 (2010), which are hereby incorporated by reference in their entirety). The radicals arise in vivo as the product of endogenous sources and result in activation of stress-response genes, including HO-1. Not only bilirubin, but also CO, which is produced at equimolar amounts by heme oxygenase activity, are active constituents of cellular defense mechanisms (Kaur et al., "Interaction of Bilirubin and Biliverdin with Reactive Nitrogen Species," *FEBS Lett.* 543(1-3):113-119 (2003); Li Volti et al., "Role of Carbon Monoxide and Biliverdin in Renal Ischemia/Reperfusion Injury," *Nephron Exp. Nephrol.*

104(4):e135-139 (2006); Li Volti et al., "Pharmacological Induction of Heme Oxygenase-1 Inhibits iNOS and Oxidative Stress in Renal Ischemia-Reperfusion Injury," *Transplant Proc.* 39(10):2986-2991 (2007), which are hereby incorporated by reference in their entirety). hBVR regulates HO-1 at the transcription level and HO-2 at protein turnover/stability level (Ding et al., "The Coordinated Increased Expression of Biliverdin Reductase and Heme Oxygenase-2 Promotes Cardiomyocyte Survival; a Reductase-Based Peptide Counters Beta-Adrenergic Receptor Ligand-Mediated Cardiac Dysfunction," *FASEB J. In press* (2010), which is hereby incorporated by reference in its entirety).

A variety of functions have been attributed to PKC-δ. For instance, both pro- and anti-apoptotic effects of the PKC have been reported. Generally it is agreed that the kinase is a regulator of cell growth, which may in part reflect its phosphorylation of the elongation factor eEF-1α (Kielbassa et al., "Protein Kinase C Delta-Specific Phosphorylation of the Elongation Factor eEF-Alpha and an eEF-1 Alpha Peptide at Threonine 431," *J. Biol. Chem.* 270(11):6156-6162 (1995), which is hereby incorporated by reference in its entirety), and its role in glucose-dependent signaling (Ramana et al., "Aldose Reductase-Regulated Tumor Necrosis Factor-Alpha Production is Essential for High Glucose-Induced Vascular Smooth Muscle Cell Growth," *Endocrinology* 148(9):4371-4384 (2007), which is hereby incorporated by reference in its entirety). Its activation can lead to cell differentiation (O'Driscoll et al., "Selective Translocation of Protein Kinase C-Delta in PC12 Cells During Nerve Growth Factor-Induced Neuritogenesis," *Mol. Biol. Cell.* 6(4):449-458 (1995), which is hereby incorporated by reference in its entirety), cell division arrest (Watanabe et al., "Cell Division Arrest Induced by Phorbol Ester in CHO Cells Overexpressing Protein Kinase C-Delta Subspecies," *Proc. Natl. Acad. Sci. U.S.A.* 89(21):10159-10163 (1992), which is hereby incorporated by reference in its entirety), or slowed cell growth (Brooks et al., "Growth of Melanocytic Cells is Associated with Down-Regulation of Protein Kinase C Alpha, Delta, and Epsilon Isoforms. Possible Role of Diacylglycerol," *J. Biol. Chem.* 268(32):23868-23875 (1993), which is hereby incorporated by reference in its entirety). Therefore, the relevance of the transactivation of hBVR and PKC-δ can reasonably be expected to extend to cellular functions beyond activation of ERK1/2 signaling.

In addition, activation of PKC-δ by hBVR is considered relevant in a disease context, and in therapeutic settings that are associated with PKC-δ activity. For instance PKC-δ deficient mice display immune-complex-type glomerulonephritis and lymphocyte infiltration of organs (Miyamoto et al., "Increased Proliferation of B Cells and Auto-Immunity in Mice Lacking Protein Kinase Cdelta." *Nature* 416(6883):865-869 (2002), which is hereby incorporated by reference in its entirety). Kinase activity of hBVR as a factor in the development of immune-complex-type glomerulonephritis that accompanies Goodpasture syndrome, the syndrome is caused by disruption of basement membrane of nephrons, was recently identified (Miralem et al., "Human Biliverdin Reductase Suppresses Goodpasture Antigen-Binding Protein (GPBP) Kinase Activity: the Reductase Regulates Tumor Necrosis Factor-Alpha-NF-KappaB-Dependent GPBP Expression," *J. Biol. Chem.* 285(17):12551-12558 (2010), which is hereby incorporated by reference in its entirety). Accordingly, it is reasonable to consider a causal relationship between the PKC and the reductase in the manifestation of glomerulonephritis.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated peptide consisting of the amino acid sequence selected from the group consisting of GL [K/R][K/R]N[K/R][F/Y/W]L[S/T][F/Y/W][K/R/H][F/Y/W][K/R][S/T] (SEQ ID NO :44) and myristolated SEQ ID NO: 44.

2. The isolated peptide of claim 1, wherein the peptide is GLKRNRYLSFHFKS (SEQ ID NO: 45).

3. An isolated peptide consisting of an amino acid sequence selected from the group consisting of [K/R][K/R]N[K/R]Y[L/I]S[F/W] (SEQ ID NO: 18) and myristolated SEQ ID NO: 18.

4. The isolated peptide of claim 3, wherein the peptide is KRNRYLSF (SEQ ID NO: 19).

5. An isolated peptide consisting of the amino acid sequence selected from the group consisting of FXFPXF[S/T]G (SEQ ID NO: 33) and myristolated SEQO ID NO: 33, wherein X at amino acid positions 2 and 5 is any amino acid.

6. A pharmaceutical composition comprising the isolated peptide of claim 1 and a pharmaceutically acceptable carrier.

7. The pharmaceutical composition of claim 6 further comprising a delivery vehicle.

8. A pharmaceutical composition comprising the isolated peptide of claim 3 and a pharmaceutically acceptable carrier.

9. The pharmaceutical composition of claim 8 further comprising a delivery vehicle.

10. A pharmaceutical composition comprising the isolated peptide of claim 5 and a pharmaceutically acceptable carrier.

11. The pharmaceutical composition of claim 10 further comprising a delivery vehicle.

* * * * *

SEQUENCE LISTING

```
<160> NUMBER OF SEQ ID NOS: 70

<210> SEQ ID NO 1
<211> LENGTH: 296
<212> TYPE: PRT
<213> ORGANISM: Homo sapien

<400> SEQUENCE: 1

Met Asn Ala Glu Pro Glu Arg Lys Phe Gly Val Val Val Gly Val
1               5                   10                  15

Gly Arg Ala Gly Ser Val Arg Met Arg Asp Leu Arg Asn Pro His Pro
            20                  25                  30

Ser Ser Ala Phe Leu Asn Leu Ile Gly Phe Val Ser Arg Arg Glu Leu
        35                  40                  45

Gly Ser Ile Asp Gly Val Gln Gln Ile Ser Leu Glu Asp Ala Leu Ser
    50                  55                  60

Ser Gln Glu Val Glu Val Ala Tyr Ile Cys Ser Glu Ser Ser Ser His
65                  70                  75                  80

Glu Asp Tyr Ile Arg Gln Phe Leu Asn Ala Gly Lys His Val Leu Val
                85                  90                  95

Glu Tyr Pro Met Thr Leu Ser Leu Ala Ala Ala Gln Glu Leu Trp Glu
            100                 105                 110

Leu Ala Glu Gln Lys Gly Lys Val Leu His Glu Glu His Val Glu Leu
        115                 120                 125
```

```
Leu Met Glu Glu Phe Ala Phe Leu Lys Lys Glu Val Val Gly Lys Asp
    130                 135                 140
Leu Leu Lys Gly Ser Leu Leu Phe Thr Ser Asp Pro Leu Glu Glu Asp
145                 150                 155                 160
Arg Phe Gly Phe Pro Ala Phe Ser Gly Ile Ser Arg Leu Thr Trp Leu
                165                 170                 175
Val Ser Leu Phe Gly Glu Leu Ser Leu Val Ser Ala Thr Leu Glu Glu
                180                 185                 190
Arg Lys Glu Asp Gln Tyr Met Lys Met Thr Val Cys Leu Glu Thr Glu
                195                 200                 205
Lys Lys Ser Pro Leu Ser Trp Ile Glu Glu Lys Gly Pro Gly Leu Lys
    210                 215                 220
Arg Asn Arg Tyr Leu Ser Phe His Phe Lys Ser Gly Ser Leu Glu Asn
225                 230                 235                 240
Val Pro Asn Val Gly Val Asn Lys Asn Ile Phe Leu Lys Asp Gln Asn
                245                 250                 255
Ile Phe Val Gln Lys Leu Leu Gly Gln Phe Ser Glu Lys Glu Leu Ala
                260                 265                 270
Ala Glu Lys Lys Arg Ile Leu His Cys Leu Gly Leu Ala Glu Glu Ile
    275                 280                 285
Gln Lys Tyr Cys Cys Ser Arg Lys
    290                 295

<210> SEQ ID NO 2
<211> LENGTH: 1070
<212> TYPE: DNA
<213> ORGANISM: Homo sapiens

<400> SEQUENCE: 2
ggggtggcgc ccggagctgc acggagagcg tgcccgtcag tgaccgaaga agagaccaag      60
atgaatgcag agcccgagag gaagtttggc gtggtggtgg ttggtgttgg ccgagccggc     120
tccgtgcgga tgagggactt gcggaatcca cacccttcct cagcgttcct gaacctgatt     180
ggcttcgtgt cgagaaggga gctcgggagc attgatggag tccagcagat ttctttggag     240
gatgctcttt ccagccaaga ggtggaggtc gcctatatct gcagtgagag ctccagccat     300
gaggactaca tcaggcagtt ccttaatgct ggcaagcacg tccttgtgga atacccatg      360
acactgtcat tggcggccgc tcaggaactg tgggagctgg ctgagcagaa aggaaaagtc     420
ttgcacgagg agcatgttga actcttgatg gaggaattcg cttttcctgaa aaagaagtg     480
gtggggaaag acctgctgaa agggtcgctc ctcttcacat ctgacccgtt ggaagaagac     540
cggtttggct tccctgcatt cagcggcatc tctcgactga cctggctggt ctccctcttt     600
ggggagcttt ctcttgtgtc tgccactttg gaagagcgaa aggaagatca gtatatgaaa     660
atgacagtgt gtctggagac agaagagaaa agtccactgt catggattga agaaaaagga     720
cctggtctaa aacgaaacag atatttaagc ttccatttca gtctgggtc cttggagaat     780
gtgccaaatg taggagtgaa taagaacata tttctgaaag atcaaaatat atttgtccag     840
aaactcttgg gccagttctc tgagaaggaa ctggctgctg aaaagaaacg catcctgcac     900
tgcctggggc ttgcagaaga aatccagaaa tattgctgtt caaggaagta agaggaggag     960
gtgatgtagc acttccaaga tggcaccagc atttggttct tctcaagagt tgaccattat    1020
ctctattctt aaaattaaac atgttgggga acaaaaaaaa aaaaaaaaaa                1070
```

```
<210> SEQ ID NO 3
<211> LENGTH: 296
<212> TYPE: PRT
<213> ORGANISM: Sus domesticus

<400> SEQUENCE: 3

Met Asn Ala Glu Pro Glu Arg Lys Phe Gly Val Val Val Gly Val
1               5                   10                  15

Gly Arg Ala Gly Ser Val Arg Met Arg Asp Leu Arg Asn Pro His Pro
            20                  25                  30

Ser Ser Ala Phe Leu Asn Leu Ile Gly Phe Val Ser Arg Arg Glu Leu
        35                  40                  45

Gly Ser Ile Asp Gly Val Gln Gln Ile Ser Leu Glu Asp Ala Leu Ser
    50                  55                  60

Ser Gln Glu Val Glu Val Ala Tyr Ile Cys Ser Glu Ser Ser His
65                  70                  75                  80

Glu Asp Tyr Ile Arg Gln Phe Leu Asn Ala Gly Lys His Val Leu Val
                85                  90                  95

Glu Tyr Pro Met Thr Leu Ser Leu Ala Ala Gln Glu Leu Trp Glu
            100                 105                 110

Leu Ala Glu Gln Lys Gly Lys Val Leu His Glu Glu His Val Glu Leu
        115                 120                 125

Leu Met Glu Glu Phe Ala Phe Leu Lys Lys Glu Val Val Gly Lys Asp
    130                 135                 140

Leu Leu Lys Gly Ser Leu Leu Phe Thr Ala Gly Pro Leu Glu Glu Glu
145                 150                 155                 160

Arg Phe Gly Ser Pro Ala Phe Ser Gly Ile Ser Arg Leu Thr Trp Leu
                165                 170                 175

Val Ser Leu Phe Gly Glu Leu Ser Leu Val Ser Ala Thr Leu Glu Glu
            180                 185                 190

Arg Lys Glu Asp Gln Tyr Met Lys Met Thr Val Cys Leu Glu Thr Glu
        195                 200                 205

Lys Lys Ser Pro Leu Ser Trp Ile Glu Glu Lys Gly Pro Gly Leu Lys
    210                 215                 220

Arg Asn Arg Tyr Leu Ser Phe His Phe Lys Ser Gly Ser Leu Glu Asn
225                 230                 235                 240

Val Pro Asn Val Gly Val Asn Lys Asn Ile Phe Leu Lys Asp Gln Asn
                245                 250                 255

Ile Phe Val Gln Lys Leu Leu Gly Gln Phe Ser Glu Lys Glu Leu Ala
            260                 265                 270

Ala Glu Lys Lys Arg Ile Leu His Cys Leu Gly Leu Ala Glu Glu Ile
        275                 280                 285

Gln Lys Tyr Cys Cys Ser Arg Lys
    290                 295

<210> SEQ ID NO 4
<211> LENGTH: 296
<212> TYPE: PRT
<213> ORGANISM: Pan troglodytes

<400> SEQUENCE: 4

Met Asn Thr Glu Pro Glu Arg Lys Phe Gly Val Val Val Gly Val
1               5                   10                  15

Gly Arg Ala Gly Ser Val Arg Met Arg Asp Leu Arg Asn Pro His Pro
            20                  25                  30

Ser Ser Ala Phe Leu Asn Leu Ile Gly Phe Val Ser Arg Arg Glu Leu
```

```
        35                  40                  45
Gly Ser Val Asp Gly Val Gln Gln Ile Ser Leu Glu Asp Ala Leu Ser
 50                  55                  60

Ser Gln Glu Val Glu Val Ala Tyr Ile Cys Ser Glu Ser Ser His
 65                  70                  75                  80

Glu Asp Tyr Ile Arg Gln Phe Leu Asn Ala Gly Lys His Val Leu Val
                 85                  90                  95

Glu Tyr Pro Met Thr Leu Ser Leu Ala Ala Ala Gln Glu Leu Trp Glu
            100                 105                 110

Leu Ala Glu Gln Lys Gly Lys Val Leu His Glu Glu His Val Glu Leu
        115                 120                 125

Leu Met Glu Glu Phe Ala Phe Leu Lys Lys Glu Val Val Gly Lys Asp
    130                 135                 140

Leu Leu Lys Gly Ser Leu Leu Phe Thr Ala Gly Pro Leu Glu Glu
145                 150                 155                 160

Arg Phe Gly Phe Pro Ala Phe Ser Gly Ile Ser Arg Leu Thr Trp Leu
                165                 170                 175

Val Ser Leu Phe Gly Glu Leu Ser Leu Val Ser Ala Thr Leu Glu Glu
            180                 185                 190

Arg Lys Glu Asp Gln Tyr Met Lys Met Thr Val Cys Leu Glu Thr Glu
        195                 200                 205

Lys Lys Ser Pro Leu Ser Trp Ile Glu Lys Gly Pro Gly Leu Lys
    210                 215                 220

Arg Asn Arg Tyr Leu Ser Phe His Phe Lys Ser Gly Ser Leu Glu Asn
225                 230                 235                 240

Val Pro Asn Val Gly Val Asn Lys Asn Ile Phe Leu Lys Asp Gln Asn
                245                 250                 255

Ile Phe Val Gln Lys Leu Leu Gly Gln Phe Ser Glu Lys Glu Leu Ala
            260                 265                 270

Ala Glu Lys Lys Arg Ile Leu His Cys Leu Gly Leu Ala Glu Glu Ile
        275                 280                 285

Gln Lys Tyr Cys Cys Ser Arg Lys
    290                 295

<210> SEQ ID NO 5
<211> LENGTH: 296
<212> TYPE: PRT
<213> ORGANISM: Macaca mulatta

<400> SEQUENCE: 5

Met Asn Thr Glu Pro Glu Arg Lys Phe Gly Val Val Val Gly Val
 1               5                  10                  15

Gly Arg Ala Gly Ser Val Arg Met Arg Asp Leu Arg Asn Pro His Pro
                 20                  25                  30

Ser Ser Ala Phe Leu Asn Leu Ile Gly Phe Val Ser Arg Arg Glu Leu
            35                  40                  45

Gly Ser Ile Asp Gly Val Gln Gln Ile Ser Leu Glu Asp Ala Leu Ser
        50                  55                  60

Ser Gln Glu Val Glu Val Ala Tyr Ile Cys Ser Glu Ser Ser His
 65                  70                  75                  80

Glu Asp Tyr Ile Arg Gln Phe Leu Asn Ala Gly Lys His Val Leu Val
                 85                  90                  95

Glu Tyr Pro Met Thr Leu Ser Leu Ala Ala Ala Gln Glu Leu Trp Glu
            100                 105                 110
```

-continued

Leu Ala Glu Gln Lys Gly Lys Val Leu His Glu Glu His Val Glu Leu
            115                 120                 125

Leu Met Glu Glu Phe Ala Phe Leu Lys Lys Glu Val Val Gly Lys Asp
        130                 135                 140

Leu Leu Lys Gly Ser Leu Leu Phe Thr Ala Gly Pro Leu Glu Glu
145                 150                 155                 160

Arg Phe Gly Phe Pro Ala Phe Ser Gly Ile Ser Arg Leu Thr Trp Leu
                165                 170                 175

Val Ser Leu Phe Gly Glu Leu Ser Leu Val Ser Ala Thr Leu Glu Glu
            180                 185                 190

Arg Lys Glu Asp Gln Tyr Met Lys Met Thr Val Cys Leu Glu Thr Glu
        195                 200                 205

Lys Lys Ser Pro Leu Ser Trp Ile Glu Glu Lys Gly Pro Gly Leu Lys
    210                 215                 220

Arg Asn Arg Tyr Leu Ser Phe His Phe Lys Ser Gly Ser Leu Glu Asn
225                 230                 235                 240

Val Pro Asn Val Gly Val Asn Lys Asn Ile Phe Leu Lys Asp Gln Asn
                245                 250                 255

Ile Phe Val Gln Lys Leu Leu Gly Gln Phe Ser Glu Lys Glu Leu Ala
            260                 265                 270

Ala Glu Lys Lys Arg Ile Leu His Cys Leu Gly Leu Ala Glu Glu Ile
        275                 280                 285

Gln Lys Tyr Cys Cys Ser Arg Lys
    290                 295

<210> SEQ ID NO 6
<211> LENGTH: 296
<212> TYPE: PRT
<213> ORGANISM: Bos taurus

<400> SEQUENCE: 6

Met Asn Thr Glu Pro Glu Arg Lys Phe Gly Val Val Val Gly Val
1               5                   10                  15

Gly Arg Ala Gly Ser Val Arg Met Arg Asp Leu Arg Asn Pro His Ala
            20                  25                  30

Ser Ser Ala Phe Leu Asn Leu Ile Gly Phe Val Ser Arg Arg Glu Leu
        35                  40                  45

Gly Ser Ile Asp Glu Val Pro Gln Ile Ser Leu Glu Asp Ala Leu Ser
    50                  55                  60

Ser Gln Glu Val Glu Val Ala Phe Ile Cys Ser Glu Ser Ser His
65                  70                  75                  80

Glu Asp Tyr Ile Arg Gln Phe Leu Asn Ala Gly Lys His Val Leu Val
                85                  90                  95

Glu Tyr Pro Met Thr Leu Ser Trp Val Ala Ala Lys Asp Leu Trp Glu
            100                 105                 110

Leu Ala Glu Gln Lys Gly Lys Val Leu His Glu Glu His Val Glu Leu
        115                 120                 125

Leu Met Glu Glu Phe Ala Phe Leu Lys Lys Glu Val Val Gly Lys Asp
    130                 135                 140

Leu Leu Lys Gly Ser Leu Leu Phe Thr Ala Pro Leu Glu Glu
145                 150                 155                 160

Arg Phe Gly Phe Pro Ala Phe Ser Gly Ile Ser Arg Leu Thr Trp Leu
                165                 170                 175

Val Ser Leu Phe Gly Glu Leu Ser Leu Val Ser Ala Thr Leu Glu Glu
            180                 185                 190

```
Arg Lys Glu Asp Gln Tyr Met Lys Met Thr Val Cys Leu Glu Thr Glu
        195                 200                 205

Asn Lys Ser Pro Leu Thr Trp Ile Glu Glu Lys Ala Pro Gly Leu Lys
    210                 215                 220

Arg Asn Arg Arg Leu Ser Phe His Phe Arg Ser Gly Ser Leu Glu Asn
225                 230                 235                 240

Met Pro Asn Val Gly Ile Asn Lys Asn Ile Phe Leu Lys Asp Gln Asn
                245                 250                 255

Ile Phe Val Gln Lys Leu Leu Gly Gln Phe Ser Glu Glu Glu Leu Ala
                260                 265                 270

Ala Glu Lys Lys Arg Ile Leu His Cys Leu Trp Leu Ala Gly Glu Ile
            275                 280                 285

Gln Lys His Cys Cys Ser Lys Gln
    290                 295

<210> SEQ ID NO 7
<211> LENGTH: 7
<212> TYPE: PRT
<213> ORGANISM: artificial
<220> FEATURE:
<223> OTHER INFORMATION: BVR peptide
<220> FEATURE:
<221> NAME/KEY: MISC_FEATURE
<222> LOCATION: (2)..(2)
<223> OTHER INFORMATION: X is an aromatic amino acid preferably H or Y
<220> FEATURE:
<221> NAME/KEY: MISC_FEATURE
<222> LOCATION: (6)..(7)
<223> OTHER INFORMATION: X is a polar amino acid prefereably Q, R, or K

<400> SEQUENCE: 7

Lys Xaa Cys Cys Ser Xaa Xaa
1               5

<210> SEQ ID NO 8
<211> LENGTH: 7
<212> TYPE: PRT
<213> ORGANISM: artificial
<220> FEATURE:
<223> OTHER INFORMATION: BVR peptide

<400> SEQUENCE: 8

Lys Tyr Cys Cys Ser Arg Lys
1               5

<210> SEQ ID NO 9
<211> LENGTH: 7
<212> TYPE: PRT
<213> ORGANISM: artificial
<220> FEATURE:
<223> OTHER INFORMATION: BVR peptide

<400> SEQUENCE: 9

Lys His Cys Cys Ser Arg Lys
1               5

<210> SEQ ID NO 10
<211> LENGTH: 7
<212> TYPE: PRT
<213> ORGANISM: artificial
<220> FEATURE:
<223> OTHER INFORMATION: BVR peptide

<400> SEQUENCE: 10
```

```
Lys Tyr Cys Cys Ser Lys Lys
1               5

<210> SEQ ID NO 11
<211> LENGTH: 7
<212> TYPE: PRT
<213> ORGANISM: artificial
<220> FEATURE:
<223> OTHER INFORMATION: BVR peptide

<400> SEQUENCE: 11

Lys His Cys Cys Ser Lys Lys
1               5

<210> SEQ ID NO 12
<211> LENGTH: 7
<212> TYPE: PRT
<213> ORGANISM: artificial
<220> FEATURE:
<223> OTHER INFORMATION: BVR peptide

<400> SEQUENCE: 12

Lys Tyr Cys Cys Ser Lys Gln
1               5

<210> SEQ ID NO 13
<211> LENGTH: 7
<212> TYPE: PRT
<213> ORGANISM: artificial
<220> FEATURE:
<223> OTHER INFORMATION: BVR peptide

<400> SEQUENCE: 13

Lys His Cys Cys Ser Lys Gln
1               5

<210> SEQ ID NO 14
<211> LENGTH: 7
<212> TYPE: PRT
<213> ORGANISM: artificial
<220> FEATURE:
<223> OTHER INFORMATION: BVR peptide

<400> SEQUENCE: 14

Lys Tyr Cys Cys Ser Arg Gln
1               5

<210> SEQ ID NO 15
<211> LENGTH: 7
<212> TYPE: PRT
<213> ORGANISM: artificial
<220> FEATURE:
<223> OTHER INFORMATION: BVR peptide

<400> SEQUENCE: 15

Lys His Cys Cys Ser Arg Lys
1               5

<210> SEQ ID NO 16
<211> LENGTH: 7
<212> TYPE: PRT
<213> ORGANISM: artificial
<220> FEATURE:
<223> OTHER INFORMATION: BVR peptide

<400> SEQUENCE: 16

Lys Tyr Cys Cys Ser Lys Arg
```

1               5

<210> SEQ ID NO 17
<211> LENGTH: 7
<212> TYPE: PRT
<213> ORGANISM: artificial
<220> FEATURE:
<223> OTHER INFORMATION: BVR peptide

<400> SEQUENCE: 17

Lys His Cys Cys Ser Lys Arg
1               5

<210> SEQ ID NO 18
<211> LENGTH: 8
<212> TYPE: PRT
<213> ORGANISM: artificial
<220> FEATURE:
<223> OTHER INFORMATION: BVR peptide
<220> FEATURE:
<221> NAME/KEY: MISC_FEATURE
<222> LOCATION: (1)..(2)
<223> OTHER INFORMATION: X is K or R
<220> FEATURE:
<221> NAME/KEY: MISC_FEATURE
<222> LOCATION: (4)..(4)
<223> OTHER INFORMATION: X is K or R
<220> FEATURE:
<221> NAME/KEY: MISC_FEATURE
<222> LOCATION: (6)..(6)
<223> OTHER INFORMATION: X is L or I
<220> FEATURE:
<221> NAME/KEY: MISC_FEATURE
<222> LOCATION: (8)..(8)
<223> OTHER INFORMATION: X is F or W

<400> SEQUENCE: 18

Xaa Xaa Asn Xaa Tyr Xaa Ser Xaa
1               5

<210> SEQ ID NO 19
<211> LENGTH: 8
<212> TYPE: PRT
<213> ORGANISM: artificial
<220> FEATURE:
<223> OTHER INFORMATION: BVR peptide

<400> SEQUENCE: 19

Lys Arg Asn Arg Tyr Leu Ser Phe
1               5

<210> SEQ ID NO 20
<211> LENGTH: 8
<212> TYPE: PRT
<213> ORGANISM: artificial
<220> FEATURE:
<223> OTHER INFORMATION: BVR peptide

<400> SEQUENCE: 20

Lys Lys Asn Arg Tyr Leu Ser Phe
1               5

<210> SEQ ID NO 21
<211> LENGTH: 8
<212> TYPE: PRT
<213> ORGANISM: artificial
<220> FEATURE:
<223> OTHER INFORMATION: BVR peptide

<400> SEQUENCE: 21

```
Arg Arg Asn Arg Tyr Leu Ser Phe
1               5

<210> SEQ ID NO 22
<211> LENGTH: 8
<212> TYPE: PRT
<213> ORGANISM: artificial
<220> FEATURE:
<223> OTHER INFORMATION: BVR peptide

<400> SEQUENCE: 22

Lys Arg Asn Arg Tyr Ile Ser Phe
1               5

<210> SEQ ID NO 23
<211> LENGTH: 8
<212> TYPE: PRT
<213> ORGANISM: artificial
<220> FEATURE:
<223> OTHER INFORMATION: BVR peptide

<400> SEQUENCE: 23

Lys Arg Asn Arg Tyr Leu Ser Trp
1               5

<210> SEQ ID NO 24
<211> LENGTH: 11
<212> TYPE: PRT
<213> ORGANISM: artificial
<220> FEATURE:
<223> OTHER INFORMATION: BVR peptide
<220> FEATURE:
<221> NAME/KEY: MISC_FEATURE
<222> LOCATION: (1)..(3)
<223> OTHER INFORMATION: X is K or R
<220> FEATURE:
<221> NAME/KEY: MISC_FEATURE
<222> LOCATION: (4)..(4)
<223> OTHER INFORMATION: X is I or L
<220> FEATURE:
<221> NAME/KEY: MISC_FEATURE
<222> LOCATION: (6)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid

<400> SEQUENCE: 24

Xaa Xaa Xaa Xaa Leu Xaa Xaa Leu Xaa Leu Ala
1               5                   10

<210> SEQ ID NO 25
<211> LENGTH: 11
<212> TYPE: PRT
<213> ORGANISM: artificial
<220> FEATURE:
<223> OTHER INFORMATION: BVR peptide

<400> SEQUENCE: 25

Lys Lys Arg Ile Leu His Cys Leu Gly Leu Ala
1               5                   10

<210> SEQ ID NO 26
<211> LENGTH: 11
<212> TYPE: PRT
<213> ORGANISM: artificial
<220> FEATURE:
<223> OTHER INFORMATION: BVR peptide
```

<400> SEQUENCE: 26

Arg Lys Arg Ile Leu His Cys Leu Gly Leu Ala
1               5                   10

<210> SEQ ID NO 27
<211> LENGTH: 11
<212> TYPE: PRT
<213> ORGANISM: artificial
<220> FEATURE:
<223> OTHER INFORMATION: BVR peptide

<400> SEQUENCE: 27

Lys Arg Arg Ile Leu His Cys Leu Gly Leu Ala
1               5                   10

<210> SEQ ID NO 28
<211> LENGTH: 11
<212> TYPE: PRT
<213> ORGANISM: artificial
<220> FEATURE:
<223> OTHER INFORMATION: BVR peptide

<400> SEQUENCE: 28

Lys Lys Arg Leu Leu His Cys Leu Gly Leu Ala
1               5                   10

<210> SEQ ID NO 29
<211> LENGTH: 11
<212> TYPE: PRT
<213> ORGANISM: artificial
<220> FEATURE:
<223> OTHER INFORMATION: BVR peptide

<400> SEQUENCE: 29

Arg Arg Arg Ile Leu His Cys Leu Gly Leu Ala
1               5                   10

<210> SEQ ID NO 30
<211> LENGTH: 11
<212> TYPE: PRT
<213> ORGANISM: artificial
<220> FEATURE:
<223> OTHER INFORMATION: BVR peptide

<400> SEQUENCE: 30

Lys Arg Lys Ile Leu His Cys Leu Gly Leu Ala
1               5                   10

<210> SEQ ID NO 31
<211> LENGTH: 11
<212> TYPE: PRT
<213> ORGANISM: artificial
<220> FEATURE:
<223> OTHER INFORMATION: BVR peptide

<400> SEQUENCE: 31

Arg Arg Arg Leu Leu His Cys Leu Gly Leu Ala
1               5                   10

<210> SEQ ID NO 32
<211> LENGTH: 11
<212> TYPE: PRT
<213> ORGANISM: artificial
<220> FEATURE:
<223> OTHER INFORMATION: BVR peptide -continued

<400> SEQUENCE: 32

Lys Lys Lys Leu Leu His Cys Leu Gly Leu Ala
1               5                   10

<210> SEQ ID NO 33
<211> LENGTH: 8
<212> TYPE: PRT
<213> ORGANISM: artificial
<220> FEATURE:
<223> OTHER INFORMATION: BVR peptide
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (5)..(5)
<223> OTHER INFORMATION: X is any amino acid
<220> FEATURE:
<221> NAME/KEY: MISC_FEATURE
<222> LOCATION: (7)..(7)
<223> OTHER INFORMATION: X is S or T

<400> SEQUENCE: 33

Phe Xaa Phe Pro Xaa Phe Xaa Gly
1               5

<210> SEQ ID NO 34
<211> LENGTH: 8
<212> TYPE: PRT
<213> ORGANISM: artificial
<220> FEATURE:
<223> OTHER INFORMATION: BVR peptide

<400> SEQUENCE: 34

Phe Gly Phe Pro Ala Phe Ser Gly
1               5

<210> SEQ ID NO 35
<211> LENGTH: 8
<212> TYPE: PRT
<213> ORGANISM: artificial
<220> FEATURE:
<223> OTHER INFORMATION: BVR peptide

<400> SEQUENCE: 35

Phe Gly Phe Pro Ala Phe Thr Gly
1               5

<210> SEQ ID NO 36
<211> LENGTH: 8
<212> TYPE: PRT
<213> ORGANISM: artificial
<220> FEATURE:
<223> OTHER INFORMATION: BVR peptide

<400> SEQUENCE: 36

Phe Ala Phe Pro Gly Phe Ser Gly
1               5

<210> SEQ ID NO 37
<211> LENGTH: 8
<212> TYPE: PRT
<213> ORGANISM: artificial
<220> FEATURE:
<223> OTHER INFORMATION: BVR peptide

<400> SEQUENCE: 37

```
Phe Ala Phe Pro Gly Phe Thr Gly
1               5

<210> SEQ ID NO 38
<211> LENGTH: 8
<212> TYPE: PRT
<213> ORGANISM: artificial
<220> FEATURE:
<223> OTHER INFORMATION: BVR peptide

<400> SEQUENCE: 38

Phe Ala Phe Pro Ala Phe Thr Gly
1               5

<210> SEQ ID NO 39
<211> LENGTH: 8
<212> TYPE: PRT
<213> ORGANISM: artificial
<220> FEATURE:
<223> OTHER INFORMATION: BVR peptide

<400> SEQUENCE: 39

Phe Gly Phe Pro Gly Phe Ser Gly
1               5

<210> SEQ ID NO 40
<211> LENGTH: 8
<212> TYPE: PRT
<213> ORGANISM: artificial
<220> FEATURE:
<223> OTHER INFORMATION: BVR peptide

<400> SEQUENCE: 40

Phe Gly Phe Pro Gly Phe Thr Gly
1               5

<210> SEQ ID NO 41
<211> LENGTH: 6
<212> TYPE: PRT
<213> ORGANISM: artificial
<220> FEATURE:
<223> OTHER INFORMATION: BVR peptide
<220> FEATURE:
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (5)..(5)
<223> OTHER INFORMATION: X is any amino acid

<400> SEQUENCE: 41

Leu Xaa Xaa Leu Xaa Leu
1               5

<210> SEQ ID NO 42
<211> LENGTH: 10
<212> TYPE: PRT
<213> ORGANISM: artificial
<220> FEATURE:
<223> OTHER INFORMATION: BVR peptide
<220> FEATURE:
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (5)..(7)
<223> OTHER INFORMATION: X is any amino acid
<220> FEATURE:
```

```
<221> NAME/KEY: MISC_FEATURE
<222> LOCATION: (9)..(9)
<223> OTHER INFORMATION: X is any amino acid

<400> SEQUENCE: 42

Leu Xaa Xaa Leu Xaa Xaa Xaa Leu Xaa Leu
1               5                   10

<210> SEQ ID NO 43
<211> LENGTH: 16
<212> TYPE: PRT
<213> ORGANISM: artificial
<220> FEATURE:
<223> OTHER INFORMATION: BVR peptide
<220> FEATURE:
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (5)..(6)
<223> OTHER INFORMATION: X is any amino acid
<220> FEATURE:
<221> NAME/KEY: MISC_FEATURE
<222> LOCATION: (8)..(9)
<223> OTHER INFORMATION: X is any amino acid
<220> FEATURE:
<221> NAME/KEY: MISC_FEATURE
<222> LOCATION: (11)..(13)
<223> OTHER INFORMATION: X is any amino acid
<220> FEATURE:
<221> NAME/KEY: MISC_FEATURE
<222> LOCATION: (15)..(15)
<223> OTHER INFORMATION: X is any amino acid

<400> SEQUENCE: 43

Ile Xaa Xaa Leu Xaa Xaa Leu Xaa Xaa Leu Xaa Xaa Xaa Leu Xaa Leu
1               5                   10                  15

<210> SEQ ID NO 44
<211> LENGTH: 14
<212> TYPE: PRT
<213> ORGANISM: artificial
<220> FEATURE:
<223> OTHER INFORMATION: BVR peptide
<220> FEATURE:
<221> NAME/KEY: MISC_FEATURE
<222> LOCATION: (3)..(4)
<223> OTHER INFORMATION: X is K or R
<220> FEATURE:
<221> NAME/KEY: MISC_FEATURE
<222> LOCATION: (6)..(6)
<223> OTHER INFORMATION: X is K or R
<220> FEATURE:
<221> NAME/KEY: MISC_FEATURE
<222> LOCATION: (7)..(7)
<223> OTHER INFORMATION: X is F, Y, or W
<220> FEATURE:
<221> NAME/KEY: MISC_FEATURE
<222> LOCATION: (9)..(9)
<223> OTHER INFORMATION: X is S or T
<220> FEATURE:
<221> NAME/KEY: MISC_FEATURE
<222> LOCATION: (10)..(10)
<223> OTHER INFORMATION: X is F, Y, or W
<220> FEATURE:
<221> NAME/KEY: MISC_FEATURE
<222> LOCATION: (11)..(11)
<223> OTHER INFORMATION: X is K, R, or H
<220> FEATURE:
<221> NAME/KEY: MISC_FEATURE
<222> LOCATION: (12)..(12)
<223> OTHER INFORMATION: X is F, Y, or W
<220> FEATURE:
<221> NAME/KEY: MISC_FEATURE
```

```
<222> LOCATION: (13)..(13)
<223> OTHER INFORMATION: X is K or R
<220> FEATURE:
<221> NAME/KEY: MISC_FEATURE
<222> LOCATION: (14)..(14)
<223> OTHER INFORMATION: X is S or T

<400> SEQUENCE: 44

Gly Leu Xaa Xaa Asn Xaa Xaa Leu Xaa Xaa Xaa Xaa Xaa Xaa
1               5                   10

<210> SEQ ID NO 45
<211> LENGTH: 14
<212> TYPE: PRT
<213> ORGANISM: artificial
<220> FEATURE:
<223> OTHER INFORMATION: BVR peptide

<400> SEQUENCE: 45

Gly Leu Lys Arg Asn Arg Tyr Leu Ser Phe His Phe Lys Ser
1               5                   10

<210> SEQ ID NO 46
<211> LENGTH: 3
<212> TYPE: PRT
<213> ORGANISM: artificial
<220> FEATURE:
<223> OTHER INFORMATION: PKC phosphorylation motif
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is R of K

<400> SEQUENCE: 46

Ser Xaa Xaa
1

<210> SEQ ID NO 47
<211> LENGTH: 4
<212> TYPE: PRT
<213> ORGANISM: artificial
<220> FEATURE:
<223> OTHER INFORMATION: BVR peptide
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (4)..(4)
<223> OTHER INFORMATION: X is R or K

<400> SEQUENCE: 47

Ser Thr Xaa Xaa
1

<210> SEQ ID NO 48
<211> LENGTH: 21
<212> TYPE: RNA
<213> ORGANISM: artificial
<220> FEATURE:
<223> OTHER INFORMATION: BVR SiRNA

<400> SEQUENCE: 48
uccucagcgu uccugaaccu g                                         21
```

```
<210> SEQ ID NO 49
<211> LENGTH: 21
<212> TYPE: RNA
<213> ORGANISM: artificial
<220> FEATURE:
<223> OTHER INFORMATION: BVR SiRNA

<400> SEQUENCE: 49
aggagucgca aggacuugga c                                             21

<210> SEQ ID NO 50
<211> LENGTH: 6
<212> TYPE: PRT
<213> ORGANISM: artificial
<220> FEATURE:
<223> OTHER INFORMATION: ATP/Adenine binding domain
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (4)..(5)
<223> OTHER INFORMATION: X is any amino acid

<400> SEQUENCE: 50

Gly Xaa Gly Xaa Xaa Gly
1               5

<210> SEQ ID NO 51
<211> LENGTH: 10
<212> TYPE: PRT
<213> ORGANISM: artificial
<220> FEATURE:
<223> OTHER INFORMATION: PKC-delta fragment

<400> SEQUENCE: 51

Gln Ala Lys Ile His Tyr Ile Lys Asn Glu
1               5                   10

<210> SEQ ID NO 52
<211> LENGTH: 12
<212> TYPE: PRT
<213> ORGANISM: artificial
<220> FEATURE:
<223> OTHER INFORMATION: PKC-delta substrate

<400> SEQUENCE: 52

Ala Arg Arg Lys Arg Lys Gly Ser Phe Phe Gly Gly
1               5                   10

<210> SEQ ID NO 53
<211> LENGTH: 9
<212> TYPE: PRT
<213> ORGANISM: artificial
<220> FEATURE:
<223> OTHER INFORMATION: BVR peptide

<400> SEQUENCE: 53

Ser Phe His Phe Lys Ser Gly Ser Leu
1               5

<210> SEQ ID NO 54
<211> LENGTH: 4
<212> TYPE: PRT
<213> ORGANISM: artificial
<220> FEATURE:
<223> OTHER INFORMATION: PKC phosphorylation motif
```

```
<220> FEATURE:
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (4)..(4)
<223> OTHER INFORMATION: X is S or T

<400> SEQUENCE: 54

Arg Xaa Xaa Xaa
1

<210> SEQ ID NO 55
<211> LENGTH: 5
<212> TYPE: PRT
<213> ORGANISM: artificial
<220> FEATURE:
<223> OTHER INFORMATION: BVR peptide

<400> SEQUENCE: 55

Arg Tyr Leu Ser Phe
1               5

<210> SEQ ID NO 56
<211> LENGTH: 15
<212> TYPE: PRT
<213> ORGANISM: artificial
<220> FEATURE:
<223> OTHER INFORMATION: PKC substrate

<400> SEQUENCE: 56

Lys Lys Lys Arg Phe Ser Phe Lys Lys Ser Phe Lys Leu Ser Gly
1               5                   10                  15

<210> SEQ ID NO 57
<211> LENGTH: 19
<212> TYPE: PRT
<213> ORGANISM: artificial
<220> FEATURE:
<223> OTHER INFORMATION: PKC-delta c-terminal peptide

<400> SEQUENCE: 57

Ser Ala Phe Ala Gly Phe Ser Phe Val Asn Pro Lys Phe Glu His Leu
1               5                   10                  15

Leu Glu Asp

<210> SEQ ID NO 58
<211> LENGTH: 17
<212> TYPE: PRT
<213> ORGANISM: artificial
<220> FEATURE:
<223> OTHER INFORMATION: BVR peptide

<400> SEQUENCE: 58

Gly Leu Lys Arg Asn Arg Tyr Leu Ala Phe His Phe Lys Ser Gly Ser
1               5                   10                  15

Leu

<210> SEQ ID NO 59
<211> LENGTH: 13
<212> TYPE: PRT
<213> ORGANISM: artificial
<220> FEATURE:
<223> OTHER INFORMATION: BVR peptide

<400> SEQUENCE: 59
```

```
Gly Leu Lys Arg Asn Arg Tyr Leu Ala Phe His Phe Lys
1               5                   10
```

<210> SEQ ID NO 60
<211> LENGTH: 13
<212> TYPE: PRT
<213> ORGANISM: artificial
<220> FEATURE:
<223> OTHER INFORMATION: BVR peptide

<400> SEQUENCE: 60

```
Gly Leu Ala Ala Asn Ala Tyr Leu Ser Phe His Phe Lys
1               5                   10
```

<210> SEQ ID NO 61
<211> LENGTH: 6
<212> TYPE: PRT
<213> ORGANISM: artificial
<220> FEATURE:
<223> OTHER INFORMATION: PKC-delta peptide

<400> SEQUENCE: 61

```
Phe Ala Gly Phe Ser Phe
1               5
```

<210> SEQ ID NO 62
<211> LENGTH: 6
<212> TYPE: PRT
<213> ORGANISM: artificial
<220> FEATURE:
<223> OTHER INFORMATION: PKC-delta bulky ring motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 62

```
Phe Xaa Xaa Phe Xaa Phe
1               5
```

<210> SEQ ID NO 63
<211> LENGTH: 6
<212> TYPE: PRT
<213> ORGANISM: artificial
<220> FEATURE:
<223> OTHER INFORMATION: BVR phenylalanine-rich motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 63

```
Phe Xaa Phe Xaa Xaa Phe
1               5
```

<210> SEQ ID NO 64
<211> LENGTH: 29
<212> TYPE: PRT
<213> ORGANISM: artificial
<220> FEATURE:
<223> OTHER INFORMATION: endoplasmic reticulum signal peptide

<400> SEQUENCE: 64

Met Met Ser Phe Val Ser Leu Leu Leu Val Gly Ile Leu Phe Tyr Ala
1               5                   10                  15

Thr Glu Ala Glu Gln Leu Thr Lys Cys Glu Val Phe Gln
            20                  25

<210> SEQ ID NO 65
<211> LENGTH: 4
<212> TYPE: PRT
<213> ORGANISM: artificial
<220> FEATURE:
<223> OTHER INFORMATION: endoplasmic reticulum retention signal

<400> SEQUENCE: 65

Lys Glu Asp Leu
1

<210> SEQ ID NO 66
<211> LENGTH: 8
<212> TYPE: PRT
<213> ORGANISM: artificial
<220> FEATURE:
<223> OTHER INFORMATION: nuclear transport peptide

<400> SEQUENCE: 66

Pro Pro Lys Lys Lys Arg Lys Val
1               5

<210> SEQ ID NO 67
<211> LENGTH: 25
<212> TYPE: PRT
<213> ORGANISM: artificial
<220> FEATURE:
<223> OTHER INFORMATION: mitochondria targeting sequence

<400> SEQUENCE: 67

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 68
<211> LENGTH: 4
<212> TYPE: PRT
<213> ORGANISM: artificial
<220> FEATURE:
<223> OTHER INFORMATION: BVR peptide

<400> SEQUENCE: 68

Tyr Met Lys Met
1

<210> SEQ ID NO 69
<211> LENGTH: 4
<212> TYPE: PRT
<213> ORGANISM: artificial
<220> FEATURE:
<223> OTHER INFORMATION: BVR peptide

<400> SEQUENCE: 69

Tyr Leu Ser Phe
1

<210> SEQ ID NO 70

```
<211> LENGTH: 13
<212> TYPE: PRT
<213> ORGANISM: artificial
<220> FEATURE:
<223> OTHER INFORMATION: BVR peptide

<400> SEQUENCE: 70

Gly Leu Lys Arg Asn Arg Tyr Leu Ser Phe His Phe Lys
1               5                   10
```